(12) United States Patent
Levinson et al.

(10) Patent No.: US 9,041,541 B2
(45) Date of Patent: May 26, 2015

(54) MONITORING OR FEEDBACK SYSTEMS AND METHODS

(75) Inventors: Douglas A. Levinson, Sherborn, MA (US); Howard Bernstein, Cambridge, MA (US); Donald E. Chickering, III, Framingham, MA (US)

(73) Assignee: Seventh Sense Biosystems, Inc., Cambridge, MA (US)

( * ) Notice: Subject to any disclaimer, the term of this patent is extended or adjusted under 35 U.S.C. 154(b) by 359 days.

(21) Appl. No.: 13/016,575

(22) Filed: Jan. 28, 2011

(65) Prior Publication Data
US 2011/0181410 A1    Jul. 28, 2011

Related U.S. Application Data

(60) Provisional application No. 61/299,283, filed on Jan. 28, 2010.

(51) Int. Cl.
*G08B 23/00* (2006.01)
*G06F 19/00* (2011.01)

(52) U.S. Cl.
CPC ................... *G06F 19/3456* (2013.01)

(58) Field of Classification Search
CPC ............ G06F 19/3456; G06F 19/3418; G06F 19/3462; A61J 2200/30
USPC .................. 340/573.1, 539.12; 600/300, 309; 705/14.1, 14.4, 2
See application file for complete search history.

(56) References Cited

U.S. PATENT DOCUMENTS 3,060,429 A    10/1962   Winston
3,339,546 A     9/1967   Chen
(Continued)

FOREIGN PATENT DOCUMENTS

CN    1222334 A    7/1999
CN    1499949      5/2004
(Continued)

OTHER PUBLICATIONS

International Search Report and Written Opinion for PCT/US2009/046333 mailed Dec. 9, 2009.
(Continued)

*Primary Examiner* — Thomas Mullen
(74) *Attorney, Agent, or Firm* — Wolf, Greenfield & Sacks, P.C.

(57) ABSTRACT

The present invention generally relates to systems and methods for monitoring and/or providing feedback for drugs or other pharmaceuticals taken by a subject. In one aspect, the present invention is directed to devices and methods for determining a species within the skin of a subject; and producing feedback to a subject based on the determination of the species. The feedback may be, for example, visual, audible, tactile, a change in temperature, etc. In some cases, information regarding the determination of the species may be transmitted to another entity, e.g., a health care provider, a computer, a relative, etc., which may then provide feedback to the subject in some fashion. In some cases, the feedback may be directly indicative of the species, e.g., whether the species is present, the concentration of the species, whether a by-product of a reaction involving the species is present, whether a compound affected by the species is present, etc. However, the feedback may also be indirect in some embodiments. For example, the subject may be presented with an external reward, e.g., based on the determination of the species within the skin. For instance, a reward such as cash, coupons, songs, discounts, personal items, etc., may be offered based on the level of compliance of the subject. Still other aspects of the invention are generally directed to kits involving such devices (with or without the drug to be monitored), methods of promoting such systems, or the like.

28 Claims, 5 Drawing Sheets

(56) References Cited

U.S. PATENT DOCUMENTS

| | | |
|---|---|---|
| 3,551,554 A | 12/1970 | Herschler |
| 3,645,253 A | 2/1972 | Goverde et al. |
| 3,711,602 A | 1/1973 | Herschler |
| 3,711,606 A | 1/1973 | Herschler |
| 3,740,421 A | 6/1973 | Schmolka |
| 3,761,013 A | 9/1973 | Schuster |
| 3,908,657 A | 9/1975 | Kowarski |
| 4,103,684 A | 8/1978 | Ismach |
| 4,150,744 A | 4/1979 | Fennimore |
| 4,203,520 A | 5/1980 | Schuster |
| 4,253,460 A | 3/1981 | Chen et al. |
| 4,329,999 A | 5/1982 | Phillips |
| 4,437,567 A | 3/1984 | Jeng |
| 4,537,776 A | 8/1985 | Cooper |
| 4,553,552 A | 11/1985 | Valdespino et al. |
| 4,557,943 A | 12/1985 | Rosler et al. |
| 4,615,697 A | 10/1986 | Robinson |
| 4,621,268 A | 11/1986 | Keeling et al. |
| 4,637,403 A | 1/1987 | Garcia et al. |
| 4,696,309 A | 9/1987 | Stephan |
| 4,706,676 A | 11/1987 | Peck |
| 4,740,365 A | 4/1988 | Yukimatsu et al. |
| 4,756,314 A | 7/1988 | Eckenhoff et al. |
| 4,764,378 A | 8/1988 | Keith et al. |
| 4,772,470 A | 9/1988 | Inoue et al. |
| 4,796,644 A | 1/1989 | Polaschegg |
| 4,820,720 A | 4/1989 | Sanders et al. |
| 4,821,733 A | 4/1989 | Peck |
| 4,855,298 A | 8/1989 | Yamada et al. |
| 4,863,970 A | 9/1989 | Patel et al. |
| 4,908,404 A | 3/1990 | Benedict et al. |
| 4,957,108 A | 9/1990 | Schoendorfer et al. |
| 4,971,068 A | 11/1990 | Sahi |
| 4,973,468 A | 11/1990 | Chiang et al. |
| 5,006,342 A | 4/1991 | Cleary et al. |
| 5,015,677 A | 5/1991 | Benedict et al. |
| 5,036,861 A | 8/1991 | Sembrowich et al. |
| 5,054,499 A | 10/1991 | Swierczek |
| 5,076,273 A | 12/1991 | Schoendorfer et al. |
| 5,108,927 A | 4/1992 | Dorn |
| 5,161,532 A | 11/1992 | Joseph |
| 5,174,291 A | 12/1992 | Schoonen et al. |
| 5,201,324 A | 4/1993 | Swierczek |
| 5,213,568 A | 5/1993 | Lattin et al. |
| 5,231,993 A | 8/1993 | Haber et al. |
| 5,279,294 A | 1/1994 | Anderson et al. |
| 5,320,607 A | 6/1994 | Ishibashi |
| 5,379,895 A | 1/1995 | Foslien |
| 5,402,798 A | 4/1995 | Swierczek et al. |
| 5,438,984 A | 8/1995 | Schoendorfer |
| 5,441,048 A | 8/1995 | Schoendorfer |
| 5,441,490 A | 8/1995 | Svedman |
| 5,443,080 A | 8/1995 | D'Angelo et al. |
| 5,445,611 A | 8/1995 | Eppstein et al. |
| 5,458,140 A | 10/1995 | Eppstein et al. |
| 5,505,212 A | 4/1996 | Keljmann et al. |
| 5,507,288 A | 4/1996 | Bocker et al. |
| 5,520,727 A | 5/1996 | Vreeland et al. |
| 5,529,581 A | 6/1996 | Cusack |
| 5,540,709 A | 7/1996 | Ramel |
| 5,552,118 A | 9/1996 | Mayer |
| 5,560,543 A | 10/1996 | Smith et al. |
| 5,574,134 A | 11/1996 | Waite |
| 5,580,794 A | 12/1996 | Allen |
| 5,582,184 A | 12/1996 | Erickson et al. |
| 5,636,640 A | 6/1997 | Staehlin |
| 5,638,815 A | 6/1997 | Schoendorfer |
| 5,662,127 A | 9/1997 | De Vaughn |
| 5,676,144 A | 10/1997 | Schoendorfer |
| 5,680,872 A | 10/1997 | Sesekura et al. |
| 5,682,233 A | 10/1997 | Brinda |
| 5,685,875 A | 11/1997 | Hlavinka et al. |
| 5,714,390 A | 2/1998 | Hallowitz et al. |
| 5,741,138 A | 4/1998 | Rice et al. |
| 5,746,217 A | 5/1998 | Erickson et al. |
| 5,800,420 A | 9/1998 | Gross et al. |
| 5,807,375 A | 9/1998 | Gross et al. |
| 5,811,108 A | 9/1998 | Goeringer |
| 5,813,614 A | 9/1998 | Coffee |
| 5,817,011 A | 10/1998 | Schoendorfer |
| 5,817,012 A | 10/1998 | Schoendorfer |
| 5,820,570 A | 10/1998 | Erickson et al. |
| 5,820,622 A | 10/1998 | Gross et al. |
| 5,823,973 A | 10/1998 | Racchini et al. |
| 5,857,983 A | 1/1999 | Douglas et al. |
| 5,858,188 A | 1/1999 | Soane et al. |
| 5,873,900 A | 2/1999 | Maurer et al. |
| 5,876,675 A | 3/1999 | Kennedy |
| 5,879,310 A | 3/1999 | Sopp et al. |
| 5,879,311 A | 3/1999 | Duchon et al. |
| 5,879,367 A | 3/1999 | Latterell et al. |
| 5,885,211 A | 3/1999 | Eppstein et al. |
| 5,891,053 A | 4/1999 | Sesekura |
| 5,944,662 A | 8/1999 | Schoendorfer |
| 5,951,492 A | 9/1999 | Douglas et al. |
| 5,951,493 A | 9/1999 | Douglas et al. |
| 5,955,096 A | 9/1999 | Santos et al. |
| 5,963,136 A * | 10/1999 | O'Brien ................ 340/573.1 |
| 5,964,718 A | 10/1999 | Duchon et al. |
| 5,985,312 A | 11/1999 | Jacob et al. |
| 5,998,588 A | 12/1999 | Hoffman et al. |
| 6,007,845 A | 12/1999 | Domb et al. |
| 6,015,392 A | 1/2000 | Douglas et al. |
| 6,027,459 A | 2/2000 | Shain et al. |
| 6,044,303 A | 3/2000 | Agarwala et al. |
| 6,048,337 A | 4/2000 | Svedman |
| 6,050,988 A | 4/2000 | Zuck |
| 6,063,029 A | 5/2000 | Saita et al. |
| 6,063,039 A | 5/2000 | Cunningham et al. |
| 6,063,365 A | 5/2000 | Shefer et al. |
| 6,066,103 A | 5/2000 | Duchon et al. |
| 6,071,249 A | 6/2000 | Cunningham et al. |
| 6,071,250 A | 6/2000 | Douglas et al. |
| 6,071,251 A | 6/2000 | Cunningham et al. |
| 6,080,116 A | 6/2000 | Erickson et al. |
| 6,083,196 A | 7/2000 | Trautman et al. |
| 6,091,975 A | 7/2000 | Daddona et al. |
| 6,093,156 A | 7/2000 | Cunningham et al. |
| 6,099,484 A | 8/2000 | Douglas et al. |
| 6,107,102 A | 8/2000 | Ferrari |
| 6,126,899 A | 10/2000 | Woudenberg et al. |
| 6,132,449 A | 10/2000 | Lum et al. |
| 6,132,702 A | 10/2000 | Witt et al. |
| 6,152,889 A | 11/2000 | Sopp et al. |
| 6,152,942 A | 11/2000 | Brenneman et al. |
| 6,155,992 A | 12/2000 | Henning et al. |
| 6,162,639 A | 12/2000 | Douglas |
| 6,190,315 B1 | 2/2001 | Kost et al. |
| 6,192,890 B1 | 2/2001 | Levy et al. |
| 6,203,504 B1 | 3/2001 | Latterell et al. |
| 6,206,841 B1 | 3/2001 | Cunningham et al. |
| 6,219,574 B1 | 4/2001 | Cormier et al. |
| 6,228,100 B1 | 5/2001 | Schraga |
| 6,230,051 B1 | 5/2001 | Cormier et al. |
| 6,234,990 B1 | 5/2001 | Rowe et al. |
| 6,235,313 B1 | 5/2001 | Mathiowitz et al. |
| 6,252,129 B1 | 6/2001 | Coffee |
| 6,267,724 B1 | 7/2001 | Taylor |
| 6,283,926 B1 | 9/2001 | Cunningham et al. |
| 6,306,104 B1 | 10/2001 | Cunningham et al. |
| 6,306,993 B1 | 10/2001 | Rothbard et al. |
| 6,309,887 B1 | 10/2001 | Ray |
| 6,319,210 B1 | 11/2001 | Douglas et al. |
| 6,322,574 B1 | 11/2001 | Lloyd |
| 6,332,871 B1 | 12/2001 | Douglas et al. |
| 6,334,856 B1 | 1/2002 | Allen et al. |
| 6,340,354 B1 | 1/2002 | Rambin |
| 6,349,229 B1 | 2/2002 | Watanabe et al. |
| 6,349,850 B1 | 2/2002 | Cheikh |
| 6,361,944 B1 | 3/2002 | Mirkin et al. |
| 6,364,890 B1 | 4/2002 | Lum et al. |
| 6,379,324 B1 | 4/2002 | Gartstein et al. |
| 6,391,471 B1 | 5/2002 | Hiraoka et al. |
| 6,406,919 B1 | 6/2002 | Tyrrell |

(56) References Cited

U.S. PATENT DOCUMENTS

| | | |
|---|---|---|
| 6,409,679 B2 | 6/2002 | Pyo |
| 6,436,078 B1 | 8/2002 | Svedman |
| 6,440,096 B1 | 8/2002 | Lastovich et al. |
| 6,455,324 B1 | 9/2002 | Douglas |
| 6,461,644 B1 | 10/2002 | Jackson et al. |
| 6,464,649 B1 | 10/2002 | Duchon et al. |
| 6,465,002 B1 | 10/2002 | Mathiowitz et al. |
| 6,485,439 B1 | 11/2002 | Roe et al. |
| 6,485,703 B1 | 11/2002 | Cote et al. |
| 6,491,657 B2 | 12/2002 | Rowe et al. |
| 6,491,902 B2 | 12/2002 | Shefer et al. |
| 6,501,976 B1 | 12/2002 | Sohrab |
| 6,502,697 B1 | 1/2003 | Crampton et al. |
| 6,503,209 B2 | 1/2003 | Hakky et al. |
| 6,503,231 B1 | 1/2003 | Prausnitz et al. |
| 6,506,168 B1 | 1/2003 | Fathallah et al. |
| 6,527,716 B1 | 3/2003 | Eppstein |
| 6,532,386 B2 | 3/2003 | Sun et al. |
| 6,537,243 B1 | 3/2003 | Henning et al. |
| 6,537,264 B1 | 3/2003 | Cormier et al. |
| 6,538,089 B1 | 3/2003 | Samra et al. |
| 6,540,675 B2 | 4/2003 | Aceti et al. |
| 6,548,264 B1 | 4/2003 | Tan et al. |
| 6,558,361 B1 | 5/2003 | Yeshurun |
| 6,562,014 B2 | 5/2003 | Lin et al. |
| 6,589,562 B1 | 7/2003 | Shefer et al. |
| 6,591,124 B2 | 7/2003 | Sherman et al. |
| 6,602,205 B1 | 8/2003 | Erickson et al. |
| 6,603,987 B2 | 8/2003 | Whitson |
| 6,607,495 B1 | 8/2003 | Skalak et al. |
| 6,607,513 B1 | 8/2003 | Down et al. |
| 6,611,707 B1 | 8/2003 | Prausnitz et al. |
| 6,614,522 B1 | 9/2003 | Sopp et al. |
| 6,620,123 B1 | 9/2003 | Mitragotri et al. |
| 6,624,882 B2 | 9/2003 | Sopp et al. |
| 6,626,884 B2 | 9/2003 | Dillon et al. |
| 6,652,478 B1 | 11/2003 | Gartstein et al. |
| 6,656,147 B1 | 12/2003 | Gertsek et al. |
| 6,660,527 B2 | 12/2003 | Stroup |
| 6,669,961 B2 | 12/2003 | Kim et al. |
| 6,678,554 B1 | 1/2004 | Sun et al. |
| 6,685,921 B2 | 2/2004 | Lawlor |
| 6,689,100 B2 | 2/2004 | Connelly et al. |
| 6,696,075 B2 | 2/2004 | Mathiowitz et al. |
| 6,706,000 B2 | 3/2004 | Perez et al. |
| 6,706,159 B2 | 3/2004 | Moerman et al. |
| 6,712,776 B2 | 3/2004 | Latterell et al. |
| 6,741,877 B1 | 5/2004 | Shults et al. |
| 6,743,211 B1 | 6/2004 | Prausnitz et al. |
| 6,749,575 B2 | 6/2004 | Matriano et al. |
| 6,765,081 B2 | 7/2004 | Lin et al. |
| 6,766,817 B2 | 7/2004 | da Silva |
| 6,768,920 B2 | 7/2004 | Lange et al. |
| 6,783,502 B2 | 8/2004 | Orloff et al. |
| 6,786,874 B2 | 9/2004 | Grace et al. |
| 6,793,633 B2 | 9/2004 | Douglas et al. |
| 6,798,920 B1 | 9/2004 | Wells et al. |
| 6,800,122 B2 | 10/2004 | Anderson et al. |
| 6,811,090 B2 | 11/2004 | Yogi et al. |
| 6,814,760 B2 | 11/2004 | Anderson et al. |
| 6,825,161 B2 | 11/2004 | Shefer et al. |
| 6,826,426 B2 | 11/2004 | Lange et al. |
| 6,837,858 B2 | 1/2005 | Cunningham et al. |
| 6,855,133 B2 | 2/2005 | Svedman |
| 6,860,873 B2 | 3/2005 | Allen et al. |
| 6,878,120 B2 | 4/2005 | Roe et al. |
| 6,896,666 B2 | 5/2005 | Kochamba |
| 6,899,851 B2 | 5/2005 | Allen et al. |
| 6,908,448 B2 | 6/2005 | Redding, Jr. |
| 6,918,404 B2 | 7/2005 | Dias da Silva |
| 6,918,901 B1 | 7/2005 | Theeuwes et al. |
| 6,923,764 B2 | 8/2005 | Aceti et al. |
| 6,931,277 B1 | 8/2005 | Yuzhakov et al. |
| 6,940,591 B2 | 9/2005 | Sopp et al. |
| 6,952,604 B2 | 10/2005 | DeNuzzio et al. |
| 6,969,359 B2 | 11/2005 | Duchon et al. |
| 6,990,367 B2 | 1/2006 | Kiser et al. |
| 6,997,886 B2 | 2/2006 | Latterell et al. |
| 7,001,343 B2 | 2/2006 | Erickson et al. |
| 7,001,344 B2 | 2/2006 | Freeman et al. |
| 7,004,928 B2 | 2/2006 | Aceti et al. |
| 7,008,384 B2 | 3/2006 | Tapper |
| 7,014,615 B2 | 3/2006 | Erickson et al. |
| 7,037,277 B1 | 5/2006 | Smith et al. |
| 7,041,067 B2 | 5/2006 | Sopp et al. |
| 7,041,068 B2 | 5/2006 | Freeman et al. |
| 7,047,070 B2 | 5/2006 | Wilkinson et al. |
| 7,066,586 B2 | 6/2006 | da Silva |
| 7,066,885 B2 | 6/2006 | Erickson et al. |
| 7,097,631 B2 | 8/2006 | Trautman et al. |
| 7,133,717 B2 | 11/2006 | Coston et al. |
| 7,137,957 B2 | 11/2006 | Erickson et al. |
| 7,150,755 B2 | 12/2006 | Levaughn et al. |
| 7,174,199 B2 | 2/2007 | Berner et al. |
| 7,182,910 B2 | 2/2007 | Allen et al. |
| 7,235,056 B2 | 6/2007 | Duchon et al. |
| 7,247,144 B2 | 7/2007 | Douglas et al. |
| 7,264,627 B2 | 9/2007 | Perez |
| 7,316,671 B2 | 1/2008 | Lastovich et al. |
| 7,335,166 B2 | 2/2008 | Faupel et al. |
| 7,344,499 B1 | 3/2008 | Prausnitz et al. |
| 7,344,587 B2 | 3/2008 | Khan et al. |
| 7,374,545 B2 | 5/2008 | Alroy |
| 7,374,949 B2 | 5/2008 | Kuriger |
| 7,402,441 B2 | 7/2008 | Lowe et al. |
| 7,413,868 B2 | 8/2008 | Kauvar et al. |
| 7,422,567 B2 | 9/2008 | Lastovich et al. |
| 7,429,258 B2 | 9/2008 | Angel et al. |
| 7,537,590 B2 | 5/2009 | Santini et al. |
| 7,544,185 B2 | 6/2009 | Bengtsson |
| 7,575,717 B2 | 8/2009 | Cooke et al. |
| 7,585,278 B2 | 9/2009 | Aceti et al. |
| 7,585,412 B2 | 9/2009 | Gorsuch et al. |
| 7,631,760 B2 | 12/2009 | Guelzow et al. |
| 7,758,518 B2 | 7/2010 | Perez et al. |
| 7,767,017 B2 | 8/2010 | Lahann et al. |
| 7,811,302 B2 | 10/2010 | Steg |
| 7,883,473 B2 | 2/2011 | LeVaughn et al. |
| 7,896,830 B2 | 3/2011 | Gura et al. |
| 7,942,827 B2 | 5/2011 | Mir et al. |
| 7,947,772 B2 | 5/2011 | Lahann |
| 8,043,480 B2 | 10/2011 | Lahann et al. |
| 8,052,849 B2 | 11/2011 | Lahann et al. |
| 8,075,826 B2 | 12/2011 | Lastovich et al. |
| 8,133,191 B2 | 3/2012 | Rosenberg et al. |
| 8,187,708 B2 | 5/2012 | Lahann et al. |
| 8,202,240 B2 | 6/2012 | Felt et al. |
| 8,241,651 B2 | 8/2012 | Lahann |
| 8,246,582 B2 | 8/2012 | Angel et al. |
| 8,344,028 B2 | 1/2013 | Xu et al. |
| 8,523,894 B2 | 9/2013 | Schmelzeisen-Redeker et al. |
| 8,561,795 B2 | 10/2013 | Schott |
| 8,808,202 B2 | 8/2014 | Brancazio |
| 8,821,412 B2 | 9/2014 | Gonzalez-Zugasti et al. |
| 8,827,971 B2 | 9/2014 | Chickering, III et al. |
| 8,900,180 B2 | 12/2014 | Wolter et al. |
| 2001/0005772 A1 | 6/2001 | Kisakibaru |
| 2002/0010414 A1 | 1/2002 | Coston et al. |
| 2002/0013538 A1 | 1/2002 | Teller |
| 2002/0065453 A1 | 5/2002 | Lesho et al. |
| 2002/0077584 A1 | 6/2002 | Lin et al. |
| 2002/0082543 A1 | 6/2002 | Park et al. |
| 2002/0099308 A1 | 7/2002 | Bojan et al. |
| 2002/0099356 A1 | 7/2002 | Unger et al. |
| 2002/0115967 A1 | 8/2002 | Svedman |
| 2002/0119136 A1 | 8/2002 | Johansen |
| 2002/0130042 A1 | 9/2002 | Moerman et al. |
| 2002/0138049 A1 | 9/2002 | Allen |
| 2002/0168290 A1 | 11/2002 | Yuzhakov et al. |
| 2002/0169393 A1 | 11/2002 | Cunningham et al. |
| 2002/0169394 A1 | 11/2002 | Eppstein et al. |
| 2002/0169411 A1 | 11/2002 | Sherman et al. |
| 2002/0187556 A1 | 12/2002 | Shartle et al. |
| 2002/0188221 A1 | 12/2002 | Sohrab |

(56) References Cited

U.S. PATENT DOCUMENTS

| | | |
|---|---|---|
| 2003/0040682 A1 | 2/2003 | Tapper |
| 2003/0055326 A1 | 3/2003 | Sohrab |
| 2003/0083645 A1 | 5/2003 | Angel et al. |
| 2003/0083685 A1 | 5/2003 | Freeman et al. |
| 2003/0100846 A1 | 5/2003 | Custer et al. |
| 2003/0109807 A1 | 6/2003 | Knoll |
| 2003/0113540 A1 | 6/2003 | Anderson et al. |
| 2003/0135158 A1 | 7/2003 | Gonnelli |
| 2003/0135167 A1 | 7/2003 | Gonnelli |
| 2003/0135201 A1 | 7/2003 | Gonnelli |
| 2003/0135333 A1 | 7/2003 | Aceti et al. |
| 2003/0143746 A1 | 7/2003 | Sage |
| 2003/0159615 A1 | 8/2003 | Anderson et al. |
| 2003/0162304 A1 | 8/2003 | Dority et al. |
| 2003/0181863 A1 | 9/2003 | Ackley et al. |
| 2003/0187394 A1 | 10/2003 | Wilkinson et al. |
| 2003/0187395 A1 | 10/2003 | Gabel et al. |
| 2003/0195398 A1* | 10/2003 | Suzuki et al. ............... 600/300 |
| 2003/0204148 A1 | 10/2003 | Lange et al. |
| 2003/0208138 A1 | 11/2003 | Olson |
| 2003/0212344 A1 | 11/2003 | Yuzhakov et al. |
| 2003/0212345 A1 | 11/2003 | McAllister et al. |
| 2003/0212347 A1 | 11/2003 | Sohrab |
| 2003/0212423 A1 | 11/2003 | Pugh et al. |
| 2003/0228367 A1 | 12/2003 | Mathiowitz et al. |
| 2004/0010207 A1 | 1/2004 | Flaherty et al. |
| 2004/0058458 A1 | 3/2004 | Anker et al. |
| 2004/0096959 A1 | 5/2004 | Stiene et al. |
| 2004/0098009 A1 | 5/2004 | Boecker et al. |
| 2004/0106904 A1 | 6/2004 | Gonnelli et al. |
| 2004/0171980 A1 | 9/2004 | Mitragotri et al. |
| 2004/0199103 A1 | 10/2004 | Kwon |
| 2004/0204744 A1 | 10/2004 | Penner et al. |
| 2004/0236250 A1 | 11/2004 | Hodges et al. |
| 2004/0247016 A1 | 12/2004 | Faries et al. |
| 2004/0249310 A1 | 12/2004 | Shartle et al. |
| 2004/0253185 A1 | 12/2004 | Herweck et al. |
| 2005/0015055 A1 | 1/2005 | Yang |
| 2005/0019902 A1 | 1/2005 | Mathies et al. |
| 2005/0027176 A1 | 2/2005 | Xie |
| 2005/0027308 A1 | 2/2005 | Davis et al. |
| 2005/0038669 A1 | 2/2005 | Sachdeva et al. |
| 2005/0054907 A1 | 3/2005 | Page et al. |
| 2005/0064529 A1 | 3/2005 | Kwon |
| 2005/0069925 A1 | 3/2005 | Ford et al. |
| 2005/0070819 A1 | 3/2005 | Poux et al. |
| 2005/0085838 A1 | 4/2005 | Thompson et al. |
| 2005/0106066 A1 | 5/2005 | Saltsman et al. |
| 2005/0106713 A1 | 5/2005 | Phan et al. |
| 2005/0137481 A1 | 6/2005 | Sheard et al. |
| 2005/0137531 A1 | 6/2005 | Prausnitz et al. |
| 2005/0137536 A1 | 6/2005 | Gonnelli |
| 2005/0172852 A1 | 8/2005 | Anderson et al. |
| 2005/0182307 A1 | 8/2005 | Currie et al. |
| 2005/0196747 A1 | 9/2005 | Stiene |
| 2005/0201974 A1 | 9/2005 | Schestopol et al. |
| 2005/0203360 A1* | 9/2005 | Brauker et al. ............... 600/345 |
| 2005/0215923 A1 | 9/2005 | Wiegel |
| 2005/0221276 A1 | 10/2005 | Rozakis et al. |
| 2005/0228313 A1 | 10/2005 | Kaler et al. |
| 2005/0245844 A1 | 11/2005 | Mace et al. |
| 2005/0249672 A1 | 11/2005 | Bolbot |
| 2005/0251152 A1 | 11/2005 | Herweck et al. |
| 2005/0261632 A1 | 11/2005 | Xu |
| 2005/0261639 A1 | 11/2005 | Herweck |
| 2006/0001551 A1 | 1/2006 | Kraft et al. |
| 2006/0004271 A1 | 1/2006 | Peyser et al. |
| 2006/0004303 A1 | 1/2006 | Weidenhaupt et al. |
| 2006/0030790 A1 | 2/2006 | Braig et al. |
| 2006/0036187 A1 | 2/2006 | Vos et al. |
| 2006/0058602 A1 | 3/2006 | Kwiatkowski et al. |
| 2006/0142651 A1 | 6/2006 | Brister et al. |
| 2006/0200046 A1 | 9/2006 | Windus-Smith et al. |
| 2006/0228259 A1 | 10/2006 | Samsoondar |
| 2006/0258959 A1 | 11/2006 | Sode |
| 2006/0264779 A1 | 11/2006 | Kemp et al. |
| 2006/0264782 A1 | 11/2006 | Holmes et al. |
| 2007/0004989 A1 | 1/2007 | Dhillon |
| 2007/0016446 A1* | 1/2007 | Brown ............... 600/300 |
| 2007/0016926 A1 | 1/2007 | Ward et al. |
| 2007/0027427 A1 | 2/2007 | Trautman et al. |
| 2007/0031283 A1 | 2/2007 | Davis et al. |
| 2007/0036686 A1 | 2/2007 | Hatamian et al. |
| 2007/0046476 A1 | 3/2007 | Hinkamp |
| 2007/0054119 A1 | 3/2007 | Garstecki et al. |
| 2007/0066934 A1 | 3/2007 | Etheredge et al. |
| 2007/0078414 A1 | 4/2007 | McAllister et al. |
| 2007/0092637 A1 | 4/2007 | Brown et al. |
| 2007/0100219 A1 | 5/2007 | Sweitzer et al. |
| 2007/0105176 A1 | 5/2007 | Ibey et al. |
| 2007/0112180 A1 | 5/2007 | Gray et al. |
| 2007/0123801 A1 | 5/2007 | Goldberger et al. |
| 2007/0129618 A1* | 6/2007 | Goldberger et al. ............ 600/345 |
| 2007/0161964 A1 | 7/2007 | Yuzhakov |
| 2007/0167340 A1 | 7/2007 | Barthel et al. |
| 2007/0173740 A1 | 7/2007 | Chan et al. |
| 2007/0179404 A1 | 8/2007 | Escutia et al. |
| 2007/0185432 A1 | 8/2007 | Etheredge et al. |
| 2007/0208275 A1 | 9/2007 | Vinogradov et al. |
| 2007/0213638 A1 | 9/2007 | Herbrechtsmeier et al. |
| 2007/0225676 A1 | 9/2007 | Prausnitz et al. |
| 2007/0231355 A1 | 10/2007 | Quadir et al. |
| 2007/0232956 A1 | 10/2007 | Harman et al. |
| 2007/0233199 A1 | 10/2007 | Moore et al. |
| 2007/0237800 A1 | 10/2007 | Lahann |
| 2007/0238943 A1 | 10/2007 | Poulsen et al. |
| 2007/0249962 A1 | 10/2007 | Alden et al. |
| 2008/0014627 A1 | 1/2008 | Merchant et al. |
| 2008/0051689 A1 | 2/2008 | Gura et al. |
| 2008/0077430 A1* | 3/2008 | Singer et al. ............... 600/300 |
| 2008/0081695 A1 | 4/2008 | Patchen |
| 2008/0086051 A1 | 4/2008 | Voegele |
| 2008/0099478 A1 | 5/2008 | Gleich |
| 2008/0112886 A1 | 5/2008 | Mitragotri et al. |
| 2008/0125673 A1 | 5/2008 | Carano et al. |
| 2008/0125743 A1 | 5/2008 | Yuzhakov |
| 2008/0129486 A1 | 6/2008 | Jeckelman et al. |
| 2008/0140049 A1 | 6/2008 | Kirby |
| 2008/0154107 A1 | 6/2008 | Jina |
| 2008/0167535 A1 | 7/2008 | Stivoric et al. |
| 2008/0167613 A1 | 7/2008 | Khouri et al. |
| 2008/0183144 A1 | 7/2008 | Trautmann et al. |
| 2008/0200838 A1 | 8/2008 | Goldberger et al. |
| 2008/0220411 A1 | 9/2008 | McNaughton et al. |
| 2008/0221407 A1 | 9/2008 | Baker |
| 2008/0269666 A1 | 10/2008 | Wang et al. |
| 2008/0275327 A1 | 11/2008 | Faarbaek et al. |
| 2008/0281290 A1 | 11/2008 | Yodfat et al. |
| 2008/0300508 A1 | 12/2008 | Tomer |
| 2008/0319347 A1 | 12/2008 | Keren |
| 2009/0036795 A1 | 2/2009 | Duineveld et al. |
| 2009/0043250 A1 | 2/2009 | Gonnelli |
| 2009/0054813 A1 | 2/2009 | Freeman et al. |
| 2009/0099478 A1 | 4/2009 | Cassells et al. |
| 2009/0099529 A1 | 4/2009 | Anderson et al. |
| 2009/0105614 A1 | 4/2009 | Momose et al. |
| 2009/0124994 A1 | 5/2009 | Roe |
| 2009/0182306 A1 | 7/2009 | Lee et al. |
| 2009/0187160 A1 | 7/2009 | McAllister et al. |
| 2009/0198189 A1 | 8/2009 | Simons et al. |
| 2009/0198215 A1 | 8/2009 | Chong et al. |
| 2009/0215159 A1 | 8/2009 | Kirby |
| 2009/0216103 A1 | 8/2009 | Brister et al. |
| 2009/0216629 A1* | 8/2009 | James et al. ............... 705/14 |
| 2009/0264720 A1 | 10/2009 | Torjman et al. |
| 2009/0270792 A1 | 10/2009 | Lastovich et al. |
| 2009/0318779 A1 | 12/2009 | Tran |
| 2009/0318846 A1 | 12/2009 | Prausnitz et al. |
| 2010/0010374 A1 | 1/2010 | Escutia et al. |
| 2010/0042137 A1 | 2/2010 | Oronsky et al. |
| 2010/0049126 A1 | 2/2010 | Bronfeld et al. |
| 2010/0069726 A1 | 3/2010 | Levinson |
| 2010/0069730 A1 | 3/2010 | Bergstrom et al. |
| 2010/0094170 A1 | 4/2010 | Wilson et al. |

(56) References Cited

U.S. PATENT DOCUMENTS

| | | |
|---|---|---|
| 2010/0111970 A1 | 5/2010 | Pons et al. |
| 2010/0121368 A1 | 5/2010 | Kim et al. |
| 2010/0147763 A1 | 6/2010 | Tsou et al. |
| 2010/0160894 A1 | 6/2010 | Julian et al. |
| 2010/0210970 A1 | 8/2010 | Horikawa et al. |
| 2010/0222703 A1 | 9/2010 | Takashima et al. |
| 2010/0234768 A1 | 9/2010 | Uchiyama et al. |
| 2010/0249560 A1 | 9/2010 | Levinson et al. |
| 2010/0256465 A1 | 10/2010 | Bernstein et al. |
| 2010/0256524 A1 | 10/2010 | Levinson et al. |
| 2010/0261988 A1 | 10/2010 | Tamir |
| 2010/0269837 A1 | 10/2010 | Levinson et al. |
| 2010/0272652 A1 | 10/2010 | Levinson |
| 2010/0292191 A1 | 11/2010 | Mainx et al. |
| 2010/0324449 A1 | 12/2010 | Rostaing et al. |
| 2010/0324451 A1 | 12/2010 | Ishibashi et al. |
| 2011/0003770 A1 | 1/2011 | Eek |
| 2011/0009847 A1 | 1/2011 | Levinson et al. |
| 2011/0105828 A1 | 5/2011 | Perless et al. |
| 2011/0105872 A1 | 5/2011 | Chickering, III et al. |
| 2011/0105951 A1 | 5/2011 | Bernstein et al. |
| 2011/0105952 A1 | 5/2011 | Bernstein et al. |
| 2011/0125058 A1 | 5/2011 | Levinson et al. |
| 2011/0172508 A1 | 7/2011 | Chickering, III et al. |
| 2011/0172510 A1 | 7/2011 | Chickering, III et al. |
| 2011/0245708 A1 | 10/2011 | Finkel et al. |
| 2011/0251562 A1 | 10/2011 | Chickering, III et al. |
| 2011/0276027 A1 | 11/2011 | Trautman et al. |
| 2011/0288389 A9 | 11/2011 | Levinson et al. |
| 2011/0306853 A1 | 12/2011 | Black et al. |
| 2012/0010529 A1 | 1/2012 | Chickering, III et al. |
| 2012/0016308 A1 | 1/2012 | Schott |
| 2012/0039809 A1 | 2/2012 | Levinson et al. |
| 2012/0041338 A1 | 2/2012 | Chickering et al. |
| 2012/0123297 A1 | 5/2012 | Brancazio |
| 2012/0271125 A1 | 10/2012 | Bernstein et al. |
| 2012/0275955 A1 | 11/2012 | Haghgooie et al. |
| 2012/0277629 A1 | 11/2012 | Bernstein et al. |
| 2012/0277696 A1 | 11/2012 | Gonzalez-Zugasti et al. |
| 2012/0277697 A1 | 11/2012 | Haghgooie et al. |
| 2012/0315271 A1 | 12/2012 | Shelton et al. |
| 2013/0018279 A1 | 1/2013 | Plante et al. |
| 2013/0079666 A1 | 3/2013 | Gonzalez-Zugasti et al. |
| 2013/0081960 A1 | 4/2013 | Schott |
| 2013/0138058 A9 | 5/2013 | Chickering, III et al. |
| 2013/0158468 A1 | 6/2013 | Bernstein et al. |
| 2013/0158482 A1 | 6/2013 | Davis et al. |
| 2014/0336536 A1 | 11/2014 | Brancazio |

FOREIGN PATENT DOCUMENTS

| | | |
|---|---|---|
| CN | 1753646 A | 3/2006 |
| DE | 198 33 868 A1 | 5/2000 |
| DE | 20 2008 010918 U1 | 12/2008 |
| EP | 0 043 738 A2 | 1/1982 |
| EP | 0 115 388 A1 | 8/1984 |
| EP | 0 250 693 A1 | 1/1988 |
| EP | 0 365 196 A2 | 4/1990 |
| EP | 0 555 554 A1 | 8/1993 |
| EP | 0 803 288 A2 | 10/1997 |
| EP | 0 838 232 A2 | 4/1998 |
| EP | 0 977 032 A1 | 2/2000 |
| EP | 1 360 934 A1 | 11/2003 |
| EP | 1 437 093 A1 | 7/2004 |
| EP | 1 470 781 A2 | 10/2004 |
| EP | 1 491 143 A1 | 12/2004 |
| EP | 1 522 260 A1 | 4/2005 |
| EP | 1 611 837 A2 | 1/2006 |
| EP | 1 639 938 A1 | 3/2006 |
| EP | 1 652 551 A2 | 5/2006 |
| EP | 1 834 589 A2 | 9/2007 |
| EP | 1 844 710 B1 | 10/2007 |
| EP | 1 997 431 A1 | 12/2008 |
| EP | 2 064 993 A1 | 6/2009 |
| EP | 2 077 128 A1 | 7/2009 |
| GB | 2153223 A | 8/1985 |
| JP | 63-108264 | 5/1988 |
| JP | 5-63506 | 8/1993 |
| JP | 7-255706 | 10/1995 |
| JP | 2000-116629 | 4/2000 |
| JP | 2002-272710 | 9/2002 |
| JP | 2004-8413 | 1/2004 |
| JP | 2004-532079 A | 10/2004 |
| JP | 2005-011364 A | 1/2005 |
| JP | 2005-211189 | 8/2005 |
| JP | 2005-525141 | 8/2005 |
| JP | 2006-15148 | 1/2006 |
| JP | 2006-109894 | 4/2006 |
| JP | 2006-521555 | 9/2006 |
| JP | 2007-209747 | 8/2007 |
| JP | 2008-099992 | 5/2008 |
| JP | 2009-504273 | 2/2009 |
| WO | WO 92/02175 A1 | 2/1992 |
| WO | WO 95/10223 A2 | 4/1995 |
| WO | WO 95/15783 A1 | 6/1995 |
| WO | WO 97/08987 A1 | 3/1997 |
| WO | WO 97/10745 A1 | 3/1997 |
| WO | WO 97/34587 A2 | 9/1997 |
| WO | WO 97/48442 A1 | 12/1997 |
| WO | WO 98/24366 A2 | 6/1998 |
| WO | WO 99/27852 A1 | 6/1999 |
| WO | WO 00/35357 A1 | 6/2000 |
| WO | WO 00/35530 A1 | 6/2000 |
| WO | WO 00/74763 A2 | 12/2000 |
| WO | WO 01/43643 A1 | 6/2001 |
| WO | WO 01/93946 A1 | 12/2001 |
| WO | WO 02/00101 A2 | 1/2002 |
| WO | WO 02/05890 A2 | 1/2002 |
| WO | WO 02/30506 A2 | 4/2002 |
| WO | WO 02/078533 A2 | 10/2002 |
| WO | WO 02/091922 A1 | 11/2002 |
| WO | WO 02/100253 A2 | 12/2002 |
| WO | WO 03/020134 A2 | 3/2003 |
| WO | WO 03/026611 A2 | 4/2003 |
| WO | WO 03/030984 A2 | 4/2003 |
| WO | WO 03/037407 A1 | 5/2003 |
| WO | WO 03/039632 A2 | 5/2003 |
| WO | WO 03/070099 A1 | 8/2003 |
| WO | WO 03/082091 A2 | 10/2003 |
| WO | WO 03/088851 A1 | 10/2003 |
| WO | WO 03/099123 A1 | 12/2003 |
| WO | WO 2004/006928 A1 | 1/2004 |
| WO | WO 2004/006982 A3 | 1/2004 |
| WO | WO 2004/022133 A2 | 3/2004 |
| WO | WO 2004/085995 A2 | 10/2004 |
| WO | WO 2005/000118 A1 | 1/2005 |
| WO | WO 2005/023111 A3 | 3/2005 |
| WO | WO 2005/025413 A2 | 3/2005 |
| WO | WO 2005/084534 A1 | 9/2005 |
| WO | WO 2005/107594 A2 | 11/2005 |
| WO | WO 2005/123173 A1 | 12/2005 |
| WO | WO 2006/003403 A1 | 1/2006 |
| WO | WO 2006/019823 A2 | 2/2006 |
| WO | WO 2006/027586 A1 | 3/2006 |
| WO | WO 2006/111741 A1 | 10/2006 |
| WO | WO 2006/121510 A2 | 11/2006 |
| WO | WO 2006/128034 A1 | 11/2006 |
| WO | WO 2007/002521 A2 | 1/2007 |
| WO | WO 2007/002522 A1 | 1/2007 |
| WO | WO 2007/021979 A2 | 2/2007 |
| WO | WO 2007/079530 A1 | 7/2007 |
| WO | WO 2007/097754 A1 | 8/2007 |
| WO | WO 2007/108519 A1 | 9/2007 |
| WO | WO 2007/108987 A2 | 9/2007 |
| WO | WO 2007/115291 A2 | 10/2007 |
| WO | WO 2008/016646 A2 | 2/2008 |
| WO | WO 2008/031035 A2 | 3/2008 |
| WO | WO 2008/043156 A1 | 4/2008 |
| WO | WO 2008/052034 A1 | 5/2008 |
| WO | WO 2008/081444 A2 | 7/2008 |
| WO | WO 2008/153930 A1 | 12/2008 |
| WO | WO 2009/004627 A2 | 1/2009 |
| WO | WO 2009/055693 A2 | 4/2009 |

(56) References Cited

FOREIGN PATENT DOCUMENTS

| | | |
|---|---|---|
| WO | WO 2009/071775 A1 | 6/2009 |
| WO | WO 2009/104765 A1 | 8/2009 |
| WO | WO 2009/107135 A2 | 9/2009 |
| WO | WO 2009/126653 A1 | 10/2009 |
| WO | WO 2009/149308 A2 | 12/2009 |
| WO | WO 2009/151421 A1 | 12/2009 |
| WO | WO 2010/011641 A2 | 1/2010 |
| WO | WO 2010/101620 A2 | 9/2010 |
| WO | WO 2010/101621 A1 | 9/2010 |
| WO | WO 2010/101625 A2 | 9/2010 |
| WO | WO 2010/110916 A2 | 9/2010 |
| WO | WO 2011/016019 A1 | 2/2011 |
| WO | WO 2011/053796 A2 | 5/2011 |
| WO | WO 2011/065972 A2 | 6/2011 |
| WO | WO 2011/088214 A2 | 7/2011 |
| WO | WO 2012/064802 A1 | 5/2012 |

OTHER PUBLICATIONS

International Preliminary Report on Patentability for PCT/US2009/046333 mailed Aug. 31, 2010.
International Search Report and Written Opinion for PCT/US2010/000623 mailed Sep. 22, 2010.
International Search Report and Written Opinion for PCT/US2010/000624 mailed Aug. 18, 2010.
International Search Report and Written Opinion for PCT/US2010/054741 mailed Apr. 27, 2011.
International Search Report and Written Opinion for PCT/US2010/000631 mailed Aug. 4, 2010.
[No Author Listed] Sof-Tact Manual. Date Unknown. 57 pages.
Angell et al., Silicon Micromechanical Devices. Scientific American. 1983;248:44-55.
Aungst et al., Contributions of drug solubilization, partitioning, barrier disruption, and solvent permeation to the enhancement of skin permeation of various compounds with fatty acids and amines. Pharm Res. Jul. 1990; 7(7):712-8.
Baroli, Penetration of metallic nanoparticles in human full-thickness skin. J Ind Derm. 2007;127:1701-12.
Bina et al., Clinical impact of prandial state, exercise, and site preparation on the equivalence of alternative-site blood glucose testing. Diabetes Care. Apr. 2003;26(4):981-5.
Brown, Encapsulation of glucose oxidase and an oxygen-quenched fluorophore in polyelectrolyte-coated calcium alginate microspheres as optical glucose sensor systems. Biosens Bioelec. 2005;21:212-16.
Cormier et al., Transdermal delivery of desmopressin using a coated microneedle array patch system. J Control Release. Jul 7, 2004;97(3):503-11.
Duffy et al., Rapid Prototyping of Microfluidic Systems and Polydimethylsiloxane. Anal Chem. 1998;70:4974-84.
Elias, The Microscopic Structure of the Epidermis and Its Derivatives. In: Percutaneous Absorption—Mechanisms—Methodology. Bronaugh et al., eds. Marcell Dekker. 1989;3-12.
Fineberg et al., Use of an automated device for alternative site blood glucose monitoring. Diabetes Care. Jul. 2001;24(7):1217-20.
Gomes et al., Evaluation of nanoparticles loaded with benzopsoralen in rat peritoneal exudate cells. Int J Pharm. Mar. 6, 2007;332(1-2):153-60. Epub Sep. 27, 2006.
Kost et al., Chapter 4. Ultrasound-Mediated Transdermal Drug Delivery. In: Topical Drug Bioavailability Bioequivalance, and Penetration. Shah et al., eds. Plennum, NY. 1993:91-104.
Matriano et al., Macroflux microprojection array patch technology: a new and efficient approach for intracutaneous immunization. Pharm Res. Jan. 2002;19(1):63-70.
McShane, Microcapsules as "smart tattoo" glucose sensors: engineering systems with enzymes and glucose-binding sensing elements. In: Top Fluor Spec Glc. Sens. 2006.;11:131-63.
Mitragotri et al., Sonophoresis: Enhanced Transdermal Drug Delivery by Application of Ultrasound. In: Encl of Pharm Tech. Swarbrick et al., eds.1996;14:103-22.
Rousche et al., A method for pneumatically inserting an array of penetrating electrodes into cortical tissue. Annals of Biomedical Engineering. 1992;20(4):413-22.
Rousche et al., A System for Impact Insertion of a 100 Electrode Array into Cortical Tissue. Annual Intl Conf IEEE Engineer Med Biol Soc. 1990;12(2):O494-95.
Rouse, Effects of mechanical flexion on the penetration of fullerene amino acid-derivatized peptide nanoparticles through skin. Nano-Lett. 2007;7(1): 155-60.
Suk et al., Gene delivery to differentiated neurotypic cells with RGD and HIV Tat peptide functionalized polymeric nanoparticles. Biomaterials. Oct. 2006;27(29):5143-50.
Uhrich et al., Polymeric systems for controlled drug release. Chem. Rev. 1999:99:3181-98.
Verbaan et al., Improved piercing of microneedle arrays in dermatomed human skin by an impact insertion method. J Control Release. May 22, 2008;128(1):80-8. Epub Feb. 26, 2008.
Whitesides et al., Soft lithography in biology and biochemistry. Annu Rev Biomed Eng. 2001;3:335-73.
Xia et al., Soft Lithography. Ann Rev Mater Sci. 1998;28:153-84.
International Search Report and Written Opinion for PCT/US2010/000630 mailed Jun. 16, 2011.
Invitation to Restrict or Pay Additional Fees, and Where Applicable, Protest Fees for PCT/US2010/000624 mailed Jun. 20, 2011.
International Search Report and Written for PCT/US2010/054723 mailed Jul. 12, 2011.
International Search Report and Written Opinion for PCT/US2010/054725 mailed Jun. 8, 2011.
International Search Report and Written Opinion for PCT/US2011/022967 mailed Jul. 7, 2011.
International Search Report and Written Opinion for PCT/US2010/003045 mailed Jul. 27, 2011.
Invitation to Restrict or Pay Additional Fees, and Where Applicable, Protest Fees for PCT/US2010/000631 mailed Jun. 20, 2011.
International Preliminary Report on Patentability for PCT/US2010/000624 mailed Aug. 5, 2011.
International Preliminary Report on Patentability for PCT/US2010/054723 mailed May 10, 2012.
International Preliminary Report on Patentability for PCT/US2010/054741 mailed May 10, 2012.
International Preliminary Report on Patentability for PCT/US2010/054725 mailed May 10, 2012.
International Preliminary Report on Patentability for PCT/US2011/022967 mailed Aug. 9, 2012.
International Preliminary Report on Patentability for PCT/US2010/003045 mailed Jun. 7, 2012.
International Search Report and Written Opinion for PCT/US2011/021134 mailed Oct. 27, 2011.
International Preliminary Report on Patentabiltiy for PCT/US2011/021134 mailed Jul. 26, 2012.
International Preliminary Report on Patentability for PCT/US2010/000631 mailed Aug. 5, 2011.
Invitation to Pay Additional Fees for PCT/US2011/041430 mailed Nov. 4, 2011.
International Search Report and Written Opinion for PCT/US2011/041430 mailed Jan. 31, 2012.
International Preliminary Report on Patentability for PCT/US2011/041430 mailed Jan. 10, 2013.
International Search Report and Written Opinion for PCT/US2011/043698 mailed Feb. 23, 2012.
International Preliminary Report on Patentability for PCT/US2011/043698 mailed Feb. 7, 2013.
International Search Report and Written Opinion for PCT/US2011/044145 mailed Dec. 2, 2011.
International Preliminary Report on Patentability for PCT/US2011/044145 mailed Jan. 31, 2013.
Invitation to Pay Additional Fee for PCT/US2011/047565 mailed Dec. 2, 2011.
International Search Report and Written Opinion for PCT/US2011/047565 mailed Mar. 9, 2012.
International Preliminary Report on Patentability for PCT/US2011/047565 mailed Feb. 28, 2013.

(56) References Cited

OTHER PUBLICATIONS

International Search Report and Written Opinion for PCT/US2011/047581 mailed Mar. 28, 2012.
International Preliminary Report on Patentability for PCT/US2011/047581 mailed Feb. 28, 2013.
International Search Report and Written Opinion for PCT/US2011/059876 mailed Feb. 22, 2012.
International Preliminary Report mailed May 23, 2013 for PCT/US2011/059876.
International Search Report and Written Opinion for PCT/US2011/021131 mailed Sep. 30, 2011.
International Preliminary Report on Patentabiltiy for PCT/US2011/021131 mailed Jul. 26, 2012.
Invitation to Pay Additional Fees mailed Aug. 17, 2012 in connection with PCT/US2012/035191.
International Search Report and Written Opinion mailed Oct. 4, 2012 in connection with PCT/U52012/035191.
International Preliminary Report on Patentabiltiy for PCT/US2012/035191 mailed Nov. 7, 2013.
Invitation to Pay Additional Fees mailed Aug. 17, 2012 in connection with PCT/US2012/035207.
International Search Report and Written Opinion mailed Oct. 4, 2012 in connection with PCT/U52012/035207.
International Preliminary Report on Patentabiltiy for PCT/US2012/035207 mailed Nov. 7, 2013.
International Search Report and Written Opinion for PCT/US2012/035152 mailed Aug. 17, 2012.
International Preliminary Report on Patentabiltiy for PCT/US2012/035152 mailed Nov. 7, 2013.
International Search Report and Written Opinion for PCT/US2012/032846 mailed Jul. 23, 2012.
International Preliminary Report on Patentabiltiy for PCT/US2012/032846 mailed Oct. 24, 2013.
Invitation to Pay Additional Fees mailed Aug. 17, 2012 in connection with PCT/US2012/035173.
International Search Report and Written Opinion mailed Oct. 4, 2012 in connection with PCT/U52012/035173.
European Search Report mailed Jan. 8, 2013 for Application No. 09759467.5.
Office Action mailed Dec. 7, 2012 for U.S. Appl. No. 12/478,756.
Office Action mailed Mar. 26, 2012 for U.S. Appl. No. 12/716,233.
Office Action mailed Jun. 21, 2012 for U.S. Appl. No. 12/716,229.
Office Action mailed May 14, 2013 for U.S. Appl. No. 12/716,229.
Office Action mailed Apr. 30, 2013 for U.S. Appl. No. 12/915,735.
European Office Action mailed Apr. 11, 2013 for Application No. 10777165.1.
Office Action mailed Nov. 1, 2012 for U.S. Appl. No. 12/915,789.
Office Action mailed Aug. 30, 2013 for U.S. Appl. No. 12/915,789.
Chinese Office Action mailed Jun. 9, 2013 for Application No. 201080055393.6 and English translation thereof.
European Office Action mailed Aug. 14, 2013 for Application No. 10776881.4.
Office Action mailed Nov. 1, 2012 for U.S. Appl. No. 12/915,820.
Office Action mailed May 30, 2013 for U.S. Appl. No. 12/915,820.
Office Action mailed Apr. 20, 2012 in connection with U.S. Appl. No. 12/953,744.
Office Action mailed Aug. 23, 2012 in connection with U.S. Appl. No. 12/953,744.
Office Action mailed Apr. 26, 2013 in connection with U.S. Appl. No. 12/953,744.
Office Action mailed Dec. 28, 2012 for U.S. Appl. No. 13/166,611.
Office Action mailed Aug. 8, 2013 for U.S. Appl. No. 13/166,611.
Chinese Office Action mailed Jun. 4, 2013 for Application No. 201080017375.9 and English translation thereof.
European Office Action mailed May 8, 2013 for Application No. 10708434.5.
Office Action mailed Dec. 22, 2011 in connection with U.S. Appl. No. 12/716,226.
Office Action mailed Jun. 20, 2012 in connection with U.S. Appl. No. 12/716,226.

Office Action mailed Jan. 31, 2013 for U.S. Appl. No. 13/166,451.
Office Action mailed Aug. 8, 2013 for U.S. Appl. No. 13/166,451.
Office Action mailed May 17, 2013 for U.S. Appl. No. 13/678,316.
Office Action mailed Apr. 9, 2013 for U.S. Appl. No. 13/208,770.
Office Action mailed Nov. 14, 2013 for U.S. Appl. No. 13/208,770.
Office Action mailed Sep. 11, 2013 for U.S. Appl. No. 13/208,808.
Office Action mailed Aug. 8, 2013 for U.S. Appl. No. 13/292,254.
European Office Action mailed Sep. 2, 2013 for Application No. 11700780.7.
Office Action mailed May 7, 2013 for U.S. Appl. No. 13/680,351.
Office Action mailed Sep. 27, 2013 for U.S. Appl. No. 13/680,351.
Office Action mailed Oct. 10, 2013 for U.S. Appl. No. 13/680,351.
Office Action mailed Jul. 18, 2013 for U.S. Appl. No. 13/456,394.
Office Action mailed Jul. 9, 2013 for U.S. Appl. No. 13/456,505.
[No Author Listed] Greiner Bio-One Preanalytics Catalogue. www.gbo.com/preanalytics. Feb. 2012. 39 pages.
[No Author Listed] Safe-T-Fill®: 100% Plastic Capillary Blood Collection Systems. RAM Scientific. [Month of publication not listed on copy] 2003. Last accessed Jun. 28, 2012 at http//www.ramsci.com.
Chinese Office Action mailed Nov. 28, 2013 for Application No. 201080017376.3 and English translation thereof.
European Office Action mailed Nov. 26, 2013 for Application No. 10708432.9.
Japanese Office Action mailed May 27, 2014 for Application No. 2011-552935.
Office Action mailed Dec. 30, 2013 for U.S. Appl. No. 12/716,229.
Office Action mailed Jan. 15, 2014 for U.S. Appl. No. 12/915,735.
European Office Action mailed May 19, 2014 for Application No. 10777165.1.
Office Action mailed Jun. 18, 2014 for U.S. Appl. No. 12/915,789.
Chinese Office Action mailed Jan. 20, 2014 for Application No. 201080055393.6 and English translation thereof.
Office Action mailed Dec. 19, 2013 for U.S. Appl. No. 12/953,744.
Chinese Office Action mailed Dec. 11, 2013 for Application No. 201180013047.6 and English translation thereof.
European Office Action mailed Jul. 29, 2013 for Application No. 11700881.3.
Office Action mailed Jan. 16, 2014 for U.S. Appl. No. 13/006,177.
Chinese Office Action mailed Jan. 16, 2014 for Application No. 201080017375.9 and English translation thereof.
Japanese Office Action mailed May 27, 2014 for Application No. 2011-552936.
Office Action mailed Mar. 7, 2014 for U.S. Appl. No. 13/166,451.
Restriction Requirement mailed Jun. 9, 2014 for U.S. Appl. No. 13/812,248.
Chinese Office Action mailed May 13, 2014 for Application No. 201180040283.7.
European Office Action mailed Jan. 16, 2014 for Application No. 11736245.9.
Office Action mailed Apr. 11, 2014 for U.S. Appl. No. 13/183,789.
European Office Action mailed Dec. 10, 2013 for Application No. 11746127.7.
Office Action mailed May 29, 2014 for U.S. Appl. No. 13/208,770.
Office Action mailed Apr. 10, 2014 for U.S. Appl. No. 13/208,808.
Office Action mailed Nov. 25, 2013 for U.S. Appl. No. 13/292,254.
Chinese Office Action mailed Mar. 11, 2014 for Application No. 201180013052.7.
Office Action mailed Dec. 30, 2013 for U.S. Appl. No. 13/006,165.
Office Action mailed Jan. 3, 2014 for U.S. Appl. No. 13/456,394.
Office Action mailed May 20, 2014 for U.S. Appl. No. 13/456,505.
International Preliminary Report on Patentability for PCT/US2012/035173 mailed Nov. 7, 2013.
Chinese Office Action mailed Oct. 20, 2014 for Application No. CN 201080017376.3.
Chinese Office Action mailed Sep. 12, 2014 for Application No. CN 201080055393.6.
European Office Action mailed Sep. 29, 2014 for Application No. EP 10776881.4.
Japanese Office Action mailed Jul. 25, 2014 for Application No. JP 2012-537119.
Chinese Office Action dated Aug. 29, 2014 for Application No. CN 201180013047.6.

(56) References Cited

OTHER PUBLICATIONS

European Office Action mailed Jul. 7, 2014 for Application No. EP 11700881.3.
Japanese Office Action mailed Nov. 5, 2014 for Application No. JP 2012-549080.
Examination Report dated Aug. 14, 2014 for Application No. EP 11736245.9.
Chinese Office Action mailed Sep. 30, 2014 for Application No. 201180060903.3.
European Office Action mailed Jul. 30, 2014 for Application No. EP 11785255.8.
Chinese Office Action mailed Nov. 19, 2014 for Application No. 201180013052.7.
European Office Action dated Aug. 28, 2014 for Application No. EP 11700780.7.
Japanese Office Action mailed Oct. 20, 2014 for Application No. JP 2012-549079.
Office Action dated Oct. 31, 2014 for U.S. Appl. No. 12/915,735.
Office Action mailed Jul. 21, 2014 for U.S. Appl. No. 12/915,820.
Office Action mailed Jul. 8, 2014 for U.S. Appl. No. 12/953,744.
Final Office Action mailed Nov. 24, 2014 for U.S. Appl. No. 13/006,177.
Office Action mailed Jan. 15, 2015 for U.S. Appl. No. 12/716,226.
Final Office Action mailed Nov. 12, 2014 for U.S. Appl. No. 13/166,451.
Office Action mailed Dec. 9, 2014 for U.S. Appl. No. 13/208,770.
Office Action mailed Nov. 20, 2014 for U.S. Appl. No. 13/208,808.
Final Office Action mailed Nov. 24, 2014 for U.S. Appl. No. 13/006,165.
Office Action mailed Jul. 31, 2014 for U.S. Appl. No. 13/456,394.
Office Action mailed Dec. 16, 2014 for U.S. Appl. No. 13/456,505.
Office Action mailed Oct. 9, 2014 for U.S. Appl. No. 13/443,016.
Office Action mailed Sep. 22, 2014 for U.S. Appl. No. 13/456,546.

* cited by examiner

MONITORING OR FEEDBACK SYSTEMS AND METHODS

RELATED APPLICATIONS

This application claims the benefit of U.S. Provisional Patent Application Ser. No. 61/299,283, filed Jan. 28, 2010, titled "Monitoring or Feedback Systems and Methods," by Levinson, et al., incorporated herein by reference.

FIELD OF INVENTION

The present invention generally relates to systems and methods for monitoring and/or providing feedback for drugs or other pharmaceuticals taken by a subject.

BACKGROUND

One problem often faced by physicians and other health care providers is that drugs and other pharmaceuticals that are prescribed to subjects are not taken by the subjects, or are not taken properly by the subjects. The reasons for non-compliance or poor compliance vary, and include forgetfulness, cost, inconvenience, lack of follow-up, or fear of taking medications. Accordingly, techniques for monitoring or improving compliance are needed.

SUMMARY OF THE INVENTION

The present invention generally relates to systems and methods for monitoring and/or providing feedback for drugs or other pharmaceuticals taken by a subject. The subject matter of the present invention involves, in some cases, interrelated products, alternative solutions to a particular problem, and/or a plurality of different uses of one or more systems and/or articles.

In one aspect, the present invention is generally directed to a device. In one set of embodiments, the device includes a sensor able to determine a species withdrawn from a subject, and an indicator able to indicate an external reward based on the determination of the species. In another set of embodiments, the device includes means for determining a species withdrawn from a subject, and means for providing an external reward based on the determination of the species.

In some embodiments, the device includes a sensor configured, adapted or designed to determine a species withdrawn from a subject, and a device indicator, responsive to the sensor and configured to indicate an external response based on the determination of the species.

In accordance with yet another set of embodiments, the device includes a sensor able to determine an amount and/or concentration of a species withdrawn from a subject, and a component able to produce non-number feedback related to the amount or concentration of the species.

In some embodiments, the device includes means for sensing a species withdrawn from a subject, and means for indicating an external reward based on the sensing of the species. In certain instances, the device includes means for withdrawing a species from a subject using a device fastened to the subject, means for determining information comprising an amount and/or a concentration of the species using at least the device, and means for transmitting the information to a computing device, wherein the computing device is configured to provide, via an output device, non-number feedback to the subject based on the transmitted information. In one set of embodiments, the device includes means for determining information representing a property of a species withdrawn from a subject using a device immobilized to the skin of the subject, and means for transmitting the information to a machine configured to cause an external response to be presented to a user of the machine.

The present invention, in another aspect, is directed to a method. According to one set of embodiments, the method includes acts of determining a species withdrawn from a subject using a device fastened to the subject, and providing an external reward based on a concentration of the species. In another set of embodiments, the method includes acts of determining a species withdrawn from a subject, on multiple days, using one or more devices able to be fastened to the skin, and providing an external reward based on the number of determinations. The method, in yet another set of embodiments, includes acts of determining an amount and/or concentration of a species withdrawn from a subject using a device fastened to the subject, and producing non-number feedback indicative of the determination of the species.

In one set of embodiments, the method includes acts of determining information relating to a species withdrawn from a subject, transmitting the information to a computer, and causing the computer to provide feedback to the subject based on the information relating to the species. In another set of embodiments, the method includes acts of receiving information obtained from a subject representing a property of a species withdrawn from the subject, and presenting an external reward to a user based on the received data. The method, in still another set of embodiments, includes acts of determining information representing a property of a species withdrawn from a subject using a device fastened to the subject, and transmitting the information to a machine capable of causing an external reward to be presented to a user of the machine.

In one set of embodiments, the method includes acts of withdrawing a species from a subject using a device fastened to the subject, determining information comprising an amount and/or a concentration of the species using at least the device, and transmitting the information to a computing device. In some cases, the computing device is configured to provide, via an output device, non-number feedback to the subject based on the transmitted information.

The method, in certain embodiments, includes acts of receiving information obtained from a subject representing a property of a species withdrawn from the subject, and presenting an external response to a user based on the received data.

In some embodiments, the method includes acts of determining information representing a property of a species withdrawn from a subject using a device immobilized to the skin of the subject, and transmitting the information to a machine configured to cause an external response to be presented to a user of the machine.

The method, according to one set of embodiments, includes acts of administering a drug to a subject, determining a species withdrawn from a subject that is indicative of the drug administered to the subject, and providing feedback to the subject regarding the species. In some embodiments, the drug administered to the subject is not distinguishable from a placebo by the subject without any external equipment. In some embodiments, the method includes acts of administering a drug to a subject, determining a species withdrawn from a subject that is indicative of the drug administered to the subject, and providing feedback to the subject regarding the species. In some cases, the drug administered to the subject can not be distinguished, by the subject, from a placebo without any external equipment.

In yet another set of embodiments, the method includes acts of administering a drug to a subject having a condition suspected of being treatable by the drug, determining a species withdrawn from a subject that is indicative of the drug administered to the subject, and providing feedback to the subject regarding the species. In some cases, the drug does not cause a measurable change to the condition of the subject within the first 24 hours after administering the drug. In accordance with certain embodiments, the method may include acts of administering a drug to a subject having a condition suspected of being treatable by the drug, determining a species withdrawn from a subject that is indicative of the drug administered to the subject, and providing feedback to the subject and/or another person regarding the species. In some instances, the drug does not cause a measurable change to the condition of the subject within the first 24 hours after administering the drug.

In another aspect, the present invention is directed to a method of making one or more of the apparatus embodiments described herein. In another aspect, the present invention is directed to a method of using one or more of the apparatus embodiments described herein.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically (though not necessarily) represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1A:
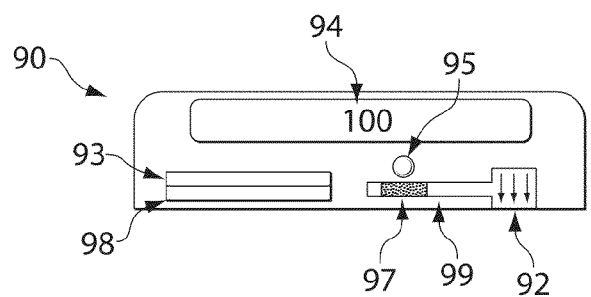
FIG. 1A-1B illustrate devices according to certain embodiments of the invention.

The present invention generally relates to devices and methods for determining a species within the skin of a subject; and producing feedback to a subject based on the determination of the species. In some embodiments, the invention is generally related to systems and methods for monitoring and/or providing feedback for drugs or other pharmaceutical substances taken by a subject. The feedback may be, for example, visual, audible, tactile, a change in temperature, etc. In some cases, information regarding the determination of the species may be transmitted to another entity, e.g., a health care provider, a computer, a relative, etc., which may then provide feedback to the subject in some fashion. In some cases, the feedback may be directly indicative of the species, e.g., whether the species is present, the concentration and/or amount of the species, whether a by-product of a reaction involving the species is present (and, if so, perhaps in what amount and/or concentration), whether a compound affected by the species is present (and, if so, perhaps in what amount and/or concentration), etc. However, the feedback may also be indirect in some embodiments. For example, the subject may be presented with an external reward, e.g., based on the determination of the species within the skin. For instance, a reward such as cash, coupons, songs, discounts, personal items, etc., may be offered based on the level of compliance of the subject. Still other aspects of the invention are generally directed to kits involving such devices (with or without a drug or other substance to be monitored), methods of promoting such systems, or the like.

In one aspect, the present invention is directed generally to devices able to monitor or provide feedback to a subject taking (or not taking) a drug or other pharmaceutical substance, and/or to provide such feedback to other personnel. For example, feedback may be provided to a relative of the subject, a caregiver for the subject, medical personnel caring for the subject (e.g., a nurse, a doctor, etc.), or the like. Thus, in one set of embodiments, feedback may be provided to anyone who would communicate such feedback to the subject. The subject is typically human, although the subject may be non-human in some cases. The feedback given to the subject may be based on information regarding the determination of the drug or other pharmaceutical substance, for example, an amount and/or concentration of the drug or other pharmaceutical substance within the subject. The determination may be qualitative (e.g., determining the presence or absence of the drug or other pharmaceutical substance) and/or quantitative (e.g., determining an amount and/or concentration, etc.). For instance, the feedback may include information regarding the subject's compliance with taking (or not taking) one or more drugs or other pharmaceutical substances. Depending on the personnel, additional information may be given to the subject, e.g., warnings about compliance (or lack thereof), information about potential drug interactions, suggestions for improving compliance, suggestions for changes in lifestyle, or the like.

Figure 3A:
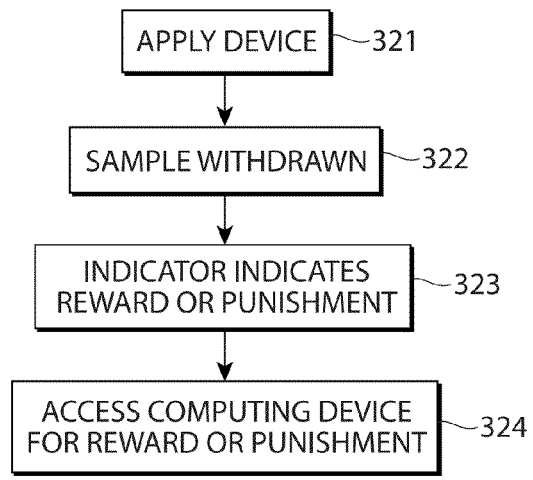
FIGS. 3A-3C illustrate certain methods in accordance with various embodiments of the invention.

A non-limiting example of such a process is now described with respect to the flowchart shown in FIG. 3A. In this figure, a device is applied to a subject 321, e.g., by the subject (i.e., self-administered) or another person (e.g., a health care provider). The device is then activated (or in some cases, self-activated) to withdraw fluid 322 from the subject, e.g., blood, interstitial fluid, etc. The device may then analyze the fluid for one or more species, e.g., using one or more sensors as discussed herein. In some cases, analysis of the species occurs on the device itself. In certain instances, information about the species (e.g., the presence and/or absence, concentration, amount, etc.) is transmitted externally of the device, e.g., to a computing device, which may also in some embodiments return a signal to the device. After such analysis, if certain conditions are met, the device may activate an indicator 323 (e.g., light, sound, graphics, music, etc.) which alerts the subject (or another person) that an external reward or punishment is available. The subject (or another person) can then access a computing device 324 (which may be the same or different from the computing device discussed above) to access the external reward and/or to determine what punishment is to be applied. The computing device may, for example, display a weblink to access the reward or punishment, and/or there may be an output device able to output a reward (e.g., a coupon or a certificate).

Figure 4:
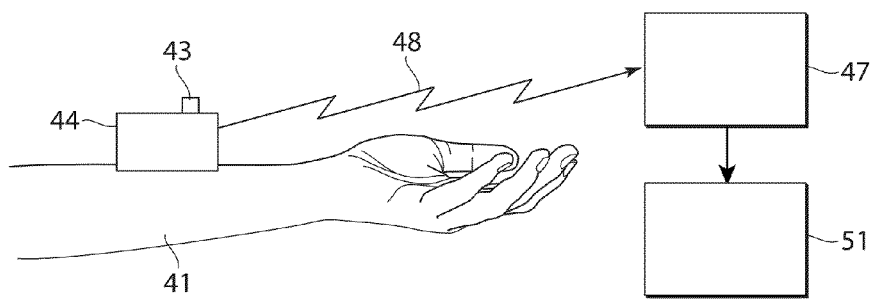
FIG. 4 is a schematic diagram illustrating a device transmitting information about a species from a subject to a device able to offer a reward, in accordance with one embodiment of the invention.

A schematic illustration of such a system is shown in FIG. 4. In this figure, a device 44 for withdrawing a fluid is placed on a portion of a subject 41 (e.g., an arm or a leg), and in some cases, immobilized thereto (for example, using an adhesive). After withdrawing a sample from the subject (e.g., blood or interstitial fluid), device 44 determines one or more species suspected of being present within the sample using one or more sensors. Information from the sensors may be analyzed by device 44, and/or transmitted 48 to an external computing device 47. For example, device 44 may determine the presence of a species, and in some cases, determine if an external reward (or punishment) should be offered to the subject. If an external computing device is used, any method of transmission to the computing device may be used, including wireless or radio transmissions. In some cases, external computing device 47 may also send a signal back to device 44. For example, in some embodiments, external computing device 47 may be used to analyze the species and determine if an external reward (or punishment) should be offered to the subject. Thus, information about the species and/or whether such an external reward or punishment should be offered may be transmitted back to device 44.

If it is determined that the subject should be offered an external reward (or punishment), device 44 may activate a suitable indicator 43 to inform the subject (or another person). For example, indicator 43 may be include a display screen, a speaker, a light or an LED, or the like, e.g., as discussed herein. Computing device 47, and/or another output device 51, may then be used to offer the external reward (or punishment) to the subject (or other person). For example, the subject or other person may access computing device 47 and/or output device 51 to claim the reward or accept the punishment.

The species to be determined within the subject may be present anywhere within the subject, e.g., within or beneath the skin of the subject, and/or within other bodily fluids such as blood or interstitial fluid. The species may be an administered composition (e.g., a drug or other pharmaceutical substance), and/or another species that is related to such a composition, such as a tracer or other compound taken with the administered compound, for example, such as the systems and methods disclosed in U.S. Pat. Apl. Ser. No. 61/163,733, filed Mar. 26, 2009, titled "Determination of Tracers within Subjects," by Douglas A. Levinson, or U.S. patent application Ser. No. 12/748,316, filed Mar. 26, 2010, titled "Determination of Tracers within Subjects," by Douglas A. Levinson, published as U.S. Patent Application Publication No. 2010/0272652 on Oct. 28, 2010, each incorporated by reference herein in their entireties. For example, the species to be determined may be the product of an interaction of the drug (or other pharmaceutical substance) with the subject. As specific non-limiting examples, the species may be a metabolite of the administered composition; a product or by-product of the administered composition with the subject (for example, a cleavage product); a marker for a condition that would be affected by, or a disease that is treatable by, the administered composition (for instance, a protein, a hormone, a small molecule, etc.); a species within the body that the administered (or to-be-avoided) composition interacts with (e.g., degrades), such as a target of that composition (for example, a protein or enzymatic target within the subject), or the like. Accordingly, in the description herein, it should be understood that references to determining the drug (or other pharmaceutical or other administered substance) in the subject (e.g., in the skin, blood, interstitial fluid, etc. of the subject) are by way of example only, and in other embodiments, other species related to the administered composition may be determined in any suitable location within the subject, instead of or in addition to the administered composition, such as those described herein.

As mentioned, in some embodiments of the invention, a species may be determined indirectly, for example, using a tracer of the species. As used herein, a "tracer" is a substance that can be determined within a subject, typically upon interaction with an indicator. In some cases, the tracer is determinable in some fashion, e.g., by a sensor as disclosed herein. For example, the tracer may be radioactive or fluorescent in some cases; although in other cases, the tracer may not be radioactive and/or fluorescent. The determinable change in the tracer and/or the indicator may be a visual change such as a change in appearance (e.g., color), a change in temperature, a change in sensation, or the like. The tracer itself may be any suitable compound that can be administered to the subject. In some cases, the determinable change may be one that can be determined by a human without the use of any equipment, for example, visually, tactilely, or the like. In other cases, the determinable change may be determinable using suitable instrumentation.

In some cases, the tracer is chosen to have relatively little, or essentially no, biological activity, and can be determined mainly by its interaction with the indicator. However, in other cases, the tracer may have some biological activity. For instance, the amount of biological activity of the tracer within the subject may be predictable. As an example, a tracer may be cleared by the kidneys from the bloodstream at a certain rate, and by determining the concentration of tracer within the subject, e.g., by determining a change in a determinable property (e.g., a chemical property, a physical property, an electrical property, etc.) in an indicator, and correcting for the clearance rate of the tracer, the pharmacokinetic activity of the tracer within the subject may be determined, and used to determine the pharmacokinetic activity of a substance administered to the subject. Usually, the tracer is produced externally or exogenously, then administered to the subject as discussed below. Non-limiting examples of tracers include certain proteins or carbohydrates such as inulin, or small molecules (typically less than about 1000 Da) such as creatinine.

The tracer may be relatively non-toxic in some cases. In one set of embodiments, the tracer is a molecule that has a relatively high rate of clearance from the body. For instance, the half-life of the tracer within the body may be less than about 3 days, less than about 2 days, less than about 1 day, less than about 18 hours, less than about 12 hours, less than about 9 hours, less than about 3 hours, or less than about 1 hour. In some cases, the tracer may include poly(ethylene) glycol, for example, PEG 300, PEG 400, PEG 2000, PEG 3350, or PEG 8000 (where "PEG" stands for poly(ethylene) glycol and the number indicates the molecular weight).

As a non-limiting example, the tracer may exhibit substantially the same pharmacokinetic activity as the administered substance, or at least exhibit certain pharmacokinetic activities indicative of the substance. For instance, the tracer may exhibit similar absorption and/or distribution rates within the body, the same duration within the body, the same metabolism within the body, or the same excretion rates from the body, e.g., through the urine. In other cases, however, the tracer and the substance may exhibit substantially different pharmacokinetic parameters. For example, the tracer may exhibit substantially slower or faster absorption or distribution within the body. However, by determining the tracer, e.g., using an indicator, an estimate of the pharmacokinetic activity of the substance within the body may still be obtained. In one embodiment, it may be sufficient to simply determine whether the tracer is present or absent in the body, and then infer that the substance is also present or absent in the body based on the tracer (for example, if the subject is given a composition that comprises both the tracer and the substance to be administered as a single entity). In some cases, the amount of tracer delivered to the subject may also be controlled in some fashion, for example, such that the certain pharmacokinetic activities of the tracer are substantially similar to the pharmacokinetic activities of the substance also administered to the subject. As non-limiting examples, the substance may be an alcoholic beverage or a drug that is administered with a tracer, and the indicator used to determine whether the subject has indeed taken the substance or not.

Feedback may be provided in any suitable form. As mentioned, feedback may be provided to the subject or to other personnel. In some cases, the feedback may be directly provided by the device, e.g., to the subject after determination of the species. In one set of embodiments, the feedback may be auditory, visual, olfactory, tactile, thermal, or the like.

For example, if the feedback is auditory, the feedback may include sounds such as jingles, songs, music, sound effects, or the like. In some cases, the sounds may be selectable by the subject or other personnel. For instance, the subject may select a first song indicating compliance, and a second song (or no song) indicating non-compliance; the subject may also select additional songs in some embodiments for other indications (e.g., partial compliance, a reminder to take the composition, a song indicating successful compliance over some predetermined period of time or number of administrations, etc.). Sound may be produced by a device using any suitable technique, for example, using a speaker or a relay clicker. Techniques for causing a speaker to play music or sounds will be familiar to those of ordinary skill in the art. For example, the speaker may be a digital speaker that plays songs stored in a memory device, e.g., in any suitable format (e.g., flash memory, magnetic tape, hard drive memory, optical media such as CDs or DVDs, or the like). Other types of sounds may be used in other embodiments, for example, sound effects (e.g., beeps, buzzes, jingles, etc.), synthesized sounds or speech, verbal reminders, or the like.

As another example, the feedback may be tactile. One non-limiting example of a tactile sensation is a change in temperature (e.g., getting warmer or cooler), for example, using electronic heating or cooling devices such as resistive heaters or Peltier coolers. Thus, as a particular example, a device may be worn that produces heat or cooling when compliance is lacking, thereby reminding the wearer to administer the drug or other pharmaceutical substance. As other examples of tactile feedback, the device may vibrate, tighten or loosen, etc. to indicate certain conditions, e.g., as positive or negative feedback provided to the subject. For instance, the device may be worn around the arm (e.g., as in a bracelet or wristwatch), and the device may tighten around the arm if the subject has or has not been compliant.

In yet another set of embodiments, the feedback may be visual. For example, the device may include an output device including one or more lights, LEDs, LCDs, a screen able to display an image, or the like. As a specific non-limiting example, lights may be provided that are red when compliance is lacking and green if the subject exhibits adequate compliance. In some cases, the lights may also flash, e.g., to get attention. Other lights may be provided in other embodiments, for example, to indicate that the next administration is due, to indicate operation of the device, to indicate successful compliance over some predetermined period of time or number of administrations, etc. As another example, a light within the device may be used to produce a logo or an advertisement when the composition has been taken, etc. In some cases, the feedback may be non-number based, i.e., the feedback does not include the display of numbers, but instead contains other methods or symbols to indicate feedback, e.g., lights, bars, plots, signals, graphs, logos, or the like. As still another example, the device may display numbers, a series of lights, pictograms, LEDs, LCDs, logos, etc., indicating information regarding the species within the subject, for example, the concentration, the number of times the drug or other pharmaceutical substance was taken by the subject, the time since the last administration of the drug or other pharmaceutical substance was previously administered, the time before the next administration, or the like. If a screen is used, the screen may be able to display arbitrary information, e.g., regarding operation of the device, information regarding the species within the subject, information regarding administration of the drug or other pharmaceutical substance, weblinks or hyperlinks, or other useful information, etc. In still another embodiments, the device may produce a desirable display of lights, logos, advertisements, movies, etc., as a reward for successful compliance.

These may also be combined in still other embodiments. For example, the device may produce a movie with sounds to indicate compliance (or lack thereof), the device may produce blinking lights during or following a song, or the like.

In one set of embodiments, the feedback that is provided by the device may be related to the drug or other pharmaceutical substance in some way. For example, the feedback may indicate whether the drug (or other pharmaceutical substance) was taken or not, the degree of compliance, the concentration of a species within the subject (measured directly or indirectly, e.g., by determining a metabolite within the subject), the time since the drug or other substance was taken, the time until the next administration of the drug, the number of administrations, etc. In some of embodiments, the feedback may be a reward indicating some degree of successful compliance. For example, feedback may be provided after the subject has taken the drug or other substance, after the subject has taken the drug or other substance a certain number of times, after the subject has taken the drug or other substance for a certain period of time, once a certain concentration (e.g., high or low) of a species within subject has been reached, or the like. The feedback may be numerical and/or non-numerical. Such feedback may, in some embodiments, be of sufficient value to the subject that the subject may behave in a certain way, e.g., increasing compliance or continuing taking the drug or other pharmaceutical substance. In other embodiments, as discussed herein, the feedback may include a reward, such as an external reward or other external response (e.g., a punishment). The reward may also influence the subject's behavior in some cases.

In some cases, feedback may be provided to the subject in real time, e.g., by the use of a graph, numbers, lights, etc. As a particular example, the device may display a number that indicates the concentration or amount of a species within the subject (e.g., glucose), and optionally, when a certain concentration is reached, the device may also indicate to the subject in some fashion that a medication (e.g., insulin) is needed, for example, by activating a light, displaying a logo, playing a sound or a song, or the like.

Figure 3B:
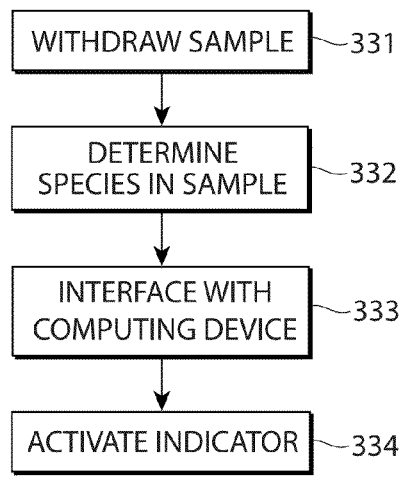

As illustrated in the example of FIG. 3B, the device, in one set of embodiments, may be operated as follows. A sample may be withdrawn from a subject to which the device is applied 331. For example, the sample may be blood, interstitial fluid, or the like. The device then analyzes the sample 332 to determine one or more species within the sample, e.g., the presence and/or absence, amount, concentration, etc. For example, one or more sensors as discussed herein may be present within the device. In some cases, analysis of the species occurs on the device itself. In certain instances, the device interfaces with an external computing device 333 so that information about the species (e.g., the presence and/or absence, concentration, amount, etc.) can be transmitted externally of the device, e.g., to a computing device, which may also in some embodiments return a signal to the device. Based on such analysis, the device may then activate an indicator 334, for example, light, sound, graphics, music, etc. to alert the subject (or another person) that an external reward (or punishment) is available. In some cases, the device itself may perform the analysis of the species and activate the indicator, prior to interfacing with an external computing device.

The device may be used once, or multiple times. For instance, in one set of embodiments, the device may be used to determine a species within the skin at multiple points of time, e.g., on multiple days, or even continuously in some instances. Feedback may be provided to the subject immediately or within a short time after determining the species, and/or information regarding the species may be stored for later use (e.g., as discussed below). For instance, in one set of embodiments, after the subject has taken the drug or other substance a certain number of times, or after a certain number of days, feedback may be provided to the subject, for example, in the form of a reward or punishment as discussed below.

As discussed, in one set of embodiments, feedback is provided by the device itself. However, in another set of embodiments, feedback may be provided by another entity. The entity may be another person (such as a relative, medical personnel, etc.), or a non-living entity, such as a computing device or an Internet-based service. For example, information about the species may be transmitted to the other entity, which may then provide feedback to the subject in a suitable fashion. Examples of computing devices include, but are not limited to, general purpose computers, specially-built computers, application-specific integrated circuits, microprocessors, or the like. In some cases, the computing device may interface with an output device, e.g., configured to provide feedback such as is discussed herein, for instance, visual feedback, auditory feedback such as music, etc. In some embodiments, after a device determines a species, an indicator on the device may be used to indicate that an external reward (or punishment) is available based on the determination of the species, for example, on a web site or an output device. Examples of indicators include screens, lights, speakers, etc., as is discussed herein.

Figure 3C:
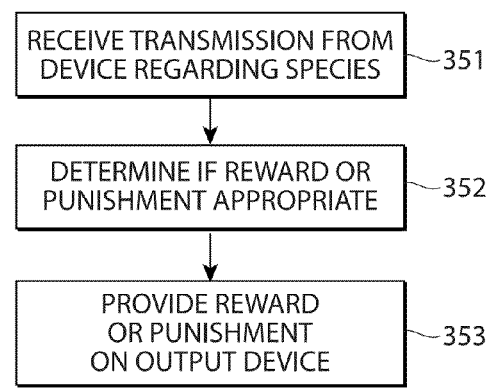

One non-limiting example method of using the computing device is now illustrated with respect to FIG. 3C. In this figure, an external computing device (e.g., a general purpose computer, a specially-built computer, an application-specific integrated circuit, a microprocessor, etc.) receives a transmission 351 from a device that is used to withdraw a sample from a subject for analysis. The sample may be, for example, blood or interstitial fluid. For example, the device may include one or more sensors able to determine a species suspected of being present within the sample withdrawn from the subject, and the device may transmit sensor data, and/or the device may analyze sensor data and transmit information about the species (e.g., the presence or absence, amount, concentration, etc.) to the computing device. In this example, based on the transmission, the computing device may determine if a reward (or punishment) is appropriate 352, e.g., using criteria such as those described herein. Optionally, the computing device (or another computing device) may be used by the subject, or another person, to access an external reward or punishment 353. For example, the computing device may be a computer that a person can log into to receive the external reward. In some cases, the computer device may be connected to an output device for producing the external reward, e.g., a screen, a TV, a printer, a speaker, or the like.

In one set of embodiments, the device may transmit information regarding the subject and/or administration of the drug or other pharmaceutical substance to another entity. The information may be transmitted, e.g., wirelessly (for example, using radio antennas, transceivers, infrared light, laser light, visible light, acoustic energy, or the like), or through the use of wires (for example, using electronic ports such as parallel ports, serial ports, USB connections, RS232/485 communication transceivers, 4-20 mA analog transceivers, an Ethernet transceiver, or the like). Any suitable transmission protocol may be used, e.g., Bluetooth, Wi-Fi or IEEE 802.11, WiMax, peer-to-peer networking, Wireless FireWire, or the like. The information may be transmitted relatively quickly after determination of a species within the subject, and/or the information may be stored for later transmission and/or retrieval, for example, by the subject, or by another person.

If information is stored on the device, any suitable technique may be used to store such information, e.g., in a data storage compartment, for example, silicon integrated circuits, magnetic media, optical media, or other kinds of data storage devices. In one embodiment, the data storage component includes a computer-readable medium, for example, a medium that stores information through electronic properties, magnetic properties, optical properties, etc. of the medium. Examples of computer-readable media include, but are not limited to, silicon and other semiconductor microchips or integrated circuits, radio frequency tags or circuits, compact discs (e.g., in CD-R or CD-RW formats), digital versatile discs (e.g., in DVD+R, DVD-R, DVD+RW, or DVD-RW formats), insertable memory devices (e.g., memory cards, memory chips, memory sticks, memory plugs, etc.), "flash" memory, magnetic media (e.g., magnetic strips, magnetic tape, DATs, tape cartridges, etc.), floppy disks (e.g., 5.25 inch or 90 mm (3.5 inch) disks), optical disks, and the like. In one set of embodiments, the data storage component may be reversibly attached to and removed from the device. In some embodiments, the data storage component may be volatile, i.e., some power is required by the data storage component to maintain the data therein. In other embodiments, however, the data storage component is non-volatile. In some embodiments, the data storage component is an element that is constructed and arranged to allow data to be stored to and/or retrieved. In one embodiment, the memory or data storage component includes a data storage chip. As used herein, a "data storage chip" is a microchip or microprocessor to which data can be stored and/or retrieved. Typically, the data storage chip comprises a semiconductor and often contains electronic circuitry.

In some embodiments, information regarding the subject and/or administration of the drug or other pharmaceutical substance may be provided to the subject or another person. For instance, the device may determine a species within the skin of a subject, then transmit the information regarding the species to another entity, e.g., a receiver, a computer, a computing device, a web page on the Internet, etc., for retrieval and/or analysis by another person, e.g., the subject, a relative, medical personnel, etc. If another person is involved, the person may provide feedback to the subject. For example, the person could review information regarding the species, and/or make a determination regarding compliance of the subject with administration of the drug or other pharmaceutical substance. In some cases, the person may give advice (such as medical advice), warnings, encouragement, counseling, etc., to the subject regarding administration and/or compliance issues. In addition, as previously discussed, in some embodiments, additional information may also be given to the subject, for example, information about potential drug interactions, suggestions for changes in lifestyle, methods for improving compliance, changes in prescription, or the like.

In one set of embodiments, the device may indicate that the subject (or another person, as described herein) may have access to a web page. The device may indicate access to the web page by any suitable technique, for example, visual, audible, tactile, a change in temperature, etc. As non-limiting examples, the device may turn on a light, display an image or a logo, to produce a sound, play a song, etc. to indicate that the web page is accessible, to indicate a change or an update in the content of the web page, produce a reminder to review the web page, etc.

The web page may be used to display information to the subject, and/or to another person. For instance, in one set of embodiments, the device may transmit information to another entity (e.g., a computer or a computing device), and the computer may produce a web page that can be accessed by the subject, or another person. In some cases, the web page may be a private or encrypted web page accessible only to the subject, and/or only to select individuals (e.g., certain doctors or other health care providers). The web page may display information relating to the species, other information of interest to or for the subject, or in some cases, the web page may be used to provide a reward to the subject, e.g., for sufficient compliance, or a punishment to the subject, e.g., for insufficient compliance.

For example, the web page may, in some embodiments, display information relating, directly or indirectly, to the species. For example, the web page may display information regarding compliance or administration of the drug or other pharmaceutical substance by the subject, the concentration of a species in the subject (e.g., of the drug or other pharmaceutical substance, or a species related to the drug or other pharmaceutical substance, e.g., a metabolite, a target, a product, a by-product, a marker for a disease treatable by the drug or other pharmaceutical substance, etc.). As other examples, the web page may indicate whether the drug (or other pharmaceutical substance) was taken or not, the number of times it was taken by the subject, the degree of compliance, the concentration of a species within the subject (measured directly or indirectly, e.g., by determining a metabolite within the subject), the time since the drug (or other pharmaceutical substance) was taken, the time until the next administration of the drug, the number of administrations, other health-related information (e.g., relating to the composition, for example, potential side effects, allergic reactions, interactions with other drugs, etc.), as well as past histories or one or more of these in some cases, or the like.

In some cases, the web page may display information of interest to or for the subject. As non-limiting examples, the web page may display information or advertising regarding the drug or other drugs (or other substances) of potential interest to or for the subject, health-related information, links to related web sites, or the like. As specific examples, the web page may include a link to an on-line "chat" with medical personnel who can answer questions that the subject may have regarding the subject's health, or the web page may provide counseling regarding improving compliance of the subject in taking the drug or other pharmaceutical substance.

In another set of embodiments, the web page may use information relating to the species to produce information, data, probabilities, etc., relating to the subject. For instance, the web page may indicate that, by successfully complying with a treatment for a certain period of time, the probability of an adverse event has been changed. As a specific example, the web page may report that, by successfully complying with treatment over a certain period of time, the probability of a heart attack has decreased by a certain percentage, the probability of an acute attack of a disease has decreased by a certain percentage, the life expectancy of the subject has increased by a certain amount, etc.

According to one set of embodiments, feedback provided to the subject may include a reward, e.g., upon achieving some level of successful compliance. For example, the feedback or reward may be provided after the subject has taken a drug (or other pharmaceutical substance), after the subject has taken the drug a certain number of times, after the subject has taken the drug for or after a certain period of time, once a certain concentration of a species within subject has been reached, or the like. In some cases, the reward may be one selected by the user; in other cases, the reward may be determined by another person, e.g., by a doctor or other health care provider, or the reward may be predetermined. For instance, as discussed below, in one set of embodiments, a kit may be provided to the subject that includes a drug or other pharmaceutical substance, and a device able to determine the drug within the skin. The device may, in some cases, be preprogrammed to give a reward when a certain level of compliance by the subject is reached.

The reward may be any suitable reward. In some cases, the reward may be one determinable by the user. In one set of embodiments, the reward may be provided directly by the device. For instance, the device may display an image, play a song or music, display a pattern of lights, play a movie or a movie clip, etc., as a suitable reward to the subject. In some cases, however, the reward may be one that is external to the device, i.e., the reward is an "external reward," which, in the present invention, means a material (e.g., financial) and/or encouragement-related reward that is provided to the subject, a source that is not solely the device for obtaining a species and/or sample from a subject. The external source can be, for example, an individual, a computer, a computing device, or the like, alone or in combination with the devise. Typically, the source of the external reward is a database within, or is controlled by, a computing device that receives information from the device (directly or via an intermediary) and then determines whether a reward should be provided.

As noted, human interaction can also be involved in determining whether a reward should be provided. For example, the reward may be a monetary reward (e.g., cash, coupons, discounts, gift cards, etc.), physical merchandise (e.g., of a predetermined nature, or selectable by the user, etc.), downloadable content (e.g., sound files, game files, pictures, movies, etc.), or the like. As a specific non-limiting example, the reward may be one or more arbitrary "points," and when a certain number of points are reached, the subject may be given a reward, or the subject may be allowed to choose a reward from a number of potential rewards. In some cases, the subject may be able to acquire even more points (for example, for higher levels of compliance, longer periods of compliance, smaller fluctuations in the concentration of a species, etc.) and the ability to choose even larger or more valuable rewards. The reward may be selectable, for example, by access to a suitable web page (e.g., as discussed herein), by selecting an item from a physical or an electronic catalog, or the like. As mentioned, in one set of embodiments, an indicator on the device may be used to indicate that an external reward is available.

In other embodiments, a punishment may be used instead of and/or in addition to a reward, e.g., punishment for insufficient compliance. Accordingly, it should be noted that in the discussions herein involving "rewards," punishments may also be used in other embodiments, instead of and/or in addition to rewards. For example, the punishment may be monetary (e.g., a fine), or reduction in points, or simply the absence of any positive feedback.

In some aspects, the systems described herein may be useful for monitoring intake or effectiveness of any drug or other ingestible or injectable substance (for which we will use the term "drug" whether the substance be pharmaceutical or not). In some cases, the drug (or other substance) may be one in which the benefit to the subject taking the drug is not necessarily immediate or apparent. For example, a drug able to treat anemia or decrease cholesterol levels may have benefits that are not immediately felt by the subject (e.g., an increase in red blood cell count or a decrease in the amount of cholesterol found in the blood). Thus, the subject taking the drug may not be aware of any immediate substantial benefit by taking the drug. In many cases, the subject is discouraged from taking the drug due to the lack of any positive feedback, i.e., beneficial effects, by taking the drug. In some instances, this may be compounded by drugs having one or more adverse side effects, i.e., the subject is immediately exposed to adverse side effects upon taking the drug, while the beneficial effects of taking the drug are not immediately apparent. Accordingly, it is a feature of certain embodiments of the invention to provide feedback systems for subjects taking drugs, including but not limited to drugs having benefits that are not necessarily immediate or apparent.

In one set of embodiments, the drug (or other substance) is one whose beneficial effects occur on the time scale of weeks, or drugs whose main actions do not occur until at least about a day. Examples of such drugs include, but are not limited to, drugs that treat anemia, drugs that lower cholesterol, or drugs that treat high blood pressure, drugs that treat arthritis, etc. Specific non-limiting examples are discussed below. In another set of embodiments, the drug is one which is quantified using analytical measurements of the subject (or samples taken from the subject). Often, such drugs have effects that cannot be felt by a subject, or cannot be quantified by a subject without analytical measurements beyond a sense of "feeling good." Examples include, but are not limited to, drugs that lower cholesterol, drugs that treat anemia, or drugs that treat high blood pressure. In some cases, the drug administered to the subject is not distinguishable, by the subject and/or by others, from a placebo without any external equipment (e.g., blood testing). For instance, on a time scale of a day, 2 days, 3 days, a week, 2 weeks, 3 weeks, 4 weeks, etc., the drug is one that would not be distinguishable from a placebo by a typical subject taking the drug. For instance, the effects of the drug may take a long time to occur, and/or the symptoms treated by the drug may not be immediately identifiable by the subject (e.g., treatment of mild anemia) in the absence of any external equipment (e.g., to determine levels of circulating blood cells).

In one set of embodiments, the subject may be one that has or is at risk for high levels of lipids within the blood, for example, cholesterol. In some cases, for example, the subject may have total blood cholesterol level of at least about 200 mg/dl, at least about 210 mg/dl, at least about 220 mg/dl, etc.; HDL cholesterol levels of less than about 50 mg/dl, less than about 40 mg/dl, less than about 30 mg/dl, etc.; and/or LDL cholesterol levels of at least about 130 mg/dl, at least about 140 mg/dl, at least about 150 mg/dl, etc. Drugs that a subject may take to reduce or lower cholesterol and/or other lipid levels include, but are not limited to, statins or HMG-CoA reductase inhibitors (e.g., mevastatin, atorvastatin, cerivastatin, fluvastatin, lovastatin, pitavastatin, pravastatin, rosuvastatin, simvastatin, and/or combinations of these and/or other compounds), resins (e.g., cholestyramine, colestipol, or colesevelam), fibrates (e.g., gemfibrozil, fenofibrate, clofibrate), or niacin, and these may be determined in a subject, e.g., in the blood. For instance, a reward may be presented to a subject after a certain number or frequency of positive results where a satisfactory level of a drug was determined within the subject.

In another set of embodiments, the subject may have or be at risk for anemia, for example, having a decrease in the number of red blood cells and/or hemoglobin. Drugs useful for treating anemia include, but are not limited to, iron supplements, folic acid, vitamin B-12, erythropoietin or the like.

The subject may have or be at risk for asthma in yet another set of embodiments. In some cases, the asthma may include occasional asthma attacks. Examples of drugs usefully for treating asthma include, but are not limited to, long-acting bronchodilators such as beta-2-adrenoceptor agonists, salmeterol, formoterol, bambuterol, or albuterol; steroids such as fluticasone or budesonide; or combinations of these and/or others.

The subject, in some embodiments, may have chronic obstructive pulmonary disease (COPD) or asthma. Examples of potentially useful drugs to treat conditions such as chronic obstructive pulmonary disease or asthma include, but are not limited to, beta-2 agonists such as salbutamol, albuterol, terbutaline, salmeterol, or formoterol; anticholinergics such as ipratropium or tiotropium; corticosteroids such as prednisone, fluticasone, budesonide, mometasone, or beclomethasone; theophylline; or phosphodiesterase-4 antagonists such as roflumilast or cilomilast. Combinations of these and/or other drugs may also be used in some cases.

In still another set of embodiments, the subject may have osteoporosis. The osteoporosis may be treatable by administering drugs such as estrogen, bisphosphonate, calcium, vitamin D, or raloxifene.

In yet another set of embodiments, the subject may have diabetes, and may need treatment, e.g., with insulin. Glucose may be determined in the blood of the subject to determine the subject's insulin need and/or compliance with taking insulin at prescribed times.

In some embodiments, the subject may suffer from various chronic heart diseases. Characteristics determinable to determine if the subject is taking suitable drugs include, but are not limited to, pulse rate, blood pressure, or blood measurements such as cholesterol, calcium, sodium, potassium, chloride, bicarbonate, blood urea nitrogen (BUN), magnesium, creatinine, or glucose. Rewards such as external rewards may be presented if certain goals are met for some or all of these.

In another set of embodiments, the subject may suffer from inflammatory or immune-mediated conditions that are subject to periodic "flare-ups" or acute attacks, and the subject accordingly needs to take drugs to control the frequency of such attacks. Examples include, but are not limited to, arthritis (e.g., rheumatoid arthritis, osteoarthritis, etc.).

In one set of embodiments, the subject may be one who is trying to reduce addiction, e.g., to nicotine or ethanol. Accordingly, nicotine or ethanol may be determined in the subject to determine if or to what degree the subject has been able to reduce addiction. Additionally, feedback, e.g., in the form of external rewards, etc., may be useful in providing a positive environment for the subject to continue efforts at reducing the addiction. Thus, for example, positive feedback or external rewards may be offered when the substance is not present (or present in a reduced amount) in the subject. In yet another set of embodiments, the subject may be one who is trying to lose weight. Glucose or other food compounds (e.g., triglycerides, free amino acids, other sugars, etc.) may be determined within the subject, and optionally, feedback may be provided, to the subject based on the determination of such compounds.

In some aspects, the device may be sold together with the drug or other pharmaceutical substance, e.g., as part of a kit. For example, the kit may include a drug or other pharmaceutical substance, and a device able to determine a species within the skin of a subject, e.g., a species indicative of the drug or other pharmaceutical substance, as previously discussed. In other embodiments, however, the device may be sold separately from the drug or other pharmaceutical substance. For example, a doctor or other medical personnel may prescribe a drug (or other pharmaceutical substance) to a subject, and optionally, the doctor or other medical personnel may prescribe a device of the invention, either separately, or together (e.g., as in a kit). In some cases, however, the device itself may be readily available to the subject, e.g., obtainable over-the-counter (OTC) or without a prescription. It should be noted that even if the drug itself requires a prescription, if the device is sold separately (without the drug), it need not necessarily also require a prescription to be purchased. Further examples of kits are discussed in detail below.

As previously discussed, in one set of embodiments, the device is able to deliver and/or withdraw fluid from the skin of a subject, or other mucosal surface, as well as methods of use thereof. In some cases, the device may pierce the skin of the subject, and fluid can then be delivered and or withdrawn from the subject. The subject is usually human, although non-human subjects may be used in certain instances, for instance, other mammals such as a dog, a cat, a horse, a rabbit, a cow, a pig, a sheep, a goat, a rat (e.g., *Rattus norvegicus*), a mouse (e.g., *Mus musculus*), a guinea pig, a hamster, a primate (e.g., a monkey, a chimpanzee, a baboon, an ape, a gorilla, etc.), or the like. If a fluid is withdrawn from the subject, the withdrawn fluid may be any suitable bodily fluid. In one set of embodiments, essentially any body fluid can be used, such as interstitial fluid, other skin-associated material, mucosal material or fluid, whole blood, perspiration and saliva, plasma, or any other bodily fluid.

Non-limiting examples of various devices of the invention are shown in FIG. 1. In FIG. 1A, device 90 is used for withdrawing a fluid from a subject when the device is placed on the skin of a subject. Device 90 includes sensor 95 and fluid transporter 92, e.g., one or more needles or microneedles, etc., as discussed herein. In fluidic communication with fluid transporter 92 via fluidic channel 99 is sensing chamber 97. In some cases, fluid may be withdrawn using fluid transporter 92 by a vacuum, for example, a self-contained vacuum contained within device 90. In one embodiment, sensing chamber 97 may contain agents such as particles, enzymes, dyes, etc., for analyzing bodily fluids, such as interstitial fluid or blood. Optionally, device 90 also contains a display 94 and associated electronics, processors, batteries or other power supplies 93, etc., which may be used to display sensor readings obtained via sensor 95. In addition, device 90 may also optionally contain memory 98 for receiving and storing one or more of sensor readings, calibration data and software for operating a processing element, and transmitters for transmitting a signal indicative of sensor 95 to a receiver, etc. Electronics 93 may include circuitry for receiving and filtering, amplifying or otherwise processing signals from sensor 95, one or more processing elements (e.g., microprocessors, application-specific integrated circuits or other types of information processing hardware) for deriving information including parameter values form the sensor signals, and circuitry for driving the display.

In the example shown in FIG. 1A, device 90 may contain a vacuum source (not shown) that is self-contained within device 90, although in other embodiments, the vacuum source may be external to device 90. (In still other instances, other systems may be used to deliver and/or withdraw fluid from the skin and/or beneath the skin, as is discussed herein.) In one embodiment, after the device is placed on the skin of a subject, the skin may be drawn upward into a recess containing fluid transporter 92, for example, upon exposure to the vacuum source. Access to the vacuum source may be controlled by any suitable method, e.g., by piercing a seal or a septum; by opening a valve or moving a gate, etc. For instance, upon activation of device 90, e.g., by the subject, remotely, automatically, etc., the vacuum source may be put into fluidic communication with the recess such that skin is drawn into the recess containing fluid transporter 92 due to the vacuum. Skin drawn into the recess may come into contact with fluid transporter 92 (e.g., solid or hollow needles or microneedles), which may, in some cases, pierce the skin and allow a fluid to be delivered to and/or withdrawn from the skin and/or beneath the skin. In another embodiment, fluid transporter 92 may be actuated and moved downward to come into contact with the skin, and optionally retracted after use.

Figure 1B:
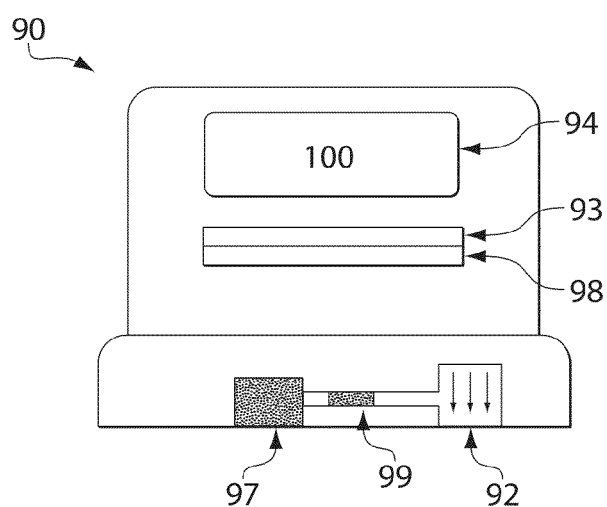

Another non-limiting example of a device is shown in FIG. 1B. This figure illustrates a device useful for delivering a fluid to the subject. Device 90 in this figure includes fluid transporter 92, e.g., one or more needles or microneedles, etc., as discussed herein. In fluidic communication with fluid transporter 92 via fluidic channel 99 is chamber 97, which may contain a drug or other substance to be delivered to the subject. In some cases, fluid may be delivered with a pressure controller, and/or withdrawn using fluid transporter 92 by a vacuum, for example, a self-contained vacuum contained within device 90. For instance, upon creating a vacuum, skin may be drawn up towards fluid transporter 92, and fluid transporter 92 may pierce the skin. Fluid from chamber 97 can then be delivered into or through the skin and/or withdrawn therefrom, through fluid channel 99 and fluid transporter 92. Optionally, device 90 also contains a display 94 (showing "100" in this example) or other device indicator, and associated electronics 93, batteries or other power supplies, etc., which may be used control delivery of fluid to or beneath the skin. In addition, device 90 may also optionally contain memory 98, transmitters for transmitting a signal indicative of device 90 or fluid delivery to a receiver, etc.

Yet another non-limiting example of a device according to some embodiments of the invention is shown in FIG. 2. FIG. 2A illustrates a view of the device (with the cover removed), while FIG. 2B schematically illustrates the device in cross-section. In FIG. 2B, device 50 includes a needle 52 contained within a recess 55. Needle 52 may be solid or hollow, depending on the embodiment, and there may be one or more than one present. Device 50 also includes a self-contained vacuum chamber 60, which wraps around the central portion of the device where needle 52 and recess 55 are located. A channel 62 connects vacuum chamber 60 with recess 55, separated by a foil or a membrane 67. Also shown in device 50 is button 58. When pushed, button 58 breaks foil 67, thereby connecting vacuum chamber 50 with recess 55, creating a vacuum in recess 55. The vacuum may be used, for example, to draw skin into recess 55, preferably such that it contacts needle 52, which then pierces the surface of the skin, thereby gaining access to an internal fluid such as blood or interstitial fluid. The fluid may be controlled, for example, by controlling the size of needle 52, and thereby the depth of penetration. For example, the penetration may be limited to the epidermis, e.g., to collect interstitial fluid, or to the dermis, e.g., to collect blood. In some cases, the vacuum may also be used to at least partially secure device 50 on the surface of the skin, and/or to assist in the withdrawal of fluid from the skin and/or beneath the skin. For instance, fluid may flow into channel 62 under action of the vacuum, and optionally to sensor 61, e.g., for detection of an analyte contained within the fluid. For instance, sensor 61 may produce a color change if an analyte is present, or otherwise produce a detectable signal.

Other components may be added to the example of the device illustrated in FIG. 2, in some embodiments of the invention. For example, device 50 may contain a cover, displays, ports, transmitters, sensors, A/D converters, chambers such as microfluidic chambers, channels such as microfluidic channels, and/or various electronics, e.g., to control or monitor fluid transport into or out of device 50, to determine an analyte present within a fluid delivered to and/or withdrawn from the skin and/or beneath the skin, to determine the status of the device, to report or transmit information regarding the device and/or analytes, or the like, as is discussed in more detail herein. As another example, device 50 may contain an adhesive, e.g., on surface 54, for adhesion of the device to the skin.

Figure 2A:
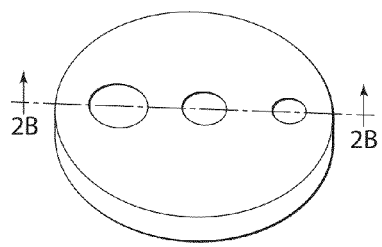
FIGS. 2A-2C illustrate devices according to various embodiments of the invention.
Figure 2B:
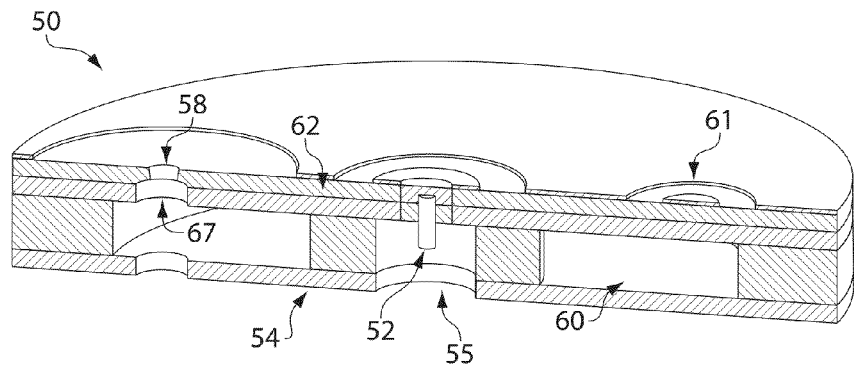
Figure 2C:
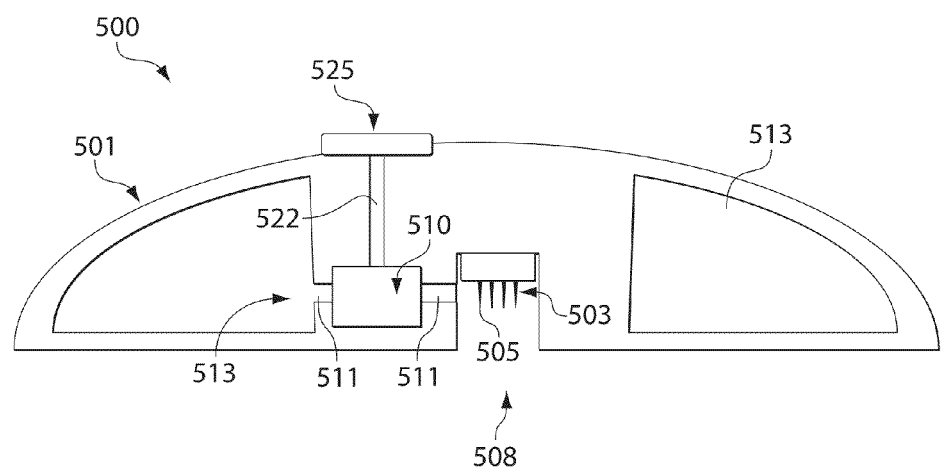

Yet another non-limiting example is illustrated with reference to FIG. 2C. In this example, device 500 includes a support structure 501, and an associated fluid transporter system 503. Fluid transporter system 503 includes one or more needles or microneedles 505, although other fluid transporters as discussed herein may also be used. Also shown in FIG. 2C is sensor 510, connected via channels 511 to recess 508 containing one or more needles or microneedles 505. Chamber 513 may be a self-contained vacuum chamber, and chamber 513 may be in fluidic communication with recess 508 via channel 511, for example, as controlled by a controller or an actuator (not shown). In this figure, device 500 also contains display 525, which is connected to sensor 510 via electrical connection 522. As an example of use of device 500, when fluid is drawn from the skin and/or beneath the skin (e.g., blood, interstitial fluid, etc.), the fluid may flow through channel 511 to be determined by sensor 510, e.g., due to action of the vacuum from vacuum chamber 513. In some cases, the vacuum is used, for example, to draw skin into recess 508, preferably such that it contacts one or more needles or microneedles 505 and pierces the surface of the skin to gain access to a fluid internal of the subject, such as blood or interstitial fluid, etc. The fluid may be controlled, for example, by controlling the size of needle 52, and thereby the depth of penetration. For example, the penetration may be limited to the epidermis, e.g., to collect interstitial fluid, or to the dermis, e.g., to collect blood. Upon determination of the fluid and/or an analyte present or suspected to be present within the fluid, a microprocessor or other controller may display on display 525 a suitable signal. As is discussed below, a display is shown in this figure by way of example only; in other embodiments, no display may be present, or other signals may be used, for example, lights, smell, sound, feel, taste, or the like.

In some cases, more than one fluid transporter system may be present within the device. For instance, the device may be able to be used repeatedly, and/or the device may be able to deliver and/or withdraw fluid at more than one location on a subject, e.g., sequentially and/or simultaneously. As a specific example, in one set of embodiments, the device may include one or more needles, for instance, arranged in an array. In some embodiments, one or more of the needles may be a microneedle. In some cases, the device may be able to simultaneously deliver to and withdraw fluid from a subject. A non-limiting example of a device having more than one fluid transporter system is illustrated with reference to FIG. 2E. In this example, device 500 contains a plurality of structures such as those described herein for delivering and/or withdrawing fluid from a subject, e.g., to and/or from the skin and/or beneath the skin of the subject. For example, device 500 in this example contains 3 such units, although any number of units are possible in other embodiments. In this example, device 500 contains three such fluid transporter systems 575. Each of these fluid transporter systems may independently have the same or different structures, depending on the particular application, and they may have structures such as those described herein.

In some embodiments, the device may take the form of a skin "patch." Typically, a skin patch includes one or more layers of material that are adhered to the surface of the skin, and can be applied by the subject or another person. In certain embodiments, layers or portions of the skin patch may be removed, leaving other layers or portions behind on the skin. Often, the skin patch lacks an external power source, although the various layers of the patch may contain various chemicals, such as drugs, therapeutic agents, diagnostic agents, reaction entities, etc. In some cases, the skin patch may also include mechanical elements as well, for example, a cutter such as is discussed herein.

As another example, the device may be a handheld device that is applied to the surface of the skin of a subject. In some cases, however, the device may be sufficiently small or portable that the subject can self-administer the device. In certain embodiments, the device may also be powered. In some instances, the device may be applied to the surface of the skin, and is not inserted into the skin. In other embodiments, however, at least a portion of the device may be inserted into the skin, for example, mechanically. For example, in one embodiment, the device may include a cutter, such as a hypodermic needle, a knife blade, a piercing element (e.g., a solid or hollow needle), or the like, as discussed herein.

In some cases, the device may be designed such that portions of the device are separable. For example, a first portion of the device may be removed from the surface of the skin, leaving other portions of the device behind on the skin. In one embodiment, a stop may also be included to prevent or control the depth to which the cutter or other device inserts into the skin, e.g., to control penetration to the epidermis, dermis, etc.

Accordingly, as described herein, devices of the invention can be single-stage or multi-stage in some cases. That is, the device can define a single unit that includes one or more components integrally connected to each other which cannot readily be removed from each other by a user, or the device can include one or more components which are designed to be and can readily be removed from each other. As a non-limiting example of the latter, a two-stage patch can be provided for application to the skin of a subject. The patch can include a first stage designed to reside proximate the skin of the subject for the duration of the analysis, which might include an analysis region, a reservoir or other material for creating vacuum or otherwise promoting the flow of fluid or other materials relative to the analysis region, one or more needles or microneedles, or other fluid transporters, to access interstitial fluid via suction blister or without a suction blister or the like.

A second stage or portion of the device can be provided that can initiate operation of the device. For example, a two stage device can be applied to the skin of a subject. A button, switch, or other actuator associated with the second portion of the device can be activated by the subject to cause insertion of one or more needles or microneedles or other fluid transporters to the skin of the subject, or the like. Then, the second stage can be removed, e.g., by the subject or another person, and the first stage can remain on the skin of the subject to facilitate analysis. In another arrangement, a two-stage device can be provided where the first stage includes visualization or other signal-producing components and the second stage includes components necessary to facilitate the analysis, e.g., the second stage can include all components necessary to access bodily fluid, transport the fluid (if necessary) to a site of analysis, and the like, and that stage can be removed, leaving only a visualization stage for the subject or another entity to view or otherwise analyze as described herein.

Any or all of the arrangements described herein can be provided proximate a subject, for example on or proximate the skin of a subject, in various aspects. Activation of the devices can be carried out in a variety of ways, e.g., as described herein. For example, an on-skin device can be in the form of a patch or the like, optionally including multiple layers for activation, sensing, fluid flow, etc. In one embodiment, a patch or a device can be applied to a subject and a region of the patch or device activated (e.g., pushed, pressed, or tapped by a user) to inject a needle or a microneedle, or other fluid transporter, so as to access interstitial fluid or blood. The same or a different activation action, e.g., tapping or pushing action, can activate a vacuum source, open and/or close one or more of a variety of valves, or the like. The device can be a simple one in which it is applied to the skin and operates automatically (where e.g., application of the device to the skin allows access to interstitial fluid or blood and delivers and/or withdraws fluid such as blood or interstitial fluid, e.g., into an analysis region) or the patch or other device can be applied to the skin and one tapping or other activation can cause fluid to flow through administration of one or more needles or microneedles (or other fluid transporter), opening of a valve, activation of vacuum, or any combination thereof. Any number of activation protocols can be carried out by a user repeatedly pushing, tapping, etc. a location or selectively, sequentially, and/or periodically activating a variety of switches (e.g., tapping regions of a patch). With this description, those of ordinary skill in the art can understand how any of the assays described above with respect to one and two can be facilitated.

In another arrangement, activation of one or more needles or microneedles, creation of suction blisters, opening and/or closing of valves, and other techniques to facilitate delivery and/or withdraw of a fluid can be carried out electronically or in other manners facilitated by the subject or by an outside controlling entity (e.g., another user of the device). For example, a device or patch can be provided proximate the skin of a subject and a radio frequency, electromagnetic, or other signal can be provided by a nearby controller or a distant source to activate any of the needles, fluid transporters, blister devices, valves, or other components of the devices described so that any delivery and/or withdrawal of a fluid, and/or any assay or assays can be carried out as desired.

As discussed, various devices of the invention include various systems and methods for delivering to and/or withdrawing fluid from the skin and/or beneath the skin of the subject, according to certain embodiments. For instance, the device may comprise a needle such as a hypodermic needle, a vacuum source, a hygroscopic agent, or the like. Non-limiting examples of suitable delivery techniques include, but are not limited to, injection (e.g., using needles such as hypodermic needles) or a jet injector, such as those discussed below. For instance, in one embodiment, the fluid is delivered and/or withdrawn manually, e.g., by manipulating a plunger on a syringe. In another embodiment, the fluid can be delivered to and/or withdrawn from the skin and/or beneath the skin mechanically or automatically, e.g., using a piston pump or the like. Fluid may also be withdrawn using vacuums such as those discussed herein. For example, vacuum may be applied to a conduit, such as a needle, in fluidic communication with a bodily fluid in order to draw up at least a portion of the fluid from the skin. In yet another embodiment, fluid is withdrawn using capillary action (e.g., using a microfluidic channel or a hypodermic needle having a suitably narrow inner diameter). In still another embodiment, pressure may be applied to force fluid out of the needle.

In some cases, as discussed below, pooled regions of fluid may be created in the skin for facilitating delivery to and/or withdrawal of fluid from the skin. For instance, fluid may be pooled within the skin that is drawn from the surrounding dermal and/or epidermal layers within the skin. The fluid may include interstitial fluid or blood. In other cases, however, no pooling is necessary for the delivery to and/or withdraw of fluid from the skin.

For instance, fluids withdrawn from the skin and/or from beneath the skin of the subject will often contain various analytes from within the body that are important for diagnostic purposes, for example, markers for various disease states, such as glucose (e.g., for diabetics); other example analytes include ions such as sodium, potassium, chloride, calcium, magnesium, and/or bicarbonate (e.g., to determine dehydration); gases such as carbon dioxide or oxygen; $H^+$ (i.e., pH); metabolites such as urea, blood urea nitrogen or creatinine; hormones such as estradiol, estrone, progesterone, progestin, testosterone, androstenedione, etc. (e.g., to determine pregnancy, illicit drug use, or the like); or cholesterol. Other examples include insulin, or hormone levels. Still other analytes include, but not limited to, high-density lipoprotein ("HDL"), low-density lipoprotein ("LDL"), albumin, alanine transaminase ("ALT"), aspartate transaminase ("AST"), alkaline phosphatase ("ALP"), bilirubin, lactate dehydrogenase, etc. (e.g., for liver function tests); luteinizing hormone or beta-human chorionic gonadotrophin (hCG) (e.g., for fertility tests); prothrombin (e.g., for coagulation tests); troponin, BNT or B-type natriuretic peptide, etc., (e.g., as cardiac markers); infectious disease markers for the flu, respiratory syncytial virus or RSV, etc.; or the like.

As discussed herein, certain embodiments of the present invention are generally directed at methods for withdrawing fluids from the body, and optionally determining one or more analytes within the withdrawn fluid. Thus, in some embodiments, at least a portion of the fluid may be stored, and/or analyzed to determine one or more analytes, e.g., a marker for a disease state, or the like, e.g., to allow for the monitoring of the state of disease in a subject. The fluid withdrawn from the skin and/or beneath the skin may be subjected to such uses, and/or one or more materials previously delivered to the skin may be subject to such uses.

In other embodiments, fluid may be delivered to the skin of the subject, and such fluids may contain materials useful for delivery, e.g., forming at least a portion of the fluid, dissolved within the fluid, carried by the fluid (e.g., suspended or dispersed), or the like. Examples of suitable materials include, but are not limited to, particles such as microparticles or nanoparticles, a chemical, a drug or a pharmaceutical substance, a diagnostic agent, a carrier, or the like.

As used herein, the term "fluid" generally refers to a substance that tends to flow and to conform to the outline of its container. Typically, fluids are materials that are unable to withstand a static shear stress, and when a shear stress is applied, the fluid experiences a continuing and permanent distortion. The fluid may have any suitable viscosity that permits at least some flow of the fluid. Non-limiting examples of fluids include liquids and gases, but may also include free-flowing solid particles, viscoelastic fluids, and the like. For example, the fluid may include a flowable matrix or a gel, e.g., formed from biodegradable and/or biocompatible material such as polylactic acid, polyglycolic acid, poly(lactic-co-glycolic acid), etc., or other similar materials.

In some cases, fluids or other materials delivered to the subject may be used for indication of a past, present and/or future condition of the subject. Thus, the condition of the subject to be determined may be one that is currently existing in the subject, and/or one that is not currently existing, but the subject is susceptible or otherwise is at an increased risk to that condition. The condition may be a medical condition, e.g., diabetes or cancer, or other physiological conditions, such as dehydration, pregnancy, illicit drug use, or the like. Additional non-limiting examples are discussed herein. In one set of embodiments, the materials may include a diagnostic agent, for example, one which can determine an analyte within the subject, e.g., one that is a marker for a disease state. As a specific non-limiting example, fluid delivered to the skin and/or beneath the skin of a subject may include a particle including an antibody directed at a marker produced by a bacterium.

In other cases, however, fluids or other materials delivered to the subject may be used to determine conditions that are external to the subject. For example, the fluids or other materials may contain reaction entities able to recognize pathogens or other environmental conditions surrounding the subject, for example, an antibody able to recognize an external pathogen (or pathogen marker). As a specific example, the pathogen may be anthrax and the antibody may be an antibody to anthrax spores. As another example, the pathogen may be a Plasmodia (some species of which causes malaria) and the antibody may be an antibody that recognizes the Plasmodia.

According to one set of embodiments, many devices as discussed herein use various techniques for delivering to and/or withdrawing fluid from the skin and/or from beneath the skin, for example, in connection with fluid transporters, substance transfer components, microinsertion objects, or the like. For example, one or more needles and/or microneedles, a hygroscopic agent, a cutter or other piercing element, an electrically-assisted system, or the like may be used in conjunction with any device described herein. Additional examples of such techniques are described herein and/or in the applications incorporated herein. It is to be understood that, generally, fluids may be delivered and/or withdrawn in a variety of ways, and various systems and methods for delivering to and/or withdrawing fluid from the skin and/or beneath the skin are discussed below and/or in the applications incorporated herein. In one set of embodiments, techniques for piercing or altering the surface of the skin to transport a fluid are discussed, for example, using a needle such as a hypodermic needle or one or more microneedles, chemicals applied to the skin (e.g., penetration enhancers), or jet injectors or other techniques such as those discussed below.

As an example, in one method, a needle such as a hypodermic needle can be used to deliver and/or withdraw fluid to or from the skin and/or beneath the skin. Hypodermic needles are well-known to those of ordinary skill in the art, and can be obtained commercially with a range of needle gauges. For example, the needle may be in the 20-30 gauge range, or the needle may be 32 gauge, 33 gauge, 34 gauge, etc.

If needles are present, there may be one or more needles, the needles may be of any suitable size and length, and the needles may each be solid or hollow. The needles may have any suitable cross-section (e.g., normal or perpendicular to the direction of penetration), for example, circular, square, oval, elliptical, rectangular, rounded rectangle, triangular, polygonal, hexagonal, irregular, etc. For example, the needle may have a length of less than about 5 mm, less than about 4 mm, less than about 3 mm, less than about 2 mm, less than about 1 mm, less than about 800 micrometers, less than 600 micrometers, less than 500 micrometers, less than 400 micrometers, less than about 300 micrometers, less than about 200 micrometers, less than about 175 micrometers, less than about 150 micrometers, less than about 125 micrometers, less than about 100 micrometers, less than about 75 micrometers, less than about 50 micrometers, less than about 10 micrometers, etc. The needle may also have a largest cross-sectional dimension of less than about 5 mm, less than about 4 mm, less than about 3 mm, less than about 2 mm, less than about 1 mm, less than about 800 micrometers, less than 600 micrometers, less than 500 micrometers, less than 400 micrometers, less than about 300 micrometers, less than about 200 micrometers, less than about 175 micrometers, less than about 150 micrometers, less than about 125 micrometers, less than about 100 micrometers, less than about 75 micrometers, less than about 50 micrometers, less than about 10 micrometers, etc. For example, in one embodiment, the needle may have a rectangular cross section having dimensions of 175 micrometers by 50 micrometers. In one set of embodiments, the needle may have an aspect ratio of length to largest cross-sectional dimension of at least about 2:1, at least about 3:1, at least about 4:1, at least 5:1, at least about 7:1, at least about 10:1, at least about 15:1, at least about 20:1, at least about 25:1, at least about 30:1, etc.

In one embodiment, the needle is a microneedle. Typically, a microneedle will have an average cross-sectional dimension (e.g., diameter) of less than about a millimeter. It should be understood that references to "needle" or "microneedle" as discussed herein are by way of example and ease of presentation only, and that in any of the various embodiments, more than one needle and/or microneedle may be present.

As an example, microneedles such as those disclosed in U.S. Pat. No. 6,334,856, issued Jan. 1, 2002, titled "Microneedle Devices and Methods of Manufacture and Use Thereof," by Allen, et al., may be used to deliver to and/or withdraw fluids (or other materials) from a subject. The microneedles may be hollow or solid, and may be formed from any suitable material, e.g., metals, ceramics, semiconductors, organics, polymers, and/or composites. Examples include, but are not limited to, medical grade stainless steel, titanium, nickel, iron, gold, tin, chromium, copper, alloys of these or other metals, silicon, silicon dioxide, and polymers, including polymers of hydroxy acids such as lactic acid and glycolic acid polylactide, polyglycolide, polylactide-co-glycolide, and copolymers with polyethylene glycol, polyanhydrides, polyorthoesters, polyurethanes, polybutyric acid, polyvaleric acid, polylactide-co-caprolactone, polycarbonate, polymethacrylic acid, polyethylenevinyl acetate, polytetrafluorethylene, polymethyl methacrylate, polyacrylic acid, or polyesters.

In some cases, more than one needle or microneedle may be used. For example, arrays of needles or microneedles may be used, and the needles or microneedles may be arranged in the array in any suitable configuration, e.g., periodic, random, etc. In some cases, the array may have 3 or more, 4 or more, 5 or more, 10 or more, 15 or more, 20 or more, 35 or more, 50 or more, 100 or more, or any other suitable number of needles or microneedles. In some embodiments, the device may have at least 3 but no more than 5 needles or microneedles (or other fluid transporters), at least 6 but no more than 10 needles or microneedles, or at least 11 but no more than 20 needles or microneedles. Typically, a microneedle will have an average cross-sectional dimension (e.g., diameter) of less than about a micron.

Those of ordinary skill in the art can arrange needles relative to the skin for these purposes including, in one embodiment, introducing needles into the skin at an angle, relative to the skin's surface, other than 90°, i.e., to introduce a needle or needles into the skin in a slanting fashion so as to limit the depth of penetration. In another embodiment, however, the needles may enter the skin at approximately 90°.

In some cases, the needles (or microneedles) may be present in an array selected such that the density of needles within the array is between about 0.5 needles/mm$^2$ and about 10 needles/mm$^2$, and in some cases, the density may be between about 0.6 needles/mm$^2$ and about 5 needles/mm$^2$, between about 0.8 needles/mm$^2$ and about 3 needles/mm$^2$, between about 1 needles/mm$^2$ and about 2.5 needles/mm$^2$, or the like. In some cases, the needles may be positioned within the array such that no two needles are closer than about 1 mm, about 0.9 mm, about 0.8 mm, about 0.7 mm, about 0.6 mm, about 0.5 mm, about 0.4 mm, about 0.3 mm, about 0.2 mm, about 0.1 mm, about 0.05 mm, about 0.03 mm, about 0.01 mm, etc.

In another set of embodiments, the needles (or microneedles) may be chosen such that the area of the needles (determined by determining the area of penetration or perforation on the surface of the skin of the subject by the needles) allows for adequate flow of fluid to or from the skin and/or beneath the skin of the subject. The needles may be chosen to have smaller or larger areas (or smaller or large diameters), so long as the area of contact for the needles to the skin is sufficient to allow adequate blood flow from the skin of the subject to the device. For example, in certain embodiments, the needles may be selected to have a combined skin-penetration area of at least about 500 nm$^2$, at least about 1,000 nm$^2$, at least about 3,000 nm$^2$, at least about 10,000 nm$^2$, at least about 30,000 nm$^2$, at least about 100,000 nm$^2$, at least about 300,000 nm$^2$, at least about 1 microns$^2$, at least about 3 microns$^2$, at least about 10 microns$^2$, at least about 30 microns$^2$, at least about 100 microns$^2$, at least about 300 microns$^2$, at least about 500 microns$^2$, at least about 1,000 microns$^2$, at least about 2,000 microns$^2$, at least about 2,500 microns$^2$, at least about 3,000 microns$^2$, at least about 5,000 microns$^2$, at least about 8,000 microns$^2$, at least about 10,000 microns$^2$, at least about 35,000 microns$^2$, at least about 100,000 microns$^2$, at least about 300,000 microns$^2$, at least about 500,000 microns$^2$, at least about 800,000 microns$^2$, at least about 8,000,000 microns$^2$, etc., depending on the application.

The needles or microneedles may have any suitable length, and the length may be, in some cases, dependent on the application. For example, needles designed to only penetrate the epidermis may be shorter than needles designed to also penetrate the dermis, or to extend beneath the dermis or the skin. In certain embodiments, the needles or microneedles may have a maximum penetration into the skin of no more than about 3 mm, no more than about 2 mm, no more than about 1.75 mm, no more than about 1.5 mm, no more than about 1.25 mm, no more than about 1 mm, no more than about 900 microns, no more than about 800 microns, no more than about 750 microns, no more than about 600 microns, no more than about 500 microns, no more than about 400 microns, no more than about 300 microns, no more than about 200 microns, no more than about 175 micrometers, no more than about 150 micrometers, no more than about 125 micrometers, no more than about 100 micrometers, no more than about 75 micrometers, no more than about 50 micrometers, etc. In certain embodiments, the needles or microneedles may be selected so as to have a maximum penetration into the skin of at least about 50 micrometers, at least about 100 micrometers, at least about 300 micrometers, at least about 500 micrometers, at least about 1 mm, at least about 2 mm, at least about 3 mm, etc.

In one set of embodiments, the needles (or microneedles) may be coated. For example, the needles may be coated with a substance that is delivered when the needles are inserted into the skin. For instance, the coating may comprise heparin, an anticoagulant, an anti-inflammatory compound, an analgesic, an anti-histamine compound, etc. to assist with the flow of blood from the skin of the subject, or the coating may comprise a drug or other pharmaceutical substance such as those described herein. The drug or other pharmaceutical substance may be one used for localized delivery (e.g., of or proximate the region to which the coated needles or microneedles are applied), and/or the drug or other pharmaceutical substance may be one intended for systemic delivery within the subject.

In one embodiment, the fluid is delivered and/or withdrawn manually, e.g., by manipulating a plunger on a syringe. In another embodiment, the fluid can be delivered to and/or withdrawn from the skin and/or beneath the skin mechanically or automatically, e.g., using a piston pump or the like. Fluid may also be withdrawn using vacuums such as those discussed herein. For example, vacuum may be applied to a conduit, such as a needle, in fluidic communication with a bodily fluid in order to draw up at least a portion of the fluid from the skin. In yet another embodiment, fluid is withdrawn using capillary action (e.g., using a microfluidic channel or hypodermic needle having a suitably narrow inner diameter). In still another embodiment, pressure may be applied to force fluid out of the needle.

As still another example, pressurized fluids may be used to deliver fluids or other materials into and/or through the skin, for instance, using a jet injector or a "hypospray." Typically, such devices produce a high-pressure "jet" of liquid or powder (e.g., a biocompatible liquid, such as saline) that drives material into the skin, and the depth of penetration may be controlled, for instance, by controlling the pressure of the jet. The pressure may come from any suitable source, e.g., a standard gas cylinder or a gas cartridge. A non-limiting example of such a device can be seen in U.S. Pat. No. 4,103,684, issued Aug. 1, 1978, titled "Hydraulically Powered Hypodermic Injector with Adapters for Reducing and Increasing Fluid Injection Force," by Ismach. Pressurization of the liquid may be achieved, for example, using compressed air or gas, for instance, from a gas cylinder or a gas cartridge.

In some embodiments, fluid may be withdrawn using a hygroscopic agent applied to the surface of the skin or proximate the skin. For example, a device as described herein may contain a hygroscopic agent. In some cases, pressure may be applied to drive the hygroscopic agent into the skin. Hygroscopic agents typically are able to attract water from the surrounding environment, for instance, through absorption or adsorption. Non-limiting examples of hygroscopic agents include sugar, honey, glycerol, ethanol, methanol, sulfuric acid, methamphetamine, iodine, many chloride and hydroxide salts, and a variety of other substances. Other examples include, but are not limited to, zinc chloride, calcium chloride, potassium hydroxide, or sodium hydroxide. In some cases, a suitable hygroscopic agent may be chosen based on its physical or reactive properties, e.g., inertness or biocompatibility towards the skin of the subject, depending on the application.

In some embodiments, the device may comprise a cutter able to cut or pierce the surface of the skin. The cutter may comprise any mechanism able to create a path through which fluids may be delivered to and/or withdrawn from the skin and/or beneath the skin. For example, the cutter may comprise a hypodermic needle, a blade (e.g., a knife blade, a serrated blade, etc.), a piercing element (e.g., a lancet or a solid or a hollow needle), or the like, which can be applied to the skin to create a suitable conduit for the delivery and/or withdrawal of fluid from the skin and/or from beneath the skin. In one embodiment, a cutter is used to create such a pathway and removed, then fluid may be delivered and/or withdrawn via this pathway. In another embodiment, the cutter remains in place within the skin, and fluid may be delivered and/or withdrawn through a conduit within the cutter.

In some embodiments, fluid may be delivered and/or withdrawn using an electric charge. For example, reverse iontophoresis may be used. Without intending to be bound by any theory, reverse iontophoresis uses a small electric current to drive charged and highly polar compounds across the skin. Since the skin is negatively charged at physiologic pH, it acts as a permselective membrane to cations, and the passage of counterions across the skin induces an electroosmotic solvent flow that may carry neutral molecules in the anode-to-cathode direction. Components in the solvent flow may be analyzed as described elsewhere herein. In some instances, a reverse iontophoresis apparatus may comprise an anode cell and a cathode cell, each in contact with the skin. The anode cell may be filled, for example, with an aqueous buffer solution (i.e., aqueous Tris buffer) having a pH greater than 4 and an electrolyte (i.e. sodium chloride). The cathode cell can be filled with aqueous buffer. As one example, a first electrode (e.g., an anode) can be inserted into the anode cell and a second electrode (e.g., a cathode) can be inserted in the cathode cell. In some embodiments, the electrodes are not in direct contact with the skin.

A current may be applied to induce reverse iontophoresis, thereby withdrawing a fluid from the skin. The current applied may be, for example, greater than 0.01 mA, greater than 0.3 mA, greater than 0.1 mA, greater than 0.3 mA, greater than 0.5 mA, or greater than 1 mA. It should be understood that currents outside these ranges may be used as well. The current may be applied for a set period of time. For example, the current may be applied for greater than 30 seconds, greater than 1 minute, greater than 5 minutes, greater than 30 minutes, greater than 1 hour, greater than 2 hours, or greater than 5 hours. It should be understood that times outside these ranges may be used as well.

In one set of embodiments, the device may comprise an apparatus for ablating the skin. Without wishing to be bound by any theory, it is believed that ablation comprises removing a microscopic patch of stratum corneum (i.e., ablation forms a micropore), thus allowing access to bodily fluids. In some cases, thermal, radiofrequency, and/or laser energy may be used for ablation. In some instances, thermal ablation may be applied using a heating element. Radiofrequency ablation may be carried out using a frequency and energy capable of heating water and/or tissue. A laser may also be used to irradiate a location on the skin to remove a portion. In some embodiments, the heat may be applied in pulses such that a steep temperature gradient exists essentially perpendicular to the surface of the skin. For example, a temperature of at least 100° C., at least 200° C., at least 300° C., or at least 400° C. may be applied for less than 1 second, less than 0.1 seconds, less than 0.01 seconds, less than 0.005 seconds, or less than 0.001 seconds.

In some embodiments, the device may comprise a mechanism for taking a solid sample of tissue. For example, a solid tissue sample may be acquired by methods such as scraping the skin or cutting out a portion. Scraping may comprises a reciprocating action whereby an instrument is scraped along the surface of the skin in two or more directions. Scraping can also be accomplished by a rotating action, for example parallel to the surface of the skin and in one direction (i.e., with a roller drum) or parallel to the surface of the skin and in a circular manner (i.e., with a drilling instrument). A cutting mechanism may comprise a blade capable of making one or more incisions and a mechanism for removing a portion of tissue (i.e., by suction or mechanically picking up) or may use a pincer mechanism for cutting out a portion of tissue. A cutting mechanism may also function by a coring action. For example, a hollow cylindrical device can be penetrated into the skin such that a cylindrical core of tissue may be removed. A solid sample may be analyzed directly or may be liquefied prior to analysis. Liquefaction can comprise treatment with organic solvents, enzymatic solutions, etc.

The device may also contain, in some aspects, a vacuum source. In some cases, the vacuum source is one that is self-contained within the device, i.e., the device need not be connected to an external vacuum source (e.g., a house vacuum) during use of the device to withdraw blood or interstitial fluid from the skin and/or from beneath the skin. For example, in one set of embodiments, the vacuum source may include a vacuum chamber having a pressure less than atmospheric pressure before blood (or other fluid) is withdrawn into the device, i.e., the vacuum chamber is at a "negative pressure" (that is, negative relative to atmospheric pressure) or a "vacuum pressure" (or just having a "vacuum"). For example, the vacuum in the vacuum chamber may be at least about 50 mmHg, at least about 100 mmHg, at least about 150 mmHg, at least about 200 mmHg, at least about 250 mmHg, at least about 300 mmHg, at least about 350 mmHg, at least about 400 mmHg, at least about 450 mmHg, at least about 500 mmHg, at least 550 mmHg, at least 600 mmHg, at least 650 mmHg, at least about 700 mmHg, or at least about 750 mmHg, i.e., below atmospheric pressure. Thus, the pressure within the vacuum is at a "reduced pressure" relative to atmospheric pressure, e.g., the vacuum chamber is a reduced pressure chamber. However, in other embodiments, it should be understood that other pressures may be used and/or that different methods may be used to produce other pressures (greater than or less than atmospheric pressure). As non-limiting examples, an external vacuum or a mechanical device may be used as the vacuum source; various additional examples are discussed in detail herein.

In some embodiments, fluids may be withdrawn from the skin and/or beneath the skin using a vacuum. The vacuum may be an external vacuum source, and/or the vacuum source may be self-contained within the device. For example, vacuums of at least about 50 mmHg, at least about 100 mmHg, at least about 150 mmHg, at least about 200 mmHg, at least about 250 mmHg, at least about 300 mmHg, at least about 350 mmHg, at least about 400 mmHg, at least about 450 mmHg, at least about 500 mmHg, at least 550 mmHg, at least 600 mmHg, at least 650 mmHg, at least about 700 mmHg, or at least about 750 mmHg may be applied to the skin. As used herein, "vacuum" refers to pressures that are below atmospheric pressure.

As mentioned, any source of vacuum may be used. For example, the device may comprise an internal vacuum source, and/or be connectable to a vacuum source is external to the device, such as a vacuum pump or an external (line) vacuum source. In some cases, a vacuum may be created manually, e.g., by manipulating a syringe pump, a plunger, or the like, or the low pressure may be created mechanically or automatically, e.g., using a piston pump, a syringe, a bulb, a Venturi tube, manual (mouth) suction, etc., or the like.

In some cases, the device includes an interface that is able to apply a vacuum to the skin. The interface may be, for example, a suction cup or a circular bowl that is placed on the surface of the skin, and vacuum applied to the interface to create a vacuum. In one set of embodiments, the interface is part of a support structure, as discussed herein. The interface may be formed from any suitable material, e.g., glass, rubber, polymers such as silicone, polyurethane, nitrile rubber, EPDM rubber, neoprene, or the like. In some cases, the seal between the interface and the skin may be enhanced (e.g., reducing leakage), for instance, using vacuum grease, petroleum jelly, a gel, or the like. In some cases, the interface may be relatively small, for example, having a diameter of less than about 5 cm, less than about 4 cm, less than about 3 cm, less than about 2 cm, less than about 1 cm, less than about 5 mm, less than about 4 mm, less than about 3 mm, less than about 2 mm, or less than about 1 mm. The interface may be circular, although other shapes are also possible, for example, square, star-shaped (having 5, 6, 7, 8, 9, 10, 11, etc. points), tear-drop, oval, rectangular, or the like. In some cases, non-circular shapes may be used since high-energy points, e.g., the points or corners of the shape may enhance or accelerate blister formation.

The interface may also be selected, in some cases, to keep the size of the contact region below a certain area, e.g., to minimize pain or discomfort to the subject, for aesthetic reasons, or the like. The interface may be constructed out of any suitable material, e.g., glass, plastic, or the like.

In one set of embodiments, a device of the present invention may not have an external power and/or a vacuum source. In some cases, the device is "pre-loaded" with a suitable vacuum source; for instance, in one embodiment, the device may be applied to the skin and activated in some fashion to create and/or access the vacuum source. As one example, a device of the present invention may be contacted with the skin of a subject, and a vacuum created through a change in shape of a portion of the device (e.g., using a shape memory polymer), or the device may contain one or more sealed, self-contained vacuum chambers, where a seal is punctured in some manner to create a vacuum. For instance, upon puncturing the seal, a vacuum compartment may be in fluidic communication with one or more needles, which can be used to move the skin towards the device, withdraw fluid from the skin and/or beneath the skin, or the like.

As another example, a shape memory polymer may be shaped to be flat at a first temperature (e.g., room temperature) but curved at a second temperature (e.g., body temperature), and when applied to the skin, the shape memory polymer may alter from a flat shape to a curved shape, thereby creating a vacuum. As yet another example, a mechanical device may be used to create the vacuum, For example, springs, coils, expanding foam (e.g., from a compressed state), a shape memory polymer, shape memory metal, or the like may be stored in a compressed or wound released upon application to a subject, then released (e.g., unwinding, uncompressing, etc.), to mechanically create the vacuum. Non-limiting examples of shape-memory polymers and metals include Nitinol, compositions of oligo(epsilon-caprolactone)diol and crystallizable oligo(rho-dioxanone)diol, or compositions of oligo(epsilon-caprolactone)dimethacrylate and n-butyl acrylate.

In yet another example, a chemical reaction may be used to create a vacuum, e.g., a reaction in which a gas is produced, which can be harnessed to provide the mechanical force to create a vacuum. In some embodiments, the device may be used to create a vacuum automatically, once activated, without any external control by a user.

In some cases, the device may be an electrical and/or a mechanical device applicable or affixable to the surface of the skin, e.g., using a vacuum, an adhesive, or a combination of adhesives, or other techniques such as those described herein. For example, in one set of embodiments, the device may include a support structure that contains an adhesive that can be used to immobilize the device to the skin. The adhesive may be permanent or temporary, and may be used to affix the device to the surface of the skin. The adhesive may be any suitable adhesive, for example, a pressure sensitive adhesive, a contact adhesive, a permanent adhesive, a cyanoacrylate, glue, gum, hot melts, an epoxy, a hydrogel, a hydrocolloid, or the like. In some cases, the adhesive is chosen to be biocompatible or hypoallergenic.

In another set of embodiments, the device may be mechanically held to the skin. For instance, the device may include mechanical elements such as straps, belts, buckles, strings, ties, elastic bands, or the like. For example, a strap may be worn around the device to hold the device in place against the skin of the subject. In yet another set of embodiments, a combination of these and/or other techniques may be used. As one non-limiting example, the device may be affixed to a subject's arm or leg using adhesive and a strap.

In some aspects, the device may include a support structure for application to the skin of the subject. The support structure may be used, as discussed herein, for applying the fluid transporter to the surface of the skin of the subject, e.g., so that fluid may be delivered to and/or withdrawn from the skin and/or beneath the skin of the subject. In some cases, the support structure may immobilize the fluid transporter such that the fluid transporter cannot move relative to the support structure; in other cases, however, the fluid transporter may be able to move relative to the support structure. In one embodiment, as a non-limiting example, the fluid transporter is immobilized relative to the support structure, and the support structure is positioned within the device such that application of the device to the skin causes at least a portion of the fluid transporter to pierce the skin of the subject. In some cases, as discussed herein, the support structure includes a reversibly deformable structure.

For instance, in one set of embodiments, the support structure, or a portion of the support structure, may move from a first position to a second position. For example, the first position may be one where the support structure has immobilized relative thereto a fluid transporter that does not contact the skin (e.g., the fluid transporter may be contained within a recess), while the second position may be one where the fluid transporter does contact the skin, and in some cases, the fluid transporter may pierce the skin. The support structure may be moved using any suitable technique, e.g., manually, mechanically, electromagnetically, using a servo mechanism, or the like. In one set of embodiments, for example, the support structure may be moved from a first position to a second position by pushing a button on the device, which causes the support structure to move (either directly, or indirectly, e.g., through a mechanism linking the button with the support structure). Other mechanisms (e.g., dials, levers, sliders, etc., as discussed herein) may be used in conjunction with or instead of a button. In another set of embodiments, the support structure may be moved from a first position to a second position automatically, for example, upon activation by a computing device, upon remote activation, after a period of time has elapsed, or the like. For example, in one embodiment, a servo connected to the support structure is activated electronically, moving the support structure from the first position to the second position.

In some cases, the support structure may also be moved from the second position to the first position. For example, after fluid has been delivered to and/or withdrawn from the skin and/or beneath the skin, e.g., using a fluid transporter the support structure may be moved, which may move the fluid transporter away from contact with the skin. The support structure may be moved from the second position to the first position using any suitable technique, including those described above, and the technique for moving the support structure from the second position to the first position may be the same or different as that moving the support structure from the first position to the second position.

In some cases, the support structure may be able to draw skin towards the fluid transporter. For example, in one set of embodiments, the support structure may include a vacuum interface, such as is described herein. The interface may be connected with a vacuum source (external and/or internal to the device), and when a vacuum is applied, skin may be drawn towards the support structure, e.g., for contact with a fluid transporter, such as a needle or a microneedle.

In certain aspects, the device may also contain an activator. The activator may be constructed and arranged to cause exposure of the fluid transporter to the skin upon activation of the activator. For example, the activator may cause a chemical to be released to contact the skin, one or more needles or microneedle to be driven into the skin, a vacuum to be applied to the skin, a jet of fluid to be directed to the skin, or the like. The activator may be activated by the subject, and/or by another person (e.g., a health care provider), or the device itself may be self-activating, e.g., upon application to the skin of a subject. The activator may be activated once, or multiple times in some cases.

The device may be activated, for example, by pushing a button, flipping a switch, moving a slider, turning a dial, or the like. The subject, and/or another person, may activate the activator. In some cases, the device may be remotely activated. For example, a health care provider may send an electromagnetic signal which is received by the device in order to activate the device, e.g., a wireless signal, a Bluetooth signal, an Internet signal, a radio signal, etc.

In some aspects, the device may include channels such as microfluidic channels, which may be used to deliver and/or withdraw fluids and/or other materials from the skin and/or beneath the skin. In some cases, the microfluidic channels are in fluid communication with a fluid transporter that is used to deliver to and/or withdraw fluids from the skin and/or beneath the skin. For example, in one set of embodiments, the device may include a hypodermic needle or other needle (e.g., one or more microneedles) that can be inserted into the skin, and fluid may be delivered into or through the skin via the needle and/or withdrawn from the skin via the needle. The device may also include one or more microfluidic channels to contain fluid for delivery to the needle, e.g., from a source of fluid, and/or to withdraw fluid withdrawn from the skin and/or beneath the skin, e.g., for delivery to an analytical chamber within the device, to a reservoir for later analysis, or the like.

In some cases, more than one chamber may be present within the device, and in some cases, some or all of the chambers may be in fluidic communication, e.g., via channels such as microfluidic channels. In various embodiments, a variety of chambers and/or channels may be present within the device, depending on the application. For example, the device may contain chambers for sensing an analyte, chambers for holding reagents, chambers for controlling temperature, chambers for controlling pH or other conditions, chambers for creating or buffering pressure or vacuum, chambers for controlling or dampening fluid flow, mixing chambers, or the like.

Thus, in one set of embodiments, the device may include a microfluidic channel. As used herein, "microfluidic," "microscopic," "microscale," the "micro-" prefix (for example, as in "microchannel"), and the like generally refers to elements or articles having widths or diameters of less than about 1 mm, and less than about 100 microns (micrometers) in some cases. In some embodiments, larger channels may be used instead of, or in conjunction with, microfluidic channels for any of the embodiments discussed herein. For examples, channels having widths or diameters of less than about 10 mm, less than about 9 mm, less than about 8 mm, less than about 7 mm, less than about 6 mm, less than about 5 mm, less than about 4 mm, less than about 3 mm, or less than about 2 mm may be used in certain instances. In some cases, the element or article includes a channel through which a fluid can flow. In all embodiments, specified widths can be a smallest width (i.e. a width as specified where, at that location, the article can have a larger width in a different dimension), or a largest width (i.e. where, at that location, the article has a width that is no wider than as specified, but can have a length that is greater). Thus, for instance, the microfluidic channel may have an average cross-sectional dimension (e.g., perpendicular to the direction of flow of fluid in the microfluidic channel) of less than about 1 mm, less than about 500 microns, less than about 300 microns, or less than about 100 microns. In some cases, the microfluidic channel may have an average diameter of less than about 60 microns, less than about 50 microns, less than about 40 microns, less than about 30 microns, less than about 25 microns, less than about 10 microns, less than about 5 microns, less than about 3 microns, or less than about 1 micron.

A "channel," as used herein, means a feature on or in an article (e.g., a substrate) that at least partially directs the flow of a fluid. In some cases, the channel may be formed, at least in part, by a single component, e.g. an etched substrate or molded unit. The channel can have any cross-sectional shape, for example, circular, oval, triangular, irregular, square or rectangular (having any aspect ratio), or the like, and can be covered or uncovered (i.e., open to the external environment surrounding the channel). In embodiments where the channel is completely covered, at least one portion of the channel can have a cross-section that is completely enclosed, and/or the entire channel may be completely enclosed along its entire length with the exception of its inlet and outlet.

A channel may have an aspect ratio (length to average cross-sectional dimension), e.g., an aspect ratio of at least about 2:1, more typically at least about 3:1, at least about 5:1, at least about 10:1, etc. As used herein, a "cross-sectional dimension," in reference to a fluidic or microfluidic channel, is measured in a direction generally perpendicular to fluid flow within the channel. A channel generally will include characteristics that facilitate control over fluid transport, e.g., structural characteristics and/or physical or chemical characteristics (hydrophobicity vs. hydrophilicity) and/or other characteristics that can exert a force (e.g., a containing force) on a fluid. The fluid within the channel may partially or completely fill the channel. In some cases the fluid may be held or confined within the channel or a portion of the channel in some fashion, for example, using surface tension (e.g., such that the fluid is held within the channel within a meniscus, such as a concave or convex meniscus). In an article or substrate, some (or all) of the channels may be of a particular size or less, for example, having a largest dimension perpendicular to fluid flow of less than about 5 mm, less than about 2 mm, less than about 1 mm, less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 nm, or less than about 10 nm or less in some cases. In one embodiment, the channel is a capillary.

In some cases, the device may contain one or more chambers or reservoirs for holding fluid. In some cases, the chambers may be in fluidic communication with one or more fluid transporters and/or one or more microfluidic channels. For instance, the device may contain a chamber for collecting fluid withdrawn from a subject (e.g., for storage and/or later analysis), a chamber for containing a fluid for delivery to the subject (e.g., blood, saline, optionally containing drugs, hormones, vitamins, pharmaceutical agents, or the like), etc.

A variety of materials and methods, according to certain aspects of the invention, can be used to form the device, e.g., microfluidic channels, chambers, etc. For example, various components of the invention can be formed from solid materials, in which the channels can be formed via micromachining, film deposition processes such as spin coating and chemical vapor deposition, laser fabrication, photolithographic techniques, etching methods including wet chemical or plasma processes, and the like. See, for example, *Scientific American*, 248:44-55, 1983 (Angell, et al).

In one set of embodiments, various components of the systems and devices of the invention can be formed of a polymer, for example, an elastomeric polymer such as polydimethylsiloxane ("PDMS"), polytetrafluoroethylene ("PTFE" or Teflon®), or the like. For instance, according to one embodiment, a microfluidic channel may be implemented by fabricating the fluidic system separately using PDMS or other soft lithography techniques (details of soft lithography techniques suitable for this embodiment are discussed in the references titled "Soft Lithography," by Younan Xia and George M. Whitesides, published in the *Annual Review of Material Science*, 1998, Vol. 28, pages 153-184, and "Soft Lithography in Biology and Biochemistry," by George M. Whitesides, Emanuele Ostuni, Shuichi Takayama, Xingyu Jiang and Donald E. Ingber, published in the *Annual Review of Biomedical Engineering*, 2001, Vol. 3, pages 335-373; each of these references is incorporated herein by reference).

Other examples of potentially suitable polymers include, but are not limited to, polyethylene terephthalate (PET), polyacrylate, polymethacrylate, polycarbonate, polystyrene, polyethylene, polypropylene, polyvinylchloride, cyclic olefin copolymer (COC), polytetrafluoroethylene, a fluorinated polymer, a silicone such as polydimethylsiloxane, polyvinylidene chloride, bis-benzocyclobutene ("BCB"), a polyimide, a polyester, a fluorinated derivative of a polyimide, or the like. Another example is polyethylene terephthalate glycol ("PETG"). In PETG, the ethylene glycol group that is normally part of the PET chain is partially substituted for cyclohexane dimethanol (e.g., approximately 15-35 mol % of the ethylene groups are replaced), which may, in some cases, slow down the crystallization of the polymer when injection molded to allow better processing. Combinations, copolymers, derivatives, or blends involving polymers including those described above are also envisioned. The device may also be formed from composite materials, for example, a composite of a polymer and a semiconductor material.

In some embodiments, various components of the invention are fabricated from polymeric and/or flexible and/or elastomeric materials, and can be conveniently formed of a hardenable fluid, facilitating fabrication via molding (e.g. replica molding, injection molding, cast molding, etc.). The hardenable fluid can be essentially any fluid that can be induced to solidify, or that spontaneously solidifies, into a solid capable of containing and/or transporting fluids contemplated for use in and with the fluidic network. In one embodiment, the hardenable fluid comprises a polymeric liquid or a liquid polymeric precursor (i.e. a "prepolymer"). Suitable polymeric liquids can include, for example, thermoplastic polymers, thermoset polymers, waxes, metals, or mixtures or composites thereof heated above their melting point. As another example, a suitable polymeric liquid may include a solution of one or more polymers in a suitable solvent, which solution forms a solid polymeric material upon removal of the solvent, for example, by evaporation. Such polymeric materials, which can be solidified from, for example, a melt state or by solvent evaporation, are well known to those of ordinary skill in the art. A variety of polymeric materials, many of which are elastomeric, are suitable, and are also suitable for forming molds or mold masters, for embodiments where one or both of the mold masters is composed of an elastomeric material. A non-limiting list of examples of such polymers includes polymers of the general classes of silicone polymers, epoxy polymers, and acrylate polymers. Epoxy polymers are characterized by the presence of a three-membered cyclic ether group commonly referred to as an epoxy group, 1,2-epoxide, or oxirane. For example, diglycidyl ethers of bisphenol A can be used, in addition to compounds based on aromatic amine, triazine, and cycloaliphatic backbones. Another example includes the well-known Novolac polymers. Non-limiting examples of silicone elastomers suitable for use according to the invention include those formed from precursors including the chlorosilanes such as methylchlorosilanes, ethylchlorosilanes, phenylchlorosilanes, etc.

Silicone polymers are used in certain embodiments, for example, the silicone elastomer polydimethylsiloxane. Non-limiting examples of PDMS polymers include those sold under the trademark Sylgard by Dow Chemical Co., Midland, Mich., and particularly Sylgard 182, Sylgard 184, and Sylgard 186. Silicone polymers including PDMS have several beneficial properties simplifying fabrication of the microfluidic structures of the invention. For instance, such materials are inexpensive, readily available, and can be solidified from a prepolymeric liquid via curing with heat. For example, PDMSs are typically curable by exposure of the prepolymeric liquid to temperatures of about, for example, about 65° C. to about 75° C. for exposure times of, for example, about an hour. Also, silicone polymers, such as PDMS, can be elastomeric and thus may be useful for forming very small features with relatively high aspect ratios, necessary in certain embodiments of the invention. Flexible (e.g., elastomeric) molds or masters can be advantageous in this regard.

One advantage of forming structures such as microfluidic structures of the invention from silicone polymers, such as PDMS, is the ability of such polymers to be oxidized, for example by exposure to an oxygen-containing plasma such as an air plasma, so that the oxidized structures contain, at their surface, chemical groups capable of cross-linking to other oxidized silicone polymer surfaces or to the oxidized surfaces of a variety of other polymeric and non-polymeric materials. Thus, components can be fabricated and then oxidized and essentially irreversibly sealed to other silicone polymer surfaces, or to the surfaces of other substrates reactive with the oxidized silicone polymer surfaces, without the need for separate adhesives or other sealing means. In most cases, sealing can be completed simply by contacting an oxidized silicone surface to another surface without the need to apply auxiliary pressure to form the seal. That is, the pre-oxidized silicone surface acts as a contact adhesive against suitable mating surfaces. Specifically, in addition to being irreversibly sealable to itself, oxidized silicone such as oxidized PDMS can also be sealed irreversibly to a range of oxidized materials other than itself including, for example, glass, silicon, silicon oxide, quartz, silicon nitride, polyethylene, polystyrene, glassy carbon, and epoxy polymers, which have been oxidized in a similar fashion to the PDMS surface (for example, via exposure to an oxygen-containing plasma). Oxidation and sealing methods useful in the context of the present invention, as well as overall molding techniques, are described in the art, for example, in an article titled "Rapid Prototyping of Microfluidic Systems and Polydimethylsiloxane," *Anal. Chem.*, 70:474-480, 1998 (Duffy et al.), incorporated herein by reference.

Another advantage to forming microfluidic structures of the invention (or interior, fluid-contacting surfaces) from oxidized silicone polymers is that these surfaces can be much more hydrophilic than the surfaces of typical elastomeric polymers (where a hydrophilic interior surface is desired). Such hydrophilic channel surfaces can thus be more easily filled and wetted with aqueous solutions than can structures comprised of typical, unoxidized elastomeric polymers or other hydrophobic materials.

In one set of embodiments, the device may include a sensor, for example embedded within or integrally connected to the device, or positioned remotely but with physical, electrical, and/or optical connection with the device so as to be able to sense a chamber within or fluid from the device. For example, the sensor may be in fluidic communication with fluid withdrawn from a subject, directly, via a microfluidic channel, an analytical chamber, etc. The sensor may be able to sense an analyte, e.g., one that is suspected of being in a fluid withdrawn from a subject. For example, a sensor may be free of any physical connection with the device, but may be positioned so as to detect the results of interaction of electromagnetic radiation, such as infrared, ultraviolet, or visible light, which has been directed toward a portion of the device, e.g., a chamber within the device. As another example, a sensor may be positioned on or within the device, and may sense activity in a chamber by being connected optically to the chamber. Sensing communication can also be provided where the chamber is in communication with a sensor fluidly, optically or visually, thermally, pneumatically, electronically, or the like, so as to be able to sense a condition of the chamber. As one example, the sensor may be positioned downstream of a chamber, within a channel such a microfluidic channel, on an external apparatus, or the like. Accordingly, the device, in certain embodiments, may contain a portion able to determine a fluid removed from the skin. For example, a portion of the device may contain a sensor(s), or reagents able to interact with an analyte contained or suspected to be present within the withdrawn fluid from the skin of the subject, for example, a marker for a disease state The sensor may be or include, for example, a pH sensor, an optical sensor, an oxygen sensor, a sensor able to detect the concentration of a substance, or the like. Non-limiting examples of sensors useful in the invention include dye-based detection systems, affinity-based detection systems, microfabricated gravimetric analyzers, CCD cameras, optical detectors, optical microscopy systems, electrical systems, thermocouples and thermistors, pressure sensors, ion-sensitive field-effect transistors and arrays of them, etc. Those of ordinary skill in the art will be able to identify other suitable sensors for use in the invention. The sensor can include a colorimetric detection system in some cases, which may be external to the device, or microfabricated into the device in certain cases. As an example of a colorimetric detection system, if a dye or a fluorescent entity is used (e.g. in a particle), the colorimetric detection system may be able to detect a change or shift in the frequency and/or intensity of the dye or fluorescent entity.

Examples of sensors include, but are not limited to, pH sensors, optical sensors, ion sensors, colorimetric sensors, a sensor able to detect the concentration of a substance, or the like, e.g., as discussed herein. For instance, in one set of embodiments, the device may include an ion-selective electrode. The ion selective electrode may be able to determine a specific ion and/or ions such as $K^+$, $H^+$, $Na^+$, $Ag^+$, $Pb^{2+}$, $Cd^{2+}$, or the like. Various ion selective electrodes can be obtained commercially. As a non-limiting example, a potassium-selective electrode may include an ion exchange resin membrane, using valinomycin, a potassium channel, as the ion carrier in the membrane to provide potassium specificity.

Examples of analytes that the sensor may be used to determine include, but are not limited to, pH or metal ions, proteins, nucleic acids (e.g. DNA, RNA, etc.), drugs, sugars (e.g., glucose), hormones (e.g., estradiol, estrone, progesterone, progestin, testosterone, androstenedione, etc.), carbohydrates, or other analytes of interest. Other conditions that can be determined can include pH changes, which may indicate disease, yeast infection, periodontal disease at a mucosal surface, oxygen or carbon monoxide levels which indicate lung dysfunction, and drug levels, both legal prescription levels of drugs such as coumadin, other drugs such as nicotine, or illegal drugs such as cocaine. For example, an external reward may be offered if no (or reduced levels of) illegal drugs are determined in the subject. As another example, the substance may be a banned performance-enhancing drug, and an external reward may be offered if the drug is not determined within the subject (e.g., an athlete). Further examples of analytes include those indicative of disease, such as cancer specific markers such as CEA and PSA, viral and bacterial antigens, and autoimmune indicators such as antibodies to double stranded DNA, indicative of Lupus. Still other conditions include exposure to elevated carbon monoxide, which could be from an external source or due to sleep apnea, too much heat (important in the case of babies whose internal temperature controls are not fully self-regulating) or from fever. Still other potentially suitable analytes include various pathogens such as bacteria or viruses, and/or markers produced by such pathogens.

As additional non-limiting examples, the sensor may contain an antibody able to interact with a marker for a disease state, an enzyme such as glucose oxidase or glucose 1-dehydrogenase able to detect glucose, or the like. The analyte may be determined quantitatively or qualitatively, and/or the presence or absence of the analyte within the withdrawn fluid may be determined in some cases. Those of ordinary skill in the art will be aware of many suitable commercially-available sensors, and the specific sensor used may depend on the particular analyte being sensed. For instance, various non-limiting examples of sensor techniques include pressure or temperature measurements, spectroscopy such as infrared, absorption, fluorescence, UV/visible, FTIR ("Fourier Transform Infrared Spectroscopy"), or Raman; piezoelectric measurements; immunoassays; electrical measurements, electrochemical measurements (e.g., ion-specific electrodes); magnetic measurements, optical measurements such as optical density measurements; circular dichroism; light scattering measurements such as quasielectric light scattering; polarimetry; refractometry; chemical indicators such as dyes; or turbidity measurements, including nephelometry.

Still other potentially suitable analytes include various pathogens such as bacteria or viruses, and/or markers produced by such pathogens. Thus, in certain embodiments of the invention, as discussed below, one or more analytes may be determined in some fashion, which may be useful in determining a past, present and/or future condition of the subject.

In one set of embodiments, the sensor may be a test strip, for example, test strips that can be obtained commercially. Examples of test strips include, but are not limited to, glucose test strips, urine test strips, pregnancy test strips, or the like. A test strip will typically include a band, piece, or strip of paper or other material and contain one or more regions able to determine an analyte, e.g., via binding of the analyte to a diagnostic agent or a reaction entity able to interact with and/or associate with the analyte. For example, the test strip may include various enzymes or antibodies, glucose oxidase and/or ferricyanide, or the like. The test strip may be able to determine, for example, glucose, cholesterol, creatinine, ketones, blood, protein, nitrite, pH, urobilinogen, bilirubin, leucocytes, luteinizing hormone, etc., depending on the type of test strip. The test strip may be used in any number of different ways. In some cases, a test strip may be obtained commercially and inserted into the device, e.g., before or after withdrawing blood, interstitial fluid, or other fluids from a subject. At least a portion of the blood or other fluid may be exposed to the test strip to determine an analyte, e.g., in embodiments where the device uses the test strip as a sensor so that the device itself determines the analyte. In some cases, the device may be sold with a test strip pre-loaded, or a user may need to insert a test strip in a device (and optionally, withdraw and replace the test strip between uses). In certain cases, the test strip may form an integral part of the device that is not removable by a user. In some embodiments, after exposure to the blood or other fluid withdrawn from the subject, the test strip may be removed from the device and determined externally, e.g., using other apparatuses able to determine the test strip, for example, commercially-available test strip readers.

In one embodiment, an analyte may be determined as an "on/off" or "normal/abnormal" situation. Detection of the analyte, for example, may be indicative that insulin is needed; a trip to the doctor to check cholesterol; ovulation is occurring; kidney dialysis is needed; drug levels are present (e.g., especially in the case of illegal drugs) or too high/too low (e.g., important in care of geriatrics in particular in nursing homes). As another embodiment, however, an analyte may be determined quantitatively.

As described herein, any of a variety of signaling or display methods, associated with analyses, can be provided including signaling visually, by smell, sound, feel, taste, or the like, in one set of embodiments. Signal structures or generators include, but are not limited to, displays (visual, LED, light, etc.), speakers, chemical-releasing chambers (e.g., containing a volatile chemical), mechanical devices, heaters, coolers, or the like. In some cases, the signal structure or generator may be integral with the device (e.g., integrally connected with a support structure for application to the skin of the subject, e.g., containing a fluid transporter such as one or more needles or microneedles), or the signal structure may not be integrally connected with the support structure. As used herein, a "signal structure" or a "signal generator" is any apparatus able to generate a signal that is related to a condition of a medium. For example, the medium may be a bodily fluid, such as blood or interstitial fluid.

In some embodiments, signaling methods such as these may be used to indicate the presence and/or concentration of an analyte determined by the sensor, e.g., to the subject, and/or to another entity, such as those described below. Where a visual signal is provided, it can be provided in the form of change in opaqueness, a change in intensity of color and/or opaqueness, or can be in the form of a message (e.g., numerical signal, or the like), an icon (e.g., signaling by shape or otherwise a particular medical condition), a brand, logo, or the like. For instance, in one embodiment, the device may include a display. A written message such as "take next dose," or "glucose level is high" or a numerical value might be provided, or a message such as "toxin is present." These messages, icons, logos, or the like can be provided as an electronic read-out by a component of a device and/or can be displayed as in inherent arrangement of one or more components of the device.

In some embodiments, a device is provided where the device determines a physical condition of a subject and produces a signal related to the condition that can be readily understood by the subject (e.g., by provision of a visual "OK" signal as described above) or can be designed so as not to be readily understandable by a subject. Where not readily understandable, the signal can take a variety of forms. In one form, the signal might be a series of letters or numbers that mean nothing to the subject (e.g., A1278CDQ) which would have meaning to a medical professional or the like (and/or be decodable by the same, e.g., with reference to a suitable decoder) and can be associated with a particular physiological condition. Alternatively, a signal in the form of bar code can be provided by a device such that, under a particular condition or set of conditions the bar code appears and/or disappears, or changes, and can be read by a bar code reader to communicate information about the subject or analyte. In another embodiment, the device can be designed such that an ultraviolet signal is produced, or a signal that can be read only under ultraviolet light (e.g., a simple spot or patch, or any other signal such as a series of number, letters, bar code, message, or the like that can be readily understandable or not readily understandable by a subject) can be provided. The signal may be invisible to the human eye but, upon application UV light or other excitation energy, may be readable. The signal can be easily readable or understandable by a user via visual observation, or with other sensory activity such smell, feel, etc. In another set of embodiments equipment as described above may be needed to determine a signal provided by the device, such as equipment in a clinical setting, etc. In some cases, the device is able to transmit a signal indicative of the analyte to a receiver, e.g., as a wireless signal, a radio signal, etc.

In some embodiments, quantitative and/or qualitative analyses can be provided by a device. That is, the device in some cases may provide analyses that allow "yes/no" tests or the like, or tests that provide information on the quantity, concentration, or level of a particular analyte or analytes. Display configurations can be provided by the invention that reflect the amount of a particular analyte present in a subject at a particular point in time, or any other variable (presence of analysis over time, type of analyte, etc.) display configurations can take a variety of forms. In one example, a dial can be provided, similar to that of a speedometer with a series of level indications (e.g., numbers around the dial) and a "needle" or other device that indicates a particular level. In other configurations, a particular area of the device (e.g., on a display) can exist that is filled in to a greater or lesser extent depending upon the presence and/or quantity of a particular analyte present, e.g., in the form of a bar graph. In another arrangement a "color wheel" can be provided where the amount of a particular analyte present can control which colors of the wheel are visible. Or, different analytes can cause different colors of a wheel or different bars of a graph to become visible or invisible in a multiple analyte analysis. Multiple-analyte quantitative analyses can be reflected in multiple color wheels, a single color wheel with different colors per analyte where the intensity of each color reflects the amount of the analyte, or, for example, a plurality of bar graphs where each bar graph is reflective of a particular analyte and the level of the bar (and/or degree to which an area is filled in with visible color or other visible feature) is reflective of the amount of the analyte. As with all embodiments here, whatever signal is displayed can be understandable or not understandable to any number of participants. For example, it can be understandable to a subject or not understandable to a subject. Where not understandable it might need to be decoded, read electronically, or the like. Where read electronically, for example, a device may provide a signal that is not understandable to a subject or not even visible or otherwise able to be sensed by a subject, and a reader can be provided adjacent or approximate the device that can provide a visible signal that is understandable or not understandable to the subject, or can transmit a signal to another entity for analysis.

The display may also be used to display other information, in addition or instead of the above. For example, the device may include one or more displays that indicate when the device has been used or has been expired, that indicate that sampling of fluid from a subject is ongoing and/or complete, or that a problem has occurred with sampling (e.g., clogging or insufficient fluid collected), that indicate that analysis of an analyte within the collected sample is ongoing and/or complete, that an adequate amount of a fluid has been delivered to the subject (or that an inadequate amount has been delivered, and/or that fluid delivery is ongoing), that the device can be removed from the skin of the subject (e.g., upon completion of delivery and/or withdrawal of a fluid, and/or upon suitable analysis, transmission, etc.), or the like.

In connection with any signals associated with any analyses described herein, another, potentially related signal or other display (or smell, taste, or the like) can be provided which can assist in interpreting and/or evaluating the signal. In one arrangement, a calibration or control is provided proximate (or otherwise easily comparable with) a signal, e.g., a visual calibration/control or comparator next to or close to a visual signal provided by a device and/or implanted agents, particles, or the like.

A visual control or reference can be used with another sensory signal, such as that of smell, taste, temperature, itch, etc. A reference/control and/or experimental confirmation component can be provided, to be used in connection with an in-skin test or vice versa. References/indicators can also be used to indicate the state of life of a device, changing color or intensity and/or changing in another signaling aspect as the device changes relative to its useful life, so that a user can determine when the device should no longer be relied upon and/or removed. For certain devices, an indicator or control can be affected by adding analyte to the control (e.g., from a source outside of the source to be determine) to confirm operability of the device and/or to provide a reference against which to measure a signal of the device. For example, a device can include a button to be tapped by a user which will allow an analyte from a reservoir to transfer to an indicator region to provide a signal, to demonstrate operability of the device and/or provide a comparator for analysis.

Many of the embodiments described herein involve a quantitative analysis and related signal, i.e., the ability to determine the relative amount or concentration of an analyte in a medium. This can be accomplished in a variety of ways. For example, where an agent (e.g. a binding partner attached to a nanoparticle) is used to capture and analyze an analyte, the agent can be provided in a gradient in concentration across a sensing region of the device. Or a sensing region can include a membrane or other apparatus through which analyte is required to flow or pass prior to capture and identification, and the pathway for analyte travel can vary as a function of position of display region. For example, a membrane can be provided across a sensing region, through which analyte must pass prior to interacting with a layer of binding and/or signaling agent, and the membrane may vary in thickness laterally in a direction related to "bar graph" readout. Where a small amount of analyte is present, it may pass through the thinner portion but not the thicker portion of the membrane, but where a larger amount is present, it may pass across a thicker portion. The boundary (where one exists) between a region through which analyte passes, and one through which it does not completely pass, can define the "line" of the bar graph. Other ways of achieving the same or a similar result can include varying the concentration of a scavenger or transporter of the analyte, or an intermediate reactive species (between analyte and signaling event), across a membrane or other article, gradient in porosity or selectivity of the membrane, ability to absorb or transport sample fluid, or the like. These principles, in combination with other disclosure herein, can be used to facilitate any or all of the quantitative analyses described herein.

In one aspect, a subject having a condition such as a physiological condition to be analyzed (or other user, such as medical personnel) reads and/or otherwise determines a signal from a device. For example, the device may transmit a signal indicative of a condition of the subject and/or the device. Alternatively, or in addition, a signal produced by a device can be acquired in the form of a representation (e.g. a digitized signal, or the like) and transmitted to another entity for analysis and/or action. For example, a signal can be produced by a device, e.g., based on a sensor reading of an analyte, based on fluid delivered and/or withdrawn from the skin and/or beneath the skin, based on a condition of the device, or the like. The signal may represent any suitable data or image. For example, the signal may represent the presence and/or concentration of an analyte in fluid withdrawn from a subject, the amount of fluid withdrawn from a subject and/or delivered to the subject, the number of times the device has been used, the battery life of the device, the amount of vacuum left in the device, the cleanliness or sterility of the device, the identity of the device (e.g., where multiple devices are given unique identification numbers, to prevent counterfeiting, accidental exchange of equipment to incorrect users, etc.), or the like. For instance, in one set of embodiments, an image of the signal (e.g., a visual image or photograph) can be obtained and transmitted to a different entity (for example, a user can take a cell phone picture of a signal generated by the device and send it, via cell phone, the other entity).

The other entity that the signal is transmitted to can be a human (e.g., a clinician) or a machine. In some cases, the other entity may be able to analyze the signal and take appropriate action. In one arrangement, the other entity is a machine or processor that analyzes the signal and optionally sends a signal back to the device to give direction as to activity (e.g., a cell phone can be used to transmit an image of a signal to a processor which, under one set of conditions, transmits a signal back to the same cell phone giving direction to the user, or takes other action). Other actions can include automatic stimulation of the device or a related device to dispense a medicament or pharmaceutical, or the like. The signal to direct dispensing of a pharmaceutical can take place via the same used to transmit the signal to the entity (e.g., cell phone) or a different vehicle or pathway. Telephone transmission lines, wireless networks, Internet communication, and the like can also facilitate communication of this type.

As one specific example, a device may be a glucose monitor. As signal may be generated by the device and an image of the signal captured by a cell phone camera and then transmitted via cell phone to a clinician. The clinician may then determine that the glucose (or e.g., insulin) level is appropriate or inappropriate and send a message indicating this back to the subject via cell phone.

Information regarding the analysis can also be transmitted to the same or a different entity, or a different location simply by removing the device or a portion of the device from the skin of the subject and transferring it to a different location. For example, a device can be used in connection with a subject to analyze presence and/or amount of a particular analyte. At some point after the onset of use, the device, or a portion of the device carrying a signal or signals indicative of the analysis or analyses, can be removed and, e.g., attached to a record associated with the subject. As a specific example, a patch or other device can be worn by a subject to determine presence and/or amount of one or more analytes qualitatively, quantitatively, and/or over time. The subject can visit a clinician who can remove the patch or a portion of the patch and attach it to a medical record associated with the subject.

According to various aspects, the device may be used one, or multiple times, depending on the application. For instance, obtaining samples for sensing, according to certain embodiments of the invention, can be done such that sensing can be carried out continuously, discretely, or a combination of these. For example, where a bodily fluid such as blood or interstitial fluid is accessed for determination of an analyte, fluid can be accessed discretely (i.e., as a single dose, once or multiple times), or continuously by creating a continuous flow of fluid which can be analyzed once or any number of times. Additionally, testing can be carried out once, at a single point in time, or at multiple points in time, and/or from multiple samples (e.g., at multiple locations relative to the subject).

Alternatively or in addition, testing can be carried out continuously over any number of points in time involving one or any number of locations relative to the subject or other multiple samples. As an example, one bolus or isolated sample, of fluid such as blood or interstitial fluid can be obtained. From that fluid a test can be carried out to determine whether a particular analyte or other agent exists in the fluid. Alternatively, two or more tests can be carried out involving that quantity of fluid to determine the presence and/or quantity of two or more analytes, and any number of such tests can be carried out. Tests involving that quantity of fluid can be carried out simultaneously or over a period of time. For example, a test for a particular analyte can be carried out at various points in time to determine whether the result changes over time, or different analytes can be determined at different points in time. As another example, a pool of fluid can be formed between layers of skin via, e.g., a suction blister, and either within the suction blister or from fluid drawn from the suction blister and placed elsewhere, any of the above and other analysis can be carried out at one or more points in time. In some cases, a suction blister is formed in such a way that the interstitial fluid within the blister changes over time (e.g., where an equilibrium exists between interstitial fluid within the subject and interstitial fluid in the suction blister itself, i.e., the fluid within the blister is ever changing to reflect the content of the interstitial fluid of the subject in the region of the blister over time). Testing of fluid within or from the suction blister at various points in time can provide useful information.

In another example, one or more needles or microneedles, or other device(s) can be used to access a fluid of a subject such as blood or interstitial fluid (with or without use of a suction blister). Fluid can be drawn to a point of analysis and analyzed in any manner described herein. For example, an analysis can be carried out once, to determine the presence and/or quantity of a single analyte, or a number of tests can be carried out. From a single sample of fluid, a particular test or number of tests can be carried out essentially simultaneously, or analyses can be carried out over time. Moreover, fluid can be drawn continuously from the skin and/or beneath the skin of the subject and one or more tests can be carried out of any number of points in time. A variety of reasons for carrying out one or more tests over the course of time exists, as would be understood by those of ordinary skill in the art. One such reason is to determine whether the quantity or another characteristic of an analyte is constant in a subject, or changes over time. A variety of specific techniques for continuous and/or discrete testing will be described herein.

In some aspects, one or materials, such as particles, are delivered to or through the skin. Examples of suitable materials include, but are not limited to, particles such as microparticles or nanoparticles, a chemical, a drug or a pharmaceutical substance, a diagnostic agent, a carrier, or the like. The particles may be, for example, nanoparticles or microparticles, and in some cases, the particles may be anisotropic particles. In some cases, a plurality of particles may be used, and in some cases, some, or substantially all, of the particles may be the same. For example, at least about 10%, at least about 30%, at least about 40%, at least about 50%, at least about 60%, at least about 70%, at least about 80%, at least about 90%, at least about 95%, or at least about 99% of the particles may have the same shape, and/or may have the same composition.

The particles may be used for a variety of purposes. For instance, the particles may contain a diagnostic agent or a reaction entity able to interact with and/or associate with an analyte, or another reaction entity, or other particles. Such particles may be useful, for example, to determine one or more analytes, such as a marker of a disease state, as discussed below. As another example, the particles may contain a drug or a pharmaceutical substance, positioned on the surface and/or internally of the particles, which may be released by the particles and delivered to the subject. Specific examples of these and other embodiments are discussed in detail below.

In some cases, materials such as particles may become embedded within the skin, for example, due to physical properties of the materials (e.g., size, hydrophobicity, etc.). Thus, in some cases, a depot of material may be formed within the skin, and the depot may be temporary or permanent. For instance, materials within the depot may eventually degrade (e.g., if the material biodegradable), enter the bloodstream, or be sloughed off to the environment, e.g., as the cells of the dermis differentiate to form new epidermis and accordingly push the material towards the surface of the skin. Thus, the depot of material may be present within the subject on a temporary basis (e.g., on a time scale of days or weeks), in certain instances.

As mentioned, certain aspects of the present invention are generally directed to particles such as anisotropic particles or colloids, which can be used in a wide variety of applications. For instance, the particles may be present within the skin, or externally of the skin, e.g., in a device on the surface of the skin. The particles may include microparticles and/or nanoparticles. As discussed above, a "microparticle" is a particle having an average diameter on the order of micrometers (i.e., between about 1 micrometer and about 1 mm), while a "nanoparticle" is a particle having an average diameter on the order of nanometers (i.e., between about 1 nm and about 1 micrometer. The particles may be spherical or non-spherical, in some cases. For example, the particles may be oblong or elongated, or have other shapes such as those disclosed in U.S. patent application Ser. No. 11/851,974, filed Sep. 7, 2007, titled "Engineering Shape of Polymeric Micro- and Nanoparticles," by S. Mitragotri, et al.; International Patent Application No. PCT/US2007/077889, filed Sep. 7, 2007, titled "Engineering Shape of Polymeric Micro- and Nanoparticles," by S. Mitragotri, et al., published as WO 2008/031035 on Mar. 13, 2008; U.S. patent application Ser. No. 11/272,194, filed Nov. 10, 2005, titled "Multi-phasic Nanoparticles," by J. Lahann, et al., published as U.S. Patent Application Publication No. 2006/0201390 on Sep. 14, 2006; or U.S. patent application Ser. No. 11/763,842, filed Jun. 15, 2007, titled "Multi-Phasic Bioadhesive Nano-Objects as Biofunctional Elements in Drug Delivery Systems," by J. Lahann, published as U.S. Patent Application Publication No. 2007/0237800 on Oct. 11, 2007, each of which is incorporated herein by reference. Other examples of particles can be seen in U.S. patent application Ser. No. 11/272,194, filed Nov. 10, 2005, titled "Multi-phasic Nanoparticles," by J. Lahann, et al., published as U.S. Patent Application Publication No. 2006/0201390 on Sep. 14, 2006; U.S. patent application Ser. No. 11/763,842, filed Jun. 15, 2007, titled "Multi-Phasic Bioadhesive Nan-Objects as Biofunctional Elements in Drug Delivery Systems," by J. Lahann, published as U.S. Patent Application Publication No. 2007/0237800 on Oct. 11, 2007; or U.S. Provisional Patent Application Ser. No. 61/058,796, filed Jun. 4, 2008, titled "Compositions and Methods for Diagnostics, Therapies, and Other Applications," by D. Levinson, each of which is incorporated herein by reference.

The particles may be formed of any suitable material, depending on the application. For example, the particles may comprise a glass, and/or a polymer such as polyethylene, polystyrene, silicone, polyfluoroethylene, polyacrylic acid, a polyamide (e.g., nylon), polycarbonate, polysulfone, polyurethane, polybutadiene, polybutylene, polyethersulfone, polyetherimide, polyphenylene oxide, polymethylpentene, polyvinylchloride, polyvinylidene chloride, polyphthalamide, polyphenylene sulfide, polyester, polyetheretherketone, polyimide, polymethylmethacylate and/or polypropylene. In some cases, the particles may comprise a ceramic such as tricalcium phosphate, hydroxyapatite, fluorapatite, aluminum oxide, or zirconium oxide. In some cases (for example, in certain biological applications), the particles may be formed from biocompatible and/or biodegradable polymers such as polylactic and/or polyglycolic acids, polyanhydride, polycaprolactone, polyethylene oxide, polyacrylamide, polyacrylic acid, polybutylene terephthalate, starch, cellulose, chitosan, and/or combinations of these. In one set of embodiments, the particles may comprise a hydrogel, such as agarose, collagen, or fibrin. The particles may include a magnetically susceptible material in some cases, e.g., a material displaying paramagnetism or ferromagnetism. For instance, the particles may include iron, iron oxide, magnetite, hematite, or some other compound containing iron, or the like. In another embodiment, the particles can include a conductive material (e.g., a metal such as titanium, copper, platinum, silver, gold, tantalum, palladium, rhodium, etc.), or a semiconductive material (e.g., silicon, germanium, CdSe, CdS, etc.). Other particles potentially useful in the practice of the invention include ZnS, ZnO, $TiO_2$, AgI, AgBr, $HgI_2$, PbS, PbSe, ZnTe, CdTe, $In_2S_3$, $In_2Se_3$, $Cd_3P_2$, $Cd_3As_2$, InAs, or GaAs. The particles may include other species as well, such as cells, biochemical species such as nucleic acids (e.g., RNA, DNA, PNA, etc.), proteins, peptides, enzymes, nanoparticles, quantum dots, fragrances, indicators, dyes, fluorescent species, chemicals, small molecules (e.g., having a molecular weight of less than about 1 kDa), or the like.

The particles may also have any shape or size. For instance, the particles may have an average diameter of less than about 5 mm or 2 mm, or less than about 1 mm, or less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 nm, or less than about 10 nm. As discussed, the particles may be spherical or non-spherical. The average diameter of a non-spherical particle is the diameter of a perfect sphere having the same volume as the non-spherical particle. If the particle is non-spherical, the particle may have a shape of, for instance, an ellipsoid, a cube, a fiber, a tube, a rod, or an irregular shape. In some cases, the particles may be hollow or porous. Other shapes are also possible, for instance, core/shell structures (e.g., having different compositions), rectangular disks, high aspect ratio rectangular disks, high aspect ratio rods, worms, oblate ellipses, prolate ellipses, elliptical disks, UFOs, circular disks, barrels, bullets, pills, pulleys, biconvex lenses, ribbons, ravioli, flat pills, bicones, diamond disks, emarginate disks, elongated hexagonal disks, tacos, wrinkled prolate ellipsoids, wrinkled oblate ellipsoids, porous ellipsoid disks, and the like. See, e.g., International Patent Application No. PCT/US2007/077889, filed Sep. 7, 2007, titled "Engineering Shape of Polymeric Micro- and Nanoparticles," by S. Mitragotri, et al., published as WO 2008/031035 on Mar. 13, 2008, incorporated herein by reference.

In one aspect of the invention, a particle may include one or more reaction entities present on the surface (or at least a portion of the surface) of the particle. The reaction entity may be any entity able to interact with and/or associate with an analyte, or another reaction entity. For instance, the reaction entity may be a binding partner able to bind an analyte. For example, the reaction entity may be a molecule that can undergo binding with a particular analyte. The reaction entities may be used, for example, to determine pH or metal ions, proteins, nucleic acids (e.g. DNA, RNA, etc.), drugs, sugars (e.g., glucose), hormones (e.g., estradiol, estrone, progesterone, progestin, testosterone, androstenedione, etc.), carbohydrates, or other analytes of interest.

The term "binding partner" refers to a molecule that can undergo binding with a particular molecule, e.g., an analyte. For example, the binding may be highly specific and/or non-covalent. Binding partners which form highly specific, non-covalent, physiochemical interactions with one another are defined herein as "complementary." Biological binding partners are examples. For example, Protein A is a binding partner of the biological molecule IgG, and vice versa. Other non-limiting examples include nucleic acid-nucleic acid binding, nucleic acid-protein binding, protein-protein binding, enzyme-substrate binding, receptor-ligand binding, receptor-hormone binding, antibody-antigen binding, etc. Binding partners include specific, semi-specific, and non-specific binding partners as known to those of ordinary skill in the art. For example, Protein A is usually regarded as a "non-specific" or semi-specific binder. As another example, the particles may contain an enzyme such as glucose oxidase or glucose 1-dehydrogenase, or a lectin such as concanavalin A that is able to bind to glucose.

As additional examples, binding partners may include antibody/antigen pairs, ligand/receptor pairs, enzyme/substrate pairs and complementary nucleic acids or aptamers. Examples of suitable epitopes which may be used for antibody/antigen binding pairs include, but are not limited to, HA, FLAG, c-Myc, glutathione-S-transferase, $His_6$, GFP, DIG, biotin and avidin. Antibodies may be monoclonal or polyclonal. Suitable antibodies for use as binding partners include antigen-binding fragments, including separate heavy chains, light chains Fab, Fab', $F(ab')_2$, Fabc, and Fv. Antibodies also include bispecific or bifunctional antibodies. Exemplary binding partners include biotin/avidin, biotin/streptavidin, biotin/neutravidin and glutathione-S-transferase/glutathione.

The term "binding" generally refers to the interaction between a corresponding pair of molecules or surfaces that exhibit mutual affinity or binding capacity, typically due to specific or non-specific binding or interaction, including, but not limited to, biochemical, physiological, and/or chemical interactions. The binding may be between biological molecules, including proteins, nucleic acids, glycoproteins, carbohydrates, hormones, or the like. Specific non-limiting examples include antibody/antigen, antibody/hapten, enzyme/substrate, enzyme/inhibitor, enzyme/cofactor, binding protein/substrate, carrier protein/substrate, lectin/carbohydrate, receptor/hormone, receptor/effector, complementary strands of nucleic acid, protein/nucleic acid repressor/inducer, ligand/cell surface receptor, virus/ligand, virus/cell surface receptor, etc. As another example, the binding agent may be a chelating agent (e.g., ethylenediaminetetraacetic acid) or an ion selective polymer (e.g., a block copolymer such as poly(carbonate-b-dimethylsiloxane), a crown ether, or the like). As another example, the binding partners may be biotin and streptavidin, or the binding partners may be various antibodies raised against a protein.

The term "specifically binds," when referring to a binding partner (e.g., protein, nucleic acid, antibody, etc.), refers to a reaction that is determinative of the presence and/or identity of one or other member of the binding pair in a mixture of heterogeneous molecules (e.g., proteins and other biologics). Thus, for example, in the case of a receptor/ligand binding pair, the ligand would specifically and/or preferentially select its receptor from a complex mixture of molecules, or vice versa. An enzyme would specifically bind to its substrate, a nucleic acid would specifically bind to its complement, an antibody would specifically bind to its antigen, etc. The binding may be by one or more of a variety of mechanisms including, but not limited to ionic interactions or electrostatic interactions, covalent interactions, hydrophobic interactions, van der Waals interactions, etc.

Thus, the invention provides, in certain embodiments, particles that are able to bind to an analyte, e.g., via a binding partner to the analyte, and such particles can be used to determine the analyte. Such determination may occur within the skin, and/or externally of the subject, e.g., within a device on the surface of the skin, depending on the embodiment. "Determine," in this context, generally refers to the analysis of a species, for example, quantitatively or qualitatively, and/or the detection of the presence or absence of the species. "Determining" may also refer to the analysis of an interaction between two or more species, for example, quantitatively or qualitatively, and/or by detecting the presence or absence of the interaction, e.g. determination of the binding between two species. "Determining" also means detecting or quantifying interaction between species. As an example, an analyte may cause a determinable change in a property of the particles, e.g., a change in a chemical property of the particles, a change in the appearance and/or optical properties of the particles, a change in the temperature of the particles, a change in an electrical property of the particles, etc. In some cases, the change may be one that is determinable by a human, unaided by any equipment that may be directly applied to the human. For instance, the determinable change may be a change in appearance (e.g., color), a change in temperature, the production of an odor, etc., which can be determined by a human without the use of any equipment (e.g., using the eyes). Non-limiting examples include temperature changes, chemical reactions or other interactions (e.g., with capsaicin) that can be sensed, or the like. Examples of capsaicin and capsaicin-like molecules include, but are not limited to, dihydrocapsaicin, nordihydrocapsaicin, homodihydrocapsaicin, homocapsaicin, or nonivamide. Without wishing to be bound by any theory, it is believed that interactions with capsaicin and capsaicin-like molecules can be sensed by a subject, since such molecules may interact with certain nerve endings, which produces a sensation of burning.

In some cases, the particles may contain a diagnostic agent able to determine an analyte. An example of an analyte within a subject is glucose (e.g., for diabetics); other potentially suitable analytes include ions such as sodium, potassium, chloride, calcium, magnesium, and/or bicarbonate (e.g., to determine dehydration); gases such as carbon dioxide or oxygen; pH; metabolites such as urea, blood urea nitrogen or creatinine; hormones such as estradiol, estrone, progesterone, progestin, testosterone, androstenedione, etc. (e.g., to determine pregnancy, illicit drug use, or the like); or cholesterol. Still other potentially suitable analytes include various pathogens such as bacteria or viruses, and/or markers produced by such pathogens. For example, a particle may include an antibody directed at a marker produced by a bacteria. In addition, more than one analyte may be determined in a subject, e.g., through the use of different particle types and/or through the use of particles able to determine more than one analyte, such as those discussed above. For instance, a first set of particles may determine a first analyte and a second set of particles may determine a second analyte. In some cases, such particles may be used to determine a physical condition of a subject. For instance, the particles may exhibit a first color indicating a healthy state and a second color indicating a disease state. In some cases, the appearance of the particles may be used to determine a degree of health. For instance, the particles may exhibit a first color indicating a healthy state, a second color indicating a warning state, and a third color indicating a dangerous state, or the particles may exhibit a range of colors indicating a degree of health of the subject.

Binding partners to these and/or other species are well-known in the art. Non-limiting examples include pH-sensitive entities such as phenol red, bromothymol blue, chlorophenol red, fluorescein, HPTS, 5(6)-carboxy-2',7'-dimethoxyfluorescein SNARF, and phenothalein; entities sensitive to calcium such as Fura-2 and Indo-1; entities sensitive to chloride such as 6-methoxy-N-(3-sulfopropyl)-quinolinim and lucigenin; entities sensitive to nitric oxide such as 4-amino-5-methylamino-2',7'-difluorofluorescein; entities sensitive to dissolved oxygen such as tris(4,4'-diphenyl-2,2'-bipyridine) ruthenium (II) chloride pentahydrate; entities sensitive to dissolved $CO_2$; entities sensitive to fatty acids, such as BODIPY 530-labeled glycerophosphoethanolamine; entities sensitive to proteins such as 4-amino-4'-benzamidostilbene-2-2'-disulfonic acid (sensitive to serum albumin), X-Gal or NBT/BCIP (sensitive to certain enzymes), $Tb^{3+}$ from $TbCl_3$ (sensitive to certain calcium-binding proteins), BODIPY FL phallacidin (sensitive to actin), or BOCILLIN FL (sensitive to certain penicillin-binding proteins); entities sensitive to concentration of glucose, lactose or other components, or entities sensitive to proteases, lactates or other metabolic byproducts, entities sensitive to proteins, antibodies, or other cellular products.

In some cases, a pooled region of fluid, such as a suction blister, may be formed in the skin to facilitate delivery and/or withdrawal of fluid from the skin. Thus, certain aspects of the present invention are generally directed to the creation of suction blisters or other pooled regions of fluid within the skin. In one set of embodiments, a pooled region of fluid can be created between the dermis and epidermis of the skin. Suction blisters or other pooled regions may form in a manner such that the suction blister or other pooled region is not significantly pigmented in some cases, since the basal layer of the epidermis contains melanocytes, which are responsible for producing pigments. Such regions can be created by causing the dermis and the epidermis to at least partially separate, and as will be discussed below, a number of techniques can be used to at least partially separate the dermis from the epidermis.

In one technique, a pool of interstitial fluid is formed between layers of skin of a subject and, after forming the pool, fluid is drawn from the pool by accessing the fluid through a layer of skin, for example, puncturing the outer layer of skin with one or more microneedles. Specifically, for example, a suction blister can be formed and then the suction blister can be punctured and fluid can be drawn from the blister. In another technique, an interstitial region can be accessed and fluid drawn from that region without first forming a pool of fluid via a suction blister or the like. For example, a microneedle or microneedles can be applied to the interstitial region and fluid can be drawn therefrom. Where microneedles are used, it can be advantageous to select needles of length such that interstitial fluid is preferentially obtained and, where not desirable, blood is not accessed.

Pooled regions of fluids may be formed on any suitable location within the skin of a subject. Factors such as safety or convenience may be used to select a suitable location, as (in humans) the skin is relatively uniform through the body, with the exception of the hands and feet. As non-limiting examples, the pooled region may be formed on an arm or a leg, on the chest, abdomen, or the back of the subject, or the like. The size of the pooled region of fluid that is formed in the skin and/or the duration that the pooled region lasts within the skin depends on a variety of factors, such as the technique of creating the pooled region, the size of the pooled region, the size of the region of skin to which the technique is applied, the amount of fluid withdrawn from the pooled region (if any), any materials that are delivered into the pooled region, or the like. For example, if vacuum is applied to the skin to create a suction blister, the vacuum applied to the skin, the duration of the vacuum, and/or the area of the skin affected may be controlled to control the size and/or duration of the suction blister. In some embodiments, it may be desirable to keep the pooled regions relatively small, for instance, to prevent an unsightly visual appearance, to allow for greater sampling accuracy (due to a smaller volume of material), or to allow for more controlled placement of particles within the skin. For example, the volume of the pooled region may be kept to less than about 2 ml or less than about 1 ml in certain cases, or the average diameter of the pooled region (i.e., the diameter of a circle having the same area as the pooled region) may be kept to less than about 5 cm, less than about 4 cm, less than about 3 cm, less than about 2 cm, less than about 1 cm, less than about 5 mm, less than about 4 mm, less than about 3 mm, less than about 2 mm, or less than about 1 mm.

A variety of techniques may be used to cause pooled regions of fluid to form within the skin. In one set of embodiments, vacuum is applied to create a suction blister, or otherwise used to collect blood or interstitial fluid from a subject. In other embodiments, however, other methods may be used to create as a pooled region of fluid within the skin besides, or in addition to, the use of vacuum. When vacuum (i.e., the amount of pressure below atmospheric pressure, such that atmospheric pressure has a vacuum of 0 mmHg, i.e., the pressure is gauge pressure rather than absolute pressure) is used to at least partially separate the dermis from the epidermis to cause the pooled region to form, the pooled region of fluid thus formed can be referred to as a suction blister. For example, vacuums of at least about 50 mmHg, at least about 100 mmHg, at least about 150 mmHg, at least about 200 mmHg, at least about 250 mmHg, at least about 300 mmHg, at least about 350 mmHg, at least about 400 mmHg, at least about 450 mmHg, at least about 500 mmHg, at least about 550 mmHg, at least about 600 mmHg, at least about 650 mmHg, at least about 700 mmHg, or at least about 750 mmHg may be applied to the skin, e.g., to cause a suction blister and/or to collect blood or interstitial fluid from a subject (as discussed, these measurements are negative relative to atmospheric pressure. Different amounts of vacuum may be applied to different subjects in some cases, for example, due to differences in the physical characteristics of the skin of the subjects.

The vacuum may be applied to any suitable region of the skin, and the area of the skin to which the vacuum may be controlled in some cases. For instance, the average diameter of the region to which vacuum is applied may be kept to less than about 5 cm, less than about 4 cm, less than about 3 cm, less than about 2 cm, less than about 1 cm, less than about 5 mm, less than about 4 mm, less than about 3 mm, less than about 2 mm, or less than about 1 mm. In addition, such vacuums may be applied for any suitable length of time at least sufficient to cause at least some separation of the dermis from the epidermis to occur. For instance, vacuum may be applied to the skin for at least about 1 min, at least about 3 min, at least about 5 min, at least about 10 min, at least about 15 min, at least about 30 min, at least about 1 hour, at least about 2 hours, at least about 3 hours, at least about 4 hours, etc. Examples of devices suitable for creating such suction blisters are discussed in more detail below. In other cases, however, bodily fluids such as blood or interstitial fluid may be withdrawn from the skin and/or beneath the skin using vacuum without the creation of a suction blister. Other non-limiting examples of fluids include saliva, sweat, tears, mucus, plasma, lymph, or the like.

Other methods besides vacuum may be used to cause such separation to occur. For example, in another set of embodiments, heat may be used. For instance, a portion of the skin may be heated to at least about 40° C., at least about 50° C., at least about 55° C., or at least about 60° C., using any suitable technique, to cause such separation to occur. The skin may be heated, for instance, using an external heat source (e.g., radiant heat or a heated water bath), a chemical reaction, electromagnetic radiation (e.g., microwave radiation, infrared radiation, etc.), or the like. In some cases, the radiation may be focused on a relatively small region of the skin, e.g., to at least partially spatially contain the amount of heating within the skin that occurs.

In yet another set of embodiments, a separation chemical may be applied to the skin to at least partially cause separation of the dermis and the epidermis to occur. Non-limiting examples of such separation chemicals include proteases such as trypsin, purified human skin tryptase, or compound 48/80. Separation compounds such as these are commercially available from various sources. The separation chemical may be applied directly to the skin, e.g., rubbed into the surface of the skin, or in some cases, the separation chemical can be delivered into the subject, for example, between the epidermis and dermis of the skin. The separation chemical can, for example, be injected in between the dermis and the epidermis.

Another example of a separation chemical is a blistering agent, such as pit viper venom or blister beetle venom. Non-limiting examples of blistering agents include phosgene oxime, Lewisite, sulfur mustards (e.g., mustard gas or 1,5-dichloro-3-thiapentane, 1,2-bis(2-chloroethylthio)ethane, 1,3-bis(2-chloroethylthio)-n-propane, 1,4-bis(2-chloroethylthio)-n-butane, 1,5-bis(2-chloroethylthio)-n-pentane, 2-chloroethylchloromethylsulfide, bis(2-chloroethyl)sulfide, bis(2-chloroethylthio)methane, bis(2-chloroethylthiomethyl)ether, or bis(2-chloroethylthioethyl)ether), or nitrogen mustards (e.g., bis(2-chloroethyl)ethylamine, bis(2-chloroethyl)methylamine, or tris(2-chloroethyl)amine).

In still another set of embodiments, a device may be inserted into the skin and used to mechanically separate the epidermis and the dermis, for example, a wedge or a spike. Fluids may also be used to separate the epidermis and the dermis, in yet another set of embodiments. For example, saline or another relatively inert fluid may be injected into the skin between the epidermis and the dermis to cause them to at least partially separate.

These and/or other techniques may also be combined, in still other embodiments. For example, in one embodiment, vacuum and heat may be applied to the skin of a subject, sequentially and/or simultaneously, to cause such separation to occur. As a specific example, in one embodiment, vacuum is applied while the skin is heated to a temperature of between about 40° C. and about 50° C.

Figure 2D:
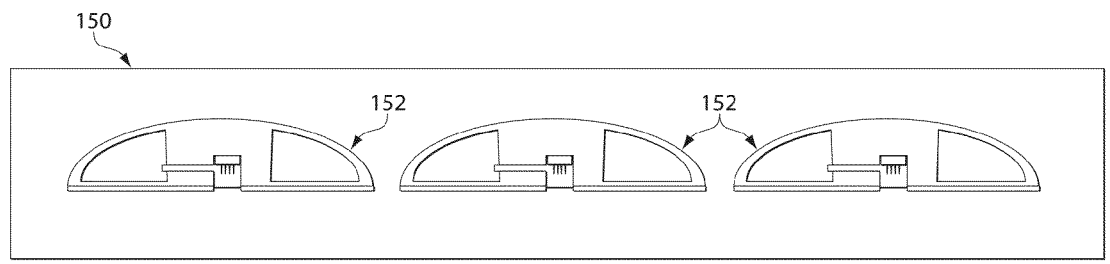
FIG. 2D illustrates a kit containing more than one device, in yet another embodiment of the invention.
Figure 2E:
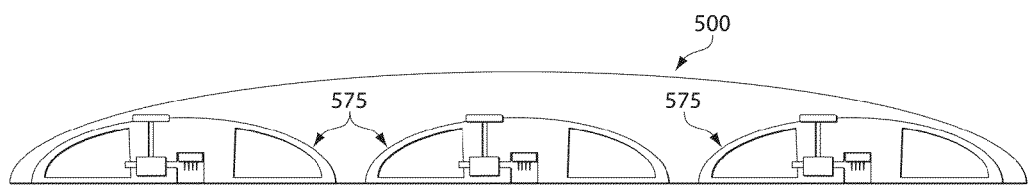
FIG. 2E illustrates a device according to still another embodiment of the invention.

In another aspect, the present invention is directed to a kit including one or more of the compositions previously discussed, e.g., a kit including a device for the delivery and/or withdrawal of fluid from the skin and/or beneath the skin, a kit including a device able to create a pooled region of fluid within the skin of a subject, a kit including a device able to determine a fluid, a kit including a drug (or other substance) and a device able to determine the drug (or other substance) within the skin, or the like. An example of a kit containing more than one device of the invention is illustrated in FIG. 2D, with kit 150 containing devices 152. A "kit," as used herein, typically defines a package or an assembly including one or more of the compositions or devices of the invention, and/or other compositions or devices associated with the invention, for example, as previously described. For example, in one set of embodiments, the kit may include a device and one or more compositions for use with the device. Each of the compositions of the kit, if present, may be provided in liquid form (e.g., in solution), or in solid form (e.g., a dried powder). In certain cases, some of the compositions may be constitutable or otherwise processable (e.g., to an active form), for example, by the addition of a suitable solvent or other species, which may or may not be provided with the kit. Examples of other compositions or components associated with the invention include, but are not limited to, solvents, surfactants, diluents, salts, buffers, emulsifiers, chelating agents, fillers, antioxidants, binding agents, bulking agents, preservatives, drying agents, antimicrobials, needles, syringes, packaging materials, tubes, bottles, flasks, beakers, dishes, frits, filters, rings, clamps, wraps, patches, containers, tapes, adhesives, and the like, for example, for using, administering, modifying, assembling, storing, packaging, preparing, mixing, diluting, and/or preserving the compositions components for a particular use, for example, to a sample and/or a subject.

A kit of the invention may, in some cases, include instructions in any form that are provided in connection with the compositions of the invention in such a manner that one of ordinary skill in the art would recognize that the instructions are to be associated with the compositions of the invention. For instance, the instructions may include instructions for the use, modification, mixing, diluting, preserving, administering, assembly, storage, packaging, and/or preparation of the compositions and/or other compositions associated with the kit. In some cases, the instructions may also include instructions for the delivery and/or administration of the compositions, for example, for a particular use, e.g., to a sample and/or a subject. The instructions may be provided in any form recognizable by one of ordinary skill in the art as a suitable vehicle for containing such instructions, for example, written or published, verbal, audible (e.g., telephonic), digital, optical, visual (e.g., videotape, DVD, etc.) or electronic communications (including Internet or web-based communications), provided in any manner.

In some embodiments, the present invention is directed to methods of promoting one or more embodiments of the invention as discussed herein. As used herein, "promoted" includes all methods of doing business including, but not limited to, methods of selling, advertising, assigning, licensing, contracting, instructing, educating, researching, importing, exporting, negotiating, financing, loaning, trading, vending, reselling, distributing, repairing, replacing, insuring, suing, patenting, or the like that are associated with the systems, devices, apparatuses, articles, methods, compositions, kits, etc. of the invention as discussed herein. Methods of promotion can be performed by any party including, but not limited to, personal parties, businesses (public or private), partnerships, corporations, trusts, contractual or sub-contractual agencies, educational institutions such as colleges and universities, research institutions, hospitals or other clinical institutions, governmental agencies, etc. Promotional activities may include communications of any form (e.g., written, oral, and/or electronic communications, such as, but not limited to, e-mail, telephonic, Internet, Web-based, etc.) that are clearly associated with the invention.

In one set of embodiments, the method of promotion may involve one or more instructions. As used herein, "instructions" can define a component of instructional utility (e.g., directions, guides, warnings, labels, notes, FAQs or "frequently asked questions," etc.), and typically involve written instructions on or associated with the invention and/or with the packaging of the invention. Instructions can also include instructional communications in any form (e.g., oral, electronic, audible, digital, optical, visual, etc.), provided in any manner such that a user will clearly recognize that the instructions are to be associated with the invention, e.g., as discussed herein.

The following documents are incorporated herein by reference: U.S. Provisional Patent Application Ser. No. 61/058,796, filed Jun. 4, 2008, titled "Compositions and Methods for Diagnostics, Therapies, and Other Applications"; U.S. Provisional Patent Application Ser. No. 61/163,791, filed Mar. 26, 2009, titled "Composition and Methods for Rapid One-Step Diagnosis"; U.S. Provisional Patent Application Ser. No. 61/163,793, filed Mar. 26, 2009, titled "Compositions and Methods for Diagnostics, Therapies, and Other Applications"; U.S. patent application Ser. No. 12/478,756, filed Jun. 4, 2009, titled "Compositions and Methods for Diagnostics, Therapies, and Other Applications"; International Patent Application No. PCT/US09/046,333, filed Jun. 4, 2009, titled "Compositions and Methods for Diagnostics, Therapies, and Other Applications"; U.S. Provisional Patent Application Ser. No. 61/163,710, filed Mar. 26, 2009, titled "Systems and Methods for Creating and Using Suction Blisters or Other Pooled Regions of Fluid within the Skin"; U.S. Provisional Patent Application Ser. No. 61/163,733, filed Mar. 26, 2009, titled "Determination of Tracers within Subjects"; U.S. Provisional Patent Application Ser. No. 61/163,750, filed Mar. 26, 2009, titled "Monitoring of Implants and Other Devices"; U.S. Provisional Patent Application Ser. No. 61/154,632, filed Mar. 2, 2009, titled "Oxygen Sensor"; and U.S. Provisional Patent Application Ser. No. 61/269,436, filed Jun. 24, 2009, titled "Devices and Techniques associated with Diagnostics, Therapies, and Other Applications, Including Skin-Associated Applications."

Also incorporated by reference herein are U.S. Provisional Patent Application Ser. No. 61/263,882, filed Nov. 24, 2009, titled "Patient-Enacted Sampling Technique"; U.S. Provisional Patent Application Ser. No. 61/294,543, filed Jan. 13, 2010, titled "Blood Sampling Device and Method"; U.S. patent application Ser. No. 12/716,222, filed Mar. 2, 2010, titled "Oxygen Sensor," by Levinson, et al.; U.S. patent application Ser. No. 12/716,233, filed Mar. 2, 2010, titled "Systems and Methods for Creating and Using Suction Blisters or Other Pooled Regions of Fluid within the Skin," by Levinson, et al.; U.S. patent application Ser. No. 12/716,226, filed Mar. 2, 2010, titled "Techniques and Devices Associated with Blood Sampling," by Levinson, et al.; and U.S. patent application Ser. No. 12/716,229, filed Mar. 2, 2010, titled "Devices and Techniques Associated with Diagnostics, Therapies, and Other Applications, Including Skin-Associated Applications," by Bernstein, et al.

Also incorporated herein by reference are the following applications: U.S. Provisional Patent Application Ser. No. 61/256,874, filed Oct. 30, 2009, titled "Systems and Methods for Application to Skin and Control of Use Thereof," by Bernstein, et al.; U.S. Provisional Patent Application Ser. No. 61/256,880, filed Oct. 30, 2009, titled "Systems and Methods for Altering or Masking Perception of Treatment of a Subject," by Chickering, et al. and U.S. Provisional Patent Application Ser. No. 61/256,871, filed Oct. 30, 2009, titled "Packaging Systems and Methods for Devices Applied to the Skin," By Bernstein, et al. In addition, the following are incorporated by reference herein: U.S. Provisional Patent Application Ser. No. 61/256,863, filed Oct. 30, 2009, titled "Systems and Methods for Treating or Shielding Blood on the Surface of the Skin," by Bernstein, et al.; U.S. Provisional Patent Application Ser. No. 61/256,910, filed Oct. 30, 2009, titled "Systems and Methods for Sanitizing or Treating the Skin or Devices Applied to the Skin," by Bernstein, et al.; U.S. Provisional Patent Application Ser. No. 61/256,931, filed Oct. 30, 2009, titled "Modular Systems for Application to the Skin," by Bernstein, et al.; U.S. Provisional Patent Application Ser. No. 61/256,933, filed Oct. 30, 2009, titled "Relatively Small Devices Applied to the Skin and Methods of Use Thereof," by Chickering, et al.; U.S. Provisional Patent Application Ser. No. 61/294,543, filed Jan. 13, 2010, titled "Blood Sampling Device and Method," by Chickering, et al.; U.S. Provisional Patent Application Ser. No. 61/334,533, filed May 13, 2010, titled "Rapid Delivery and/or Withdrawal of Fluids," by Chickering, et al.; U.S. Provisional Patent Application Ser. No. 61/334,529, filed May 13, 2010, titled "Sampling Device Interfaces," by Chickering, et al.; U.S. Provisional Patent Application Ser. No. 61/357,582, filed Jun. 23, 2010, titled "Sampling Devices and Methods Involving Relatively Little Pain," by Chickering, et al.; U.S. Provisional Patent Application Ser. No. 61/367,607, filed Jul. 26, 2010, titled "Rapid Delivery and/or Withdrawal of Fluids," by Davis, et al.; and U.S. Provisional Patent Application Ser. No. 61/373,764, filed Aug. 13, 2010, titled "Clinical and/or Consumer Techniques and Devices," by Chickering, et al.

It should be understood that as used herein, references to "another" embodiment or set of embodiments does not imply that any particular embodiments are incompatible or mutually exclusive with any other embodiment; instead, it is contemplated that one embodiment and "another" embodiment may be combined in any instance unless they are clearly physically incompatible with each other.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent and Trademark Office Manual of Patent Examining Procedures, Section 2111.03.

What is claimed is:

1. A device, comprising:
    a sensor configured, adapted or designed to determine a species withdrawn from a subject;
    a processor configured to determine compliance of the subject to a prescription based on the determination of the species; and
    a device indicator configured to indicate availability of an external reward based on the compliance of the subject to the prescription, wherein the external reward is available from a machine physically separate from the device.
2. The device of claim 1, wherein the device indicator comprises a display screen.
3. The device of claim 1, wherein the device indicator is configured to produce a coupon.
4. The device of claim 1, wherein the device indicator comprises a light.
5. The device of claim 1, wherein the external reward comprises a coupon.
6. The device of claim 1, wherein the external reward comprises a monetary reward.
7. The device of claim 1, wherein the external reward comprises a visual display.
8. The device of claim 1, wherein the external reward comprises music.
9. The device of claim 1, wherein the external reward comprises a movie.
10. The device of claim 1, wherein the external reward comprises an advertisement.
11. The device of claim 1, wherein the external reward comprises a link to a web page.
12. A method, comprising:
    withdrawing a species from a subject using a device fastened to the subject;
    determining information comprising an amount and/or a concentration of the species using at least the device;
    transmitting the information to a physically separate computing device;
    determining compliance of the subject to a prescription, using the physically separate computing device, based on the transmitted information; and
    using the computing device to provide, via an output device, non-number feedback to the subject based on the compliance of the subject to the prescription.
13. The method of claim 12, wherein the output device provides visual feedback.
14. The method of claim 12, wherein the output device provides auditory feedback.
15. The method of claim 14, wherein the output device provides music.
16. The method of claim 12, wherein the species is contained in blood withdrawn from the subject.
17. The method of claim 12, wherein the device is configured to withdraw the species from the subject using a microneedle.
18. The method of claim 12, wherein the device is configured to apply a vacuum to the skin.
19. The method of claim 12, further comprising an activator for activating the device to withdraw the species from the subject.
20. A method, comprising:
    determining information representing a property of a species withdrawn from the blood of a subject using a device immobilized to the skin of the subject;
    transmitting the information, using the device, to a machine physically separate from the device;

determining compliance of the subject, using the machine, to a prescription based on the transmitted information; and transmitting a signal from the machine to the device to cause the device to indicate availability of an external reward available from the machine, wherein the signal is based on compliance of the subject to the prescription.

21. The method of claim 20, wherein the device is adhered to the skin of the subject.

22. A method, comprising:

providing a subject to which a drug has been administered, wherein the subject has a condition suspected of being treatable by the drug, and wherein the drug administered to the subject can not be distinguished after administration, by the subject, from a placebo without any external equipment;

determining a species withdrawn from the blood of the subject that is indicative of the drug administered to the subject;

determining compliance of the subject to a prescription involving the drug, based on the withdrawn species; and providing feedback to the subject and/or another person based on the compliance of the subject to the prescription.

23. The method of claim 22, wherein the species is the drug.

24. The method of claim 22, wherein the species withdrawn from a subject is indicative of the effect of the drug administered to the subject.

25. The method of claim 22, wherein the species withdrawn from a subject is indicative of the amount of the drug administered to the subject.

26. A method, comprising:

providing a subject to which a drug has been administered, wherein the subject has a condition suspected of being treatable by the drug, and wherein the drug does not cause a measurable change to the condition of the subject within the first 24 hours after administering the drug;

determining a species withdrawn from the blood of the subject that is indicative of the drug administered to the subject;

determining compliance of the subject to a prescription involving the drug, based on the withdrawn species; and providing feedback to the subject and/or another person based on the compliance of the subject to the prescription.

27. The method of claim 26, wherein the drug does not cause a measurable change to the condition of the subject within the first week after administering the drug.

28. The method of claim 26, wherein the drug does not cause a measurable change to the condition of the subject within the first four weeks after administering the drug.

* * * * *